US006899896B2

(12) United States Patent
Curatolo et al.

(10) Patent No.: US 6,899,896 B2
(45) Date of Patent: May 31, 2005

(54) HYDROGEL-DRIVEN LAYERED DRUG DOSAGE FORM

(75) Inventors: William J. Curatolo, Niantic, CT (US); Kenneth C. Waterman, East Lyme, CT (US); Avinash G. Thombre, East Lyme, CT (US); Michael B. Fergione, Stonington, CT (US); Michael C. Roy, Gales Ferry, CT (US); Leah A. Appel, Bend, OR (US); Danni Supplee, Bend, OR (US); Dwayne T. Friesen, Bend, OR (US); Mark B. Chidlaw, Bend, OR (US); Ronald A. Beyerinck, Bend, OR (US)

(73) Assignee: Pfizer Inc, New York, NY (US)

( * ) Notice: Subject to any disclaimer, the term of this patent is extended or adjusted under 35 U.S.C. 154(b) by 33 days.

(21) Appl. No.: 09/745,096

(22) Filed: Dec. 20, 2000

(65) Prior Publication Data

US 2001/0044474 A1 Nov. 22, 2001

Related U.S. Application Data

(60) Provisional application No. 60/172,108, filed on Dec. 23, 1999.

(51) Int. Cl.[7] ............................. A61K 9/22; A61K 9/32; A61K 9/36; A61K 9/24
(52) U.S. Cl. ..................... 424/473; 424/468; 424/470; 424/475; 424/480; 424/482; 424/472; 514/772.2; 514/772.3; 514/777; 514/778; 514/781; 514/784; 514/951
(58) Field of Search .................. 424/464, 465, 424/480, 475, 474, 473, 468, 470, 482, 472

(56) References Cited

U.S. PATENT DOCUMENTS

| 4,327,725 A | 5/1982 | Cortese et al. ............... 128/260 |
| 4,536,518 A | 8/1985 | Welch, Jr. et al. ........... 514/647 |
| 4,609,374 A | 9/1986 | Ayer ............................ 604/892 |
| 4,612,008 A | 9/1986 | Wong et al. ................. 604/892 |
| 4,624,847 A | 11/1986 | Ayer et al. ...................... 424/15 |
| 4,755,180 A | 7/1988 | Ayer et al. ................ 604/892.1 |
| 4,765,989 A | 8/1988 | Wong et al. ................. 424/473 |
| 4,783,337 A | 11/1988 | Wong et al. ................. 424/468 |
| 4,784,858 A | 11/1988 | Ventouras .................... 424/468 |
| 4,837,111 A | 6/1989 | Deters et al. ................ 424/473 |
| 4,839,177 A | 6/1989 | Colombo et al. ........... 424/482 |
| 4,865,598 A | 9/1989 | Eckenhoff ................ 604/892.1 |
| 4,871,549 A | 10/1989 | Ueda et al. .................. 424/494 |
| 4,915,954 A | 4/1990 | Ayer et al. ................... 424/473 |

(Continued)

FOREIGN PATENT DOCUMENTS

| EP | 1027888 | 8/2000 | ............ A61K/9/26 |
| WO | WO9737640 | 10/1997 | ............ A61K/9/22 |
| WO | WO9901121 | 1/1999 | ......... A61K/31/135 |

Primary Examiner—James M. Spear
(74) Attorney, Agent, or Firm—Peter C. Richardson; Lorraine B. Ling; A. David Joran

(57) ABSTRACT

A controlled release dosage form for sertraline has a core comprising a sertraline-containing composition and a water-swellable composition wherein the water-swellable composition is in a separate region within the core. A coating around the core is water-permeable, water-insoluble, and has at least one delivery port therethrough. In one embodiment, the dosage form releases sertraline to the use environment at an average rate of 6 to 10 wt % per hour from the second to the twenth hour after introduction to a use environment and less than about 25 wt % for the first two hours and at least 70 wt % by the twelfth hour, where the percentages correspond to the mass of drug released from the tablet divided by the total mass of drug originally present in the tablet. In another embodiment, the dosage form releases less than about 25 wt % of sertraline to the use environment by the second hour after introduction of the dosage form to the use environment, and delivers at least 25 wt % from the eighth to the twenty-fourth hour.

144 Claims, 1 Drawing Sheet

U.S. PATENT DOCUMENTS

| | | | |
|---|---|---|---|
| 4,940,731 A | 7/1990 | Bick | 514/657 |
| 4,946,687 A | 8/1990 | Ayer et al. | 424/473 |
| 4,962,128 A | 10/1990 | Doogan et al. | 514/647 |
| 4,968,507 A | 11/1990 | Zentner et al. | 424/465 |
| 4,971,998 A | 11/1990 | Wurtman et al. | 514/654 |
| 4,992,278 A | 2/1991 | Khanna | 424/473 |
| 5,019,396 A | 5/1991 | Ayer et al. | 424/473 |
| 5,030,456 A | 7/1991 | Ayer et al. | 424/473 |
| 5,035,897 A | 7/1991 | Ayer et al. | 424/473 |
| 5,057,321 A | 10/1991 | Edgren et al. | 424/413 |
| 5,061,728 A | 10/1991 | Koe | 514/520 |
| 5,068,112 A | 11/1991 | Samejima et al. | 424/495 |
| 5,082,668 A | 1/1992 | Wong et al. | 424/473 |
| 5,091,190 A | 2/1992 | Kuczynski et al. | 424/473 |
| 5,120,548 A | 6/1992 | McClelland et al. | 424/473 |
| 5,126,142 A | 6/1992 | Ayer et al. | 424/438 |
| RE33,994 E | 7/1992 | Baker et al. | 424/465 |
| 5,128,145 A | 7/1992 | Edgren et al. | 424/473 |
| 5,130,338 A | 7/1992 | Bacopoulos et al. | 514/646 |
| 5,156,850 A | 10/1992 | Wong et al. | 424/473 |
| 5,160,744 A | 11/1992 | Joa et al. | 44/473 |
| 5,178,866 A | 1/1993 | Wright et al. | 424/473 |
| 5,178,867 A | 1/1993 | Guittard et al. | 424/473 |
| 5,183,942 A | 2/1993 | Nicolaou et al. | 424/473 |
| 5,185,158 A | 2/1993 | Ayer et al. | 424/473 |
| 5,190,763 A | 3/1993 | Edgren et al. | 424/473 |
| 5,192,550 A | 3/1993 | Edgren et al. | 424/473 |
| 5,200,197 A | 4/1993 | Wright et al. | 424/473 |
| 5,208,037 A | 5/1993 | Wright et al. | 424/473 |
| 5,221,536 A | 6/1993 | Edgren et al. | 424/473 |
| 5,246,710 A | 9/1993 | Ayer et al. | 424/473 |
| 5,246,711 A | 9/1993 | Ayer et al. | 424/473 |
| 5,260,069 A | 11/1993 | Chen | 424/451 |
| 5,273,752 A | 12/1993 | Ayer et al. | 424/438 |
| 5,284,662 A | 2/1994 | Koparkar et al. | 424/473 |
| 5,294,770 A | 3/1994 | Riddle et al. | 219/121.7 |
| 5,326,571 A | 7/1994 | Wright et al. | 424/473 |
| 5,358,721 A | 10/1994 | Guittard et al. | 424/473 |
| 5,366,738 A | 11/1994 | Rork et al. | 424/473 |
| 5,431,921 A | 7/1995 | Thombre | 424/424 |
| 5,455,046 A | 10/1995 | Baichwal | 424/457 |
| 5,458,887 A | 10/1995 | Chen et al. | 424/464 |
| 5,458,888 A | 10/1995 | Chen | 424/464 |
| 5,512,297 A | 4/1996 | Baichwal | 424/451 |
| 5,516,527 A | 5/1996 | Curatolo | 424/461 |
| 5,529,787 A | 6/1996 | Merrill et al. | 424/465 |
| 5,543,154 A | 8/1996 | Rork et al. | 424/473 |
| 5,543,155 A | 8/1996 | Fekete et al. | 424/473 |
| 5,554,387 A | 9/1996 | Baichwal | 424/488 |
| 5,607,696 A | 3/1997 | Rivera et al. | 424/473 |
| 5,654,005 A | 8/1997 | Chen et al. | 424/480 |
| 5,658,474 A | 8/1997 | Geerke | 219/121.71 |
| 5,660,861 A | 8/1997 | Jao et al. | 424/465 |
| 5,681,584 A | 10/1997 | Savastano et al. | 424/473 |
| 5,688,518 A | 11/1997 | Ayer et al. | 424/422 |
| 5,698,224 A | 12/1997 | Guittard et al. | 424/468 |
| 5,707,663 A | 1/1998 | Ayer et al. | 424/473 |
| 5,714,160 A | 2/1998 | Magruder et al. | 424/438 |
| 5,718,700 A | 2/1998 | Edgren et al. | 604/892.1 |
| 5,736,159 A | 4/1998 | Chen et al. | 424/480 |
| 5,783,213 A | 7/1998 | Rivera et al. | 424/473 |
| 5,792,471 A | 8/1998 | Curatolo | 424/480 |
| 5,795,591 A | 8/1998 | Lee et al. | 424/473 |
| 5,837,379 A | 11/1998 | Chen et al. | 424/465 |
| 5,840,332 A | 11/1998 | Lerner et al. | 424/464 |
| 5,840,335 A | 11/1998 | Wenzel et al. | 424/473 |
| 6,004,582 A | 12/1999 | Faour et al. | 424/473 |
| 6,068,859 A | 5/2000 | Curatolo et al. | 424/490 |

HYDROGEL-DRIVEN LAYERED DRUG DOSAGE FORM

This application is filed claiming priority from co-pending Provisional Application No. 60/172,108 filed Dec. 23, 1999.

BACKGROUND OF THE INVENTION

The present invention relates to a dosage form that provides a controlled release of sertraline to an environment of use.

Sertraline is a selective serotonin reuptake inhibitor which is useful, inter alia, as an antidepressant and anorectic agent, and in the treatment of obsessive-compulsive disorder, premenstrual dysphoric disorder, post-traumatic stress disorder, chemical dependencies, anxiety-related disorders, panic and premature ejaculation. See, for example, U.S. Pat. Nos. 4,536,518, 5,130,338, 4,971,998, 5,061,728, 4,940,731, and 4,962,128. The IUPAC name for sertraline is (1S-cis)-4-(3,4-dichlorophenyl)-1,2,3,4-tetrahydro-N-methyl-1-naphthalenamine, its empirical formula is $C_{12}H_{17}NCl_2$, and its structural formula is

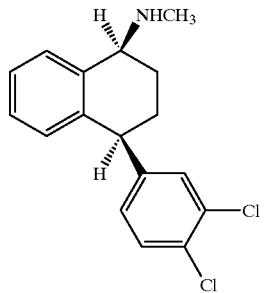

Sertraline is most commonly prescribed for therapy of depressive illness, in the general dose range 50–200 mgA/day wherein "mgA" refers to active sertraline in the free base, or neutral form. Sertraline has an elimination half-life of 23 hours, and is conventionally dosed once daily with immediate-release tablets.

Patients are generally initiated on sertraline at a dose of 50 mgA/day or less. Patients who do not respond at the 50 mgA dose are given higher doses. Initiation at doses greater than 50 mgA is generally avoided, when possible, because side effects such as dizziness, tremor, sweating, and gastrointestinal upset are generally believed to be more severe at higher doses. If necessary to achieve efficacy, higher doses may be reached by gradual increases in dosage.

Improved sertraline dosage forms which exhibit a lower incidence and/or severity of side effects would be advantageous because patient comfort and thus, compliance, would be improved and dosing could be initiated at doses higher than 50 mgA without the need for gradual increases. Initiation at higher starting doses would, in turn, be useful by potentially effecting a shorter onset of antidepressive action. Thus, such an improved sertraline dosage form which permits oral dosing of high doses of sertraline (e.g., 60 mgA and higher) with relatively reduced side effects would permit wider therapeutic application of sertraline therapy, and would accordingly provide a significant improvement in dosing compliance and convenience. Similarly, a dosage form which lowers the incidence and/or severity of side effects at lower doses would also be of significant value.

While such a once-a-day dosage form with reduced incidence or severity of side effects at a given dose is desirable, there are practical difficulties attendant to the development of such a dosage form. There is an upper limit on the size a dosage form may take. It is desired that a dosage form have a mass of less than 1 g, preferably less than about 800 mg, and more preferably no more than about 600 mg. In some cases, particularly when treating children or elderly patients, even lower mass tablets are desirable. Otherwise, the dosage form becomes so large that it is difficult to swallow.

The sertraline dose in an individual dosage form must be about 20 to 200 mgA, and preferably about 40 mgA to 150 mgA. This amount of active sertraline requires that an amount of sertraline salt (e.g., chloride, lactate, acetate, aspartate) be included in the core such that the desired amount of active agent is delivered. Assuming complete release of the drug, this means that to deliver 150 mgA, the core must contain 168 mg sertraline chloride, 194 mg sertraline lactate, 215 mg sertraline aspartate, or 179 mg sertraline acetate. Because sertraline occupies such a large portion of the core, the remaining excipients must be capable of providing the desired release profile using a minimum amount of material. Although this is most true at higher dose levels, it is often desirable to have a range of dosage forms that vary in dose with their size, but have a common composition. Thus, the tablet composition can be limited by the magnitude of the highest dose tablet.

Sertraline also has poor aqueous solubility, particularly at pH values above 6 to 7. This can result in low bioavailability, where bioavailability is the fraction of drug orally dosed that is absorbed into the blood stream, particularly in controlled-release dosage forms. Bioavailability from controlled release sertraline formulations can be significantly less than 100%, particularly at high drug doses and when a significant portion of the drug is delivered in the lower GI tract where the pH is relatively high and drug solubility is relatively low. While the solubility of sertraline is relatively high at low pH, e.g., 6 mgA/mL at pH 2.0, the solubility is much lower at higher pH. Thus, at a pH of 6.5 (generally corresponding to the pH in the duodenum), the solubility of sertraline is only about 1 mgA/mL, while at a pH of about 7.0 (generally corresponding to the pH of the small intestine), the solubility is about 0.2 mgA/mL, while at a pH of about 7.5 (generally corresponding to the pH in the colon), the solubilty is about 0.05 mgA/mL. While the lower pH in the stomach is ideal for solubilizing sertraline, it has been found that the incidence or severity of side effects such as nausea can be minimized by avoiding the release of excessive sertraline within the stomach. Thus, while the solubility of sertraline in the stomach is high, it is desired to limit the amount of sertraline released into the stomach to an acceptable level. However, the steadily decreasing solubility of sertraline as it proceeds down the GI tract (as pH increases) can result in low bioavailability if release is delayed too long.

As a result, to achieve the combined goals of (1) reduced incidence or severity of side effects (e.g., nausea), (2) high bioavailability, and (3) therapeutic blood levels over as long a time period as possible, a narrow range of drug release profiles is desired, which not only limits the amount of sertraline released into the stomach to an acceptable level, but also provides good absorption of sertraline either by (1) insuring that most of the sertraline is delivered prior to reaching the colon, or (2) delivering sertraline to the colon in such a manner that it is substantially absorbed. In addition, because the dose of sertraline may be high (e.g., 100 mgA to 200 mgA) and it is ideal to deliver a single tablet each day, it is desired that the dosage form deliver a substantial amount of the drug, leaving relatively low residual drug and that the amount of drug be a high fraction of the overall weight of the dosage form.

Under certain conditions, and in the presence of certain excipients used for formulation of conventional controlled-release dosage forms, sertraline may undergo adverse reactions that can alter its bioavailability or lead to undesirable impurities within a relatively short time, thus giving it a poor shelf life. Commercially acceptable controlled release dosage forms must provide patients with all of the desired attributes mentioned above while providing patients with a supply of sertraline that may be stored for relatively long periods of time and over a reasonably wide range of temperature and humidity conditions and still remain stable.

It is known that osmotic and hydrogel delivery devices of a bi-layer design, having a drug-containing composition and a water-swellable composition, may be used to provide controlled release of drugs through a surrounding coating having one or more delivery ports in the coating. However, a common problem encountered by such osmotic and hydrogel dosage forms is that residual drug remains within the dosage form after the dosage form exits that portion of the GI tract where drug absorption occurs. Such residual drug is not available for absorption and, accordingly, such dosage forms require increased amounts of drug to compensate for the failure of the dosage form to deliver all of the drug into the environment of use. In addition, the amount of such residual drug can be variable and may lead to variability of sertraline blood levels from patient to patient and from day to day.

Such bi-layer osmotic and hydrogel devices by definition contain water-swellable materials that occupy significant space within the core that otherwise would be available for sertraline. The water-swellable materials that provide delivery of the drug must be capable of providing a highly efficient delivery of sertraline, since very little of the mass of the dosage form may be available for the water-swellable material.

In addition, to maximize the bioavailability of the drug it is often desirable to have the dosage form begin delivery of sertraline immediately upon entering an aqueous environment of use. However, many bi-layer delivery systems exhibit a time lag before the onset of drug delivery. Several techniques have been proposed to overcome the time lag, but each has its own drawback. One technique has been to provide thin coatings around the dosage form. While this technique provides a quicker uptake of aqueous fluid, the thin coating often provides insufficient protection to the dosage form which becomes susceptible to damage during handling. Such thin coatings are also inherently weak and upon ingestion can rupture, causing uncontrolled release of drug. Yet another technique for eliminating the delivery time lag has involved providing holes or channels that allow communication of the water-swellable composition with the exterior fluid, but this often leads to unacceptable amounts of residual drug. Another technique involves coating the core with an immediate release drug formulation, but this requires additional processing steps, and is problematic in that the drug is often not stable in such coatings.

Yet another problem encountered with conventional bi-layer osmotically-driven and hydrogel-driven drug delivery systems is that conventionally such dosage forms require the presence of osmagents. These osmagents are often necessary, particularly when low water permeability coatings are used, to increase the drug release rate, but have the drawback of increasing the weight of the dosage form, thus further limiting the amount of sertraline which may be contained in the dosage form. Another drawback of inclusion of an osmagent is that it can potentially interact adversely with sertraline, thereby accelerating its degradation (in the case of certain sugars) or reducing its dissolution (in the case of salts such as chlorides). In addition, the presence of such osmagents increases the costs of manufacture due to the need to insure uniform concentrations of such ingredients throughout the composition.

Sustained and delayed release dosage forms of sertraline as well as a variety of sertraline compositions have been disclosed in commonly assigned U.S. patent application Ser. No. 09/380,885 filed Sep. 7, 1999 now abandoned, U.S. patent application Ser. No. 09/380,825 filed Sep. 7, 1999, and U.S. patent application Ser. No. 09/380,900 filed Sep. 7, 1999. However, none of these disclose a dosage from where the drug is in the form of an amorphous dispersion or a bi-layer osmotic dosage form that permits high drug loading, stability and optimum drug release profiles, and high bioavailability, all of which are possible with the present invention.

In addition, a variety of bi-layer osmotic and hydrogel-driven devices for many different drugs have been disclosed. See, e.g. Wong et al., U.S. Pat. No. 5,082,668; Eckenhoff, U.S. Pat. No. 4,865,598; Courtese et al., U.S. Pat. No. 4,327,725; and Ayer et al., U.S. Pat. No. 5,126,142. Nonetheless, the prior art bi-layer dosage forms do not disclose the means by which sertraline, a poorly soluble, hydrophobic, and potentially reactive drug, may be optimally delivered to a use environment in a controlled release fashion.

Accordingly, there is still a need in the art for a controlled release dosage form of sertraline that results in a highly efficient delivery of sertraline to an environment of use with very little residual drug, that allows high drug loading so as to decrease the dosage form size, that begins delivering drug soon after entering a desired environment of use, that limits the number of other components in the dosage form, that reduces the frequency or severity of negative side effects by limiting the release of sertraline to the stomach to an acceptable level, and that simultaneously achieves high bioavailability. Obtaining such high bioavailability may require that either the sertraline release profile be carefully controlled so that substantially complete release is achieved prior to entering the colon or, when delivery is continued in the colon, modifying the material released such that the absorption of sertraline in the colon is enhanced. These needs and others which will become apparent to one skilled in the art are met by the present invention, which is summarized and described in detail below.

BRIEF SUMMARY OF THE INVENTION

The present invention overcomes the drawbacks of the prior art by providing a dosage form for the controlled release of sertraline. The basic dosage form common to all aspects of the present invention has a core comprising a sertraline-containing composition and a water-swellable composition wherein the water-swellable composition is in a separate region within the core. A coating around the core is water-permeable, water-insoluble and has at least one delivery port therethrough.

In referring to the precentage of the core, or composition that the sertraline comprises, percentages given in wt % refer to the mass of sertraline form present divided by the total mass of the core or composition multiplied by 100. Release rates, given in wt %, refer to the mass of sertraline released divided by the total mass of sertraline multiplied by 100. As used here and in the claims, the average rate of sertraline release per hour for a time period is defined as the wt % sertraline released during the time period divided by the duration (in hours) of the time period. For example, a dosage form that delivers 10 wt % of sertraline by 2 hours and 90 wt % by 12 hours following delivery to a use environment would have an average rate of sertraline release of 8 wt % per hour for the second to the twelfth hours. It should be noted that this same dosage form may release much of the sertraline prior to the twelfth hour (for example, 80 wt % of the sertraline by the fourth hour) and thus may have a release rate for the 2-hour to 4-hour time period that is much higher than the average release rate of 8 wt % per hour, which is the average from the 2- to 12-hour period.

In a first aspect of the invention, the sertraline-containing composition contains sertraline and an entraining polymer. The dosage form has a high drug loading, with sertraline being present in an amount of at least 20 mgA and making up at least about 20 wt %, preferably 30 wt %, more preferably 40 wt % or higher of the sertraline-containing composition. Sertraline is present in the form of a pharmaceutically acceptable salt, and following introduction of the dosage form to a use environment, the dosage form releases sertraline to the use environment at an average rate of from about 4.5 to 10 wt % per hour from the second to the twelfth hour and less than about 25 wt % for the first two hours and at least 70 wt % by the twelfth hour.

In a second aspect of the invention, the sertraline-containing composition also comprises polyethylene oxide (PEO) having a molecular weight of at least 500,000, and a fluidizing agent. The dosage form has the same sertraline release profile as the first aspect of the invention.

In a third aspect of the invention, the water-swellable composition contains substantially no osmotically effective agent. The sertraline-containing composition comprises sertraline and a polymeric entraining agent. The dosage form has the same sertraline release profile as the first aspect of the invention.

In a fourth aspect of the invention, the sertraline-containing composition comprises sertraline and a polymeric entraining agent. The coating is a hydrophilic cellulosic polymeric coating that is porous. The dosage form has the same sertraline release profile as the first aspect of the invention.

In a fifth aspect of the invention, the dosage form has an extended sertraline release profile. The dosage form is like that of the first aspect of the invention mentioned above, except that the dosage form delivers less than about 25 wt % of sertraline to the use environment by the second hour after introduction of the dosage form to the use environment, and delivers at least about 40 wt % by the eighth hour and delivers at least about 25 wt % from the eighth to the twenty-fourth hour. Thus, the dosage form releases sertraline to the use environment at an average rate of from about 3 to about 13 wt % per hour from the second to the eighth hour. At least a portion of the sertraline is delivered such that improved absorption in the lower GI tract is observed.

In a sixth aspect of the invention, sertraline is present in the form of an amorphous dispersion.

In a seventh aspect of the invention, the sertraline-containing composition contains sertraline, PEO, and a binder. The sertraline-containing composition is wet-granulated using a mixture of a lower alcohol and water.

In an eighth aspect of the invention, the sertraline-containing composition comprises sertraline, an entraining polymer, and a concentration-enhancing polymer. The dosage form provides a maximum concentration of sertraline in a use environment that is at least 1.25-fold higher than the equilibrium concentration of sertraline in the use environment provided by a control dosage form, and a concentration of sertraline in the use environment that exceeds the equilibrium concentration for a longer time than a concentration provided by the control dosage form exceeds said equilibrium concentration, where the control dosage form is free from the concentration-enhancing polymer and comprises an equivalent quantity of sertraline. The dosage form provides an elevated sertraline concentration above the equilibrium concentration relative to the control dosage form for at least 15 minutes, and more preferably for longer than 30 minutes.

A ninth aspect of the invention comprises a method of treating a disorder in a patient that is susceptible to treatment by administering a therapeutic amount of sertraline, comprising introducing a sertraline-containing dosage form of the invention to an environment of use in the patient.

The various aspects of the present invention have one or more of the following advantages. The dosage forms of the present invention release sertraline at certain rates and amounts so as to reduce the incidence or severity of side effects resulting from the delivery of excessive sertraline to the stomach. In addition, the dosage forms either deliver a large fraction of the total sertraline dose prior to entry of the dosage form into the colon, or enhance the absorption of sertraline from the large intestine or colon by increasing the concentration of dissolved sertraline. The dosage forms are also capable of delivering relatively high doses of sertraline while minimizing the amounts of other materials needed for controlled release, thus minimizing tablet size and weight. The dosage forms are also capable of delivering greater amounts of drug to the desired environment of use, resulting in less residual drug than is the case with conventional dosage forms. In addition, the dosage forms are capable of higher drug loadings compared to conventional compositions of poorly soluble, hydrophobic drugs.

The present invention also allows for the control of the time lag in the delivery of sertraline. Thus, where sertraline is desired to be almost completely released prior to entering the colon, the dosage forms may begin releasing sertraline to the use environment soon after introduction to the use environment. This allows the achievement of high bioavailability while still keeping the amount of sertraline released to the stomach sufficiently low that adverse GI side effects are generally avoided. Alternatively, where the concentration of dissolved sertraline is improved at high pH, the dosage forms are capable of delaying release of sertraline so as to minimize the amount of sertraline released into the stomach and also extend the absorption time to achieve more constant sertraline blood levels.

In addition, the present invention prevents or retards the decomposition of sertraline during storage of the sertraline controlled-release dosage form.

The foregoing and other objectives, features, and advantages of the invention will be more readily understood upon consideration of the following detailed description of the invention, taken in conjunction with the accompanying drawings.

DETAILED DESCRIPTION OF THE INVENTION

Figure 1:
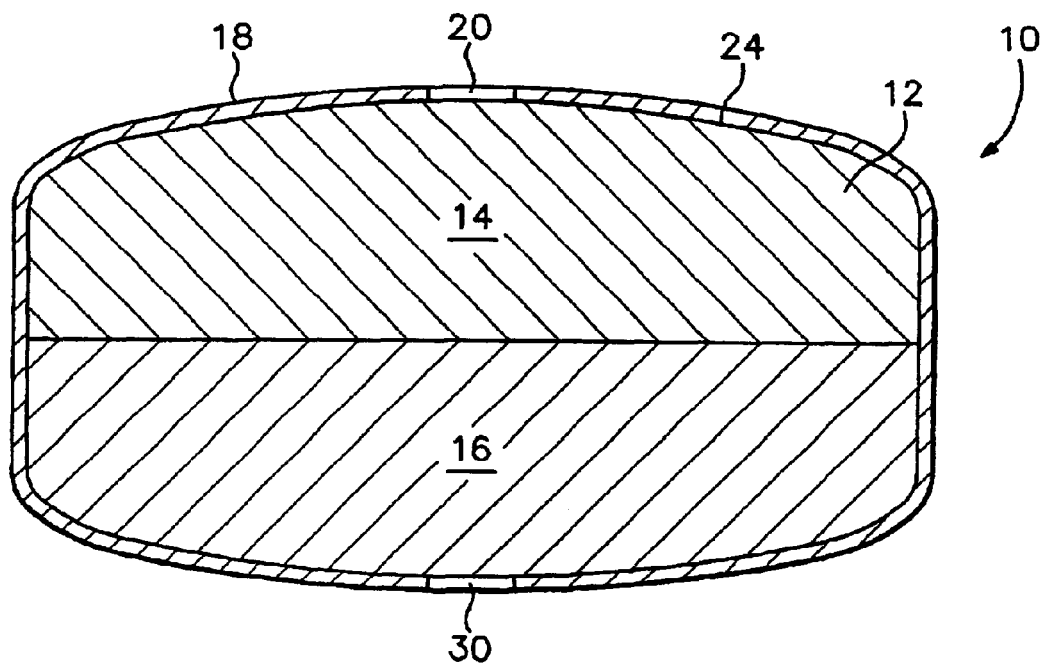
FIG. 1 is a schematic cross section of an exemplary dosage form of the present invention.

The present invention provides a controlled release dosage form that is specifically designed to provide controlled release by a mechanism not dependent primarily on the drug diffusion rate. Referring now to the drawings wherein like numerals refer to the same elements, FIG. 1 shows a dosage form 10 having a core 12 comprised of a sertraline-containing composition 14 and a water-swellable composition 16. The drug-containing composition and the water-swellable composition occupy separate regions in the core 12. By "separate regions" is meant that the two compositions occupy separate volumes, such that the two are not substantially mixed together. Of course, a small amount of intermixing of the compositions may occur where the compositions come in contact with each other, for example, at the interface between the two layers. A coating 18 surrounds the core 12 and is water-permeable, water-insoluble and has one or more delivery ports 20 therethrough. In use, the core 12 imbibes water through the coating 18 from the environment of use such as the gastrointestinal tract. The imbibed water causes the water-swellable composition 16 to swell, thereby increasing the pressure within the core 12. The imbibed water also causes the sertraline-containing composition to increase its fluidity. The pressure difference between the core 12 and the environment of use drives the delivery of the fluidized sertraline-containing composition 14. Because the coating 18 remains intact, the sertraline-containing composition 14 is extruded out of the core 12 through the delivery port(s) 20 into the environment of use. Because the water-swellable composition 16 contains no sertraline, almost all of the sertraline is extruded through the delivery port(s) 20, as the water-swellable composition swells, leaving very little residual drug.

The dosage form of the present invention delivers the sertraline to an environment of use primarily by "extrusion" rather than primarily by diffusion of drug out of the dosage form. The term "extrusion" as used herein is intended to convey an expulsion or forcing out of some or all of the drug through the coating by hydrostatic forces, to be distinguished from delivery by a diffusion mechanism or by erosion of the mass of the device. The sertraline may be delivered by extrusion either in the form of a suspension of solids in aqueous solution or the sertraline may be in solution, to the extent dissolution has taken place in the core 12. Sertraline is released to the environment of use as a result of the influx of water into the core and the resulting extrusion of sertraline entrained within an entraining polymer through one or more delivery ports or pores in the coating.

Reference to the "release" of sertraline as used herein means (1) transport of sertraline from the interior of the dosage form to its exterior such that it contacts the fluid within a mammal's gastrointestinal (GI) tract following ingestion or (2) transport of sertraline from the interior of the dosage form to its exterior such that it contacts an in vitro test medium for evaluation of the dosage form by an in vitro test as described below. Reference to a "use environment" or "environment of use" can thus be either to in vivo GI fluids or to in vitro test media. "Introduction" to a use environment includes either by ingestion or swallowing, where the use environment is in vivo, or being placed in a test medium where the use environment is in vitro.

RELEASE CHARACTERISTICS

The key to the present invention is the delivery of sertraline to a use environment at specific amounts and times to minimize side effects and maximize absorption within the body. The dosage forms provide sertraline release profiles that meet the following criteria.

First, the dosage forms reduce side effects from sertraline released into the stomach by releasing relatively small amounts of sertraline into the stomach. At the same time, to maximize bioavailability and maintain sertraline blood levels within the desired range, it is often desirable to release a portion of the sertraline in the stomach.

Second, the dosage forms release sertraline so that a sufficient amount may be absorbed. Because the solubility of sertraline steadily decreases as it proceeds down the GI tract toward the colon due to the gradual increase in pH from a value of near 6 to 6.5 in the duodenum to a value of 7.5 or more in the colon, when sertraline is released as relatively large crystals of its relatively low solubility hydrochloride salt, the release is substantially complete by the time the dosage form reaches the lower portion of the colon; this typically occurs 6 to 12 hours after ingestion. Alternatively, at least a portion of the sertraline is delivered such that improved absorption is observed in the lower GI tract by increasing the concentration of dissolved sertraline in the colon. This increased dissolved sertraline concentration is achieved by (1) increasing the local solubility of sertraline by co-delivery of solubilizers, such as an organic acid, (2) increasing the dissolution rate, such as by delivery of sertraline salts with a reduced particle size, (3) use of a high-solubility salt form, (4) delivery of the sertraline as a solid amorphous dispersion, (5) by co-delivery of a concentration-enhancing polymer, or (6) combinations thereof.

Third, sertraline is released at a substantially constant rate.

Finally, the dosage forms deliver a substantial amount of the sertraline incorporated into the dosage form, leaving a relatively small residual amount of the drug within the core after 24 hours.

The dosage forms of the present invention provide one of two drug release profiles.

In a first profile, sertraline is released to a use environment at an average rate of from 4.5 to 10 wt % per hour from the second to the twelfth hour, less than about 25 wt % of sertraline during the first 2 hours and at least 70 wt %, preferably 80 wt %, more preferably 90 wt %, most preferably 95 wt %, by the twelfth hour. Thus, most of the sertraline is released prior to reaching the colon, yet only a relatively small portion is released into the stomach. To minimize side effects at high sertraline doses, it may be preferable in some cases for the dosage form to release less than 15 wt % of sertraline during the first 2 hours after introduction to the use environment.

In one embodiment, a dosage form having the first release profile releases sertraline relatively quickly into the use environment, such that the dosage form exhibits little or no lag time. Preferably, the dosage form releases at least 5 wt %, preferably 10 wt %, more preferably 15 wt % of sertraline within the first two hours after introduction of the dosage form to the use environment. When the use environment is the human GI tract, by quickly beginning the release of sertraline, the dosage form increases the total amount of time that sertraline is present in the portion of the GI tract where absorption of sertraline is most rapid, with the results of increased absorption and greater bioavailability. This may be accomplished, for example, by placing a sertraline-containing, immediate release coating over the water-permeable, water-insoluble coating.

In a second embodiment, the dosage from having the first release profile releases most of the sertraline relatively rapidly. Preferably, such dosage forms release less than 20 wt % of the sertraline during the first two hours but greater than 70 wt % of the sertraline by the sixth hour. Such dosage forms are believed to provide a desirable combination of reduced adverse side effects and high bioavailability.

In a second release profile, referred to as an "extended release profile," delivery of sertraline is sustained over a longer time period in order to maintain sertraline blood levels at a desired level for a longer time period. In this extended release profile, the dosage form releases less than about 25 wt % during the first 2 hours after introduction of the dosage form to the use environment and at least about 40 wt % by the eighth hour and at least about 25 wt % from the eighth to the twenty-fourth hour. However, because a significant fraction of the sertraline is released within the colon where sertraline solubility and therefore absorption rate is relatively low, the concentration of dissolved sertraline may be temporarily improved sufficiently to improve absorption through one or more of the following methods: (1) delivery of solubilizers such as organic acids, (2) increasing dissolution rate by utilizing sertraline salts that have a reduced particle size, (3) the use of highly soluble salt forms of sertraline, (4) delivery of sertraline in the form of an amorphous dispersion containing sertraline, (5) by co-delivery of a concentration-enhancing polymer, or (6) combinations thereof. In some cases it may be preferable for such extended release profile dosage forms to release less than 15 wt % of sertraline during the first 2 hours after introduction into the use environment.

For both of these release profiles, it is important that the dosage form release a substantial portion of sertraline originally present in the tablet core to the use environment with minimal residual drug remaining in the dosage form after 24 hours. The dosage forms of the present invention following the first release profile release at least 80 wt % of sertraline, preferably at least 90 wt %, and more preferably at least 95 wt % of sertraline to the use environment within 12 hours after introduction of the dosage form to the use environment. The dosage forms of the present invention following the extended release profile release at least 80 wt %, preferably at least 90 wt %, and more preferably at least 95 wt % of sertraline to the use environment within 24 hours after introduction of the dosage form to the use environment.

An in vitro test may be used to determine whether a dosage form provides a release profile within the scope of the present invention. Two types of in vitro tests may be used, a residual test and a direct test, although other conventional tests known in the art used to measure drug release may also be used.

In the residual test, the dosage form is first placed into a stirred USP type 2 dissoette flask containing 900 mL of a buffer solution simulating gastric fluid (10 mM HCl, 100 mM NaCl, pH 2.0, 261 mOsm/kg) for 2 hours, then removed, rinsed with deionized water, and transferred to a stirred flask containing 900 mL of a buffer solution simulating the contents of the small intestine (6 mM $KH_2PO_4$, 64 mM KCl, 35 mM NaCl, pH 7.2, 210 mOsm/kg). In both flasks the dosage form is placed in a wire support to keep the tablet off of the bottom of the flask, so that all surfaces are exposed to the solution and the solutions are stirred using paddles that rotate at 50 revolutions per minute. At each time interval, a single tablet is removed from the solution and placed in 100 mLs of a recovery solution (50/50 wt/wt ethanol/water, pH 3), and stirred vigorously at ambient temperature overnight in a flask, stirring to dissolve the drug remaining in the tablet. Samples of the recovery solution containing the dissolved drug are filtered using a Gelman nylon Acrodisc® 13, 0.45 μm pore size, and placed in an HPLC vial and capped. Residual drug is analyzed by HPLC using a Phenomenex Ultracarb 5 ODS 20 column. The mobile phase consists of 35 vol. % TEA-acetate buffer (3.48 mL triethanolamine and 2.86 mL glacial acetic acid in 1 L HPLC-grade $H_2O$) in acetonitrile. Drug concentration is calculated by comparing UV absorbance at 230 nm to the absorbance of sertraline controls. The amount remaining in the tablets is subtracted from the total drug originally in the tablet to obtain the amount released at each time interval.

In the direct test, samples of the dosage form are placed into a stirred USP type 2 dissoette flask containing 900 mL of a receptor solution. The receptor solution is either USP sodium acetate buffer (27 mM acetic acid and 36 mM sodium acetate, pH 4.5) or 88 mM NaCl. Samples are taken at periodic intervals using a VanKel VK8000 autosampling dissoette with automatic receptor solution replacement. Tablets are placed in a wire support as above, paddle height is adjusted, and the dissoette flasks stirred at 50 rpm at 37° C. Periodically, the autosampler removes a sample of the receptor solution, and the concentration of sertraline in the receptor solution is analyzed directly by HPLC using the procedure outlined above. Since the drug is usually extruded from the dosage form as a suspension in an entraining polymer, there is often a time lag between when the drug is released and when it is dissolved in the test media, and thus, measured in the direct test. This time lag depends on the solubility of the drug, the test media, and the ingredients of the drug-containing composition, but typically is on the order of 30 to 90 minutes. Accordingly, results of the direct test tend to underestimate the amount of sertraline actually released.

Alternatively, an in vivo test may be used to is determine whether a dosage form provides a release profile within the scope of the present invention. Dosage forms are dosed to a group of humans, dogs or other suitable mammals and dosage form release and drug absorption is monitored either by (1) periodically withdrawing blood and measuring the serum or plasma concentration of drug or (2) measuring the amount of drug remaining in the dosage form (residual drug) following its exit from the anus or (3) both (1) and (2). In the second method, residual drug is measured by recovering the tablet upon exit from the anus of the test subject and measuring the amount of sertraline remaining in the dosage form using the same procedure described above for the in vitro residual test. The difference between the amount of sertraline in the original dosage form and the amount of residual sertraline is a measure of the amount of sertraline released during the mouth-to-anus transit time. This test has limited utility since it provides only a single sertraline release time point but is useful in demonstrating the correlation between in vitro and in vivo release.

In one in vivo method, the serum or plasma drug concentration is plotted along the ordinate (y-axis) against the blood sample time along the abscissa (x-axis). The data may then be analyzed to determine sertraline release rates using any conventional analysis, such as the Wagner-Nelson or Loo-Riegelman analysis. See also, Welling, "Pharmacokinetics: Processes and Mathematics," ACS Monograph 185, Amer. Chem. Soc. (1986). It should be noted that such a procedure tends to underestimate the amount of sertraline released, particularly at later time points because much of the sertraline released from the dosage form may remain undissolved in the lower GI tract where the pH is high and the sertraline solubility is low. Therefore, the in vitro tests previously described are preferred for determining whether the release profile of a dosage form is within the scope of the present invention.

However, in the case of dosage forms with an extended sertraline release profile, an in vivo test is desirable to demonstrate that at least a portion of the sertraline is delivered such that improved absorption in the lower GI tract is observed.

An in vivo test, such as a crossover study, may be used to determine whether a dosage form provides improved absorption in the lower GI tract. In an in vivo crossover study a "test dosage form" that displays in an in vitro test an extended release profile is dosed to half a group of 12 or more humans and, after an appropriate washout period (e.g., one week) the same subjects are dosed with a "control dosage form" that displays a similar in vitro sertraline release profile as the "test dosage form." The sertraline-containing composition in the control dosage form consists of crystalline sertraline hydrochloride of a standard 10 μm average particle size having substantially no solubilizer such as organic acid present in the control dosage form. The other half of the group is dosed with the control dosage form first, followed by the test dosage form. The bioavailability is measured as the area under the curve (AUC) determined for each group. In vivo determinations of AUC can be made by plotting the serum or plasma concentration of drug along the ordinate (y-axis) against time along the abscissa (x-axis). By measuring the AUC for a population to which the test composition has been administered and comparing it with the AUC for the same population to which the control has been administered, the test composition can be evaluated. Preferably, the test/control AUC ratio is determined for each subject, and then the ratios are averaged over all subjects in the study. The determination of AUCs is a well-known procedure and is described, for example, in the same Welling ACS Monograph mentioned above. A test dosage form is considered to provide improved absorption in the GI tract if the AUC for the time period from about the fifth hour to about the twenty-fourth hour following ingestion of the dosage form is at least 1.2-fold the AUC value for the control dosage form.

SERTRALINE-CONTAINING COMPOSITION

With reference to FIG. 1, the sertraline-containing composition 14 of the drug dosage form 10 includes at least sertraline, and includes at least an entraining water-swellable polymer and preferably additional excipients. In one aspect of the present invention, sertraline is employed in the form of its pharmaceutically acceptable crystalline salts, and may be in anhydrous or hydrated form. For convenience and consistency, reference herein to "sertraline" in terms of either therapeutic amounts or in release rates is to active sertraline, abbreviated as "mgA," i.e., the non-salt, non-hydrated free base having a molecular weight of 306.2 g/mol. Amounts in mgA can conveniently be converted to equivalent weights for whatever salt form is desired, as previously described. Preferably, the dosage form contains at least 20 mgA of sertraline. Because the desired dose may be higher, the sertraline-containing composition may contain as much as 200 mgA of sertraline. Generally, sertraline will make up at least 20 wt %, preferably 30 wt %, and more preferably 40 wt % of the sertraline-containing composition.

In one preferred embodiment, sertraline is present as a crystalline salt of the drug. It has been found that the neutral or free base form of sertraline is more reactive, being particularly prone to oxidation relative to its protonated salt form. To maintain the drug as completely as possible in its protonated form, it has been found that it is preferable, when using a pure drug form, that it be kept in its crystalline state rather than in its non-crystalline or amorphous state. It has also been found that of the various pharmaceutically acceptable salts of sertraline, the hydrochloride salt is the most stable. However, other salt forms may be used as long as care is taken in choosing other excipients and in choosing processing conditions.

Some salt forms of sertraline are capable of forming more than one crystal structure, known as polymorphs. See, for example, U.S. Pat. No. 5,248,699, the pertinent disclosures of which are incorporated herein by reference. It has been found that different polymorphs may have different aqueous solubilities, and thus may provide different degrees of bioavailability. Different polymorphs may also have different optimum humidity and storage conditions. In order to maintain consistent dosing, it is preferred that the dosage form comprise a single polymorph, so that the bioavailability from dosage form to dosage form remains essentially constant. While a single polymorph is desired, nevertheless as a practical matter, other polymorphs are often present in small amounts. Accordingly, it is preferred that at least 95 wt % of sertraline is present as a single polymorph. To obtain maximum chemical stability, it has been found that the crystalline HCl salt of sertraline is preferred. However, in some cases, to improve sertraline dissolution and absorption to obtain high bioavailability, particularly in the colon, other higher-solubility crystalline salt forms may be preferred. Acceptable alternative salt forms include sertraline lactate, sertraline acetate and sertraline aspartate.

In an alternative embodiment, sertraline is present in the form of an amorphous solid dispersion, meaning that sertraline is dispersed in a polymer so that a major portion of sertraline is in a substantially amorphous or non-crystalline state, and its non-crystalline nature is demonstrable by X-ray diffraction analysis or by differential scanning calorimetry. The dispersion may contain from about 5 to 90 wt % sertraline, preferably 20 to 70 wt %, most preferably 25 to 55 wt %. The polymer is aqueous-soluble and inert, and is preferably concentration-enhancing. Suitable polymers and methods of making solid amorphous dispersions are disclosed in commonly assigned U.S. patent application Ser. Nos. 09/495,059 and 09/495,061 both filed Jan. 31, 2000, respectively, the pertinent disclosures of which are incorporated herein by reference. The concentration-enhancing polymer used to form the dispersion may be selected from the group consisting of ionizable and non-ionizable cellulosics, and vinyl polymers and copolymers having substituents selected from the group consisting of hydroxyl, alkylacyloxy, and cyclicamido. Due to the need to keep the sertraline in its protonated form to retain good stability, preferred polymers are those that are acidic in nature.

In particular, polymers that have carboxylic acid functionality in their protonated forms are preferred. Specific preferred polymers are hydroxypropylmethyl cellulose acetate succinate (HPMCAS), hydroxypropylmethyl cellulose phthalate (HPMCP), cellulose acetate phthalate (CAP) and cellulose acetate trimellitate (CAT). In addition, to keep the chemical environment of the sertraline highly acidic, it may be desirable to include an acidic excipient such as citric acid, succinic acid, fumaric acid, tartaric acid, phosphoric acid, or hydrochloric acid in the sertraline amorphous solid dispersion.

When present in crystalline form, sertraline may be present in average particle sizes up to about 50 μm. Preferably, sertraline is micronized using a jet mill or other device known in the art, to have smaller average particle sizes on the order of less than about 5 μm. In addition, surfactants, polymers or other substances known in the art may be added during the milling process to aid in reducing the particle size of sertraline and, in particular, preventing aggregation of sertraline particles. It is believed that such small average particle sizes may enhance the bioavailability of sertraline by improving its dissolution rate. This is particularly useful in enhancing drug absorption in the colon where a release profile is used in which a substantial amount of drug (typically 20 to 50 wt %) is released 5 hours or more following ingestion. Such small sertraline crystals may be part of larger granules such that upon dissolution of the granules, the small crystals are released.

In a preferred embodiment, sertraline is present in a highly soluble salt form. As used herein, a "highly soluble salt form" of sertraline shows improved aqueous solubility relative to sertraline HCl. Because these salt forms provide greater aqueous solubility of sertraline compared with the HCl salt form, such salt forms may show improved in vitro dissolution, and are also expected to show improved in vivo dissolution. Although the high pH and high chloride content of GI fluids may result in such sertraline salts converting in vivo to the free-base or HCl salt forms of sertraline, use of high-solubility salts are expected to maintain, at least temporarily, a somewhat higher average drug concentration and therefore should show improved bioavailability relative to sertraline HCl. Highly soluble salt forms of sertraline include acetate, lactate and aspartate salts.

The sertraline-containing composition must contain various other excipients that are required in order to obtain a dosage form that meets all of the requirements set out herein. In particular, due to the low solubility, high hydrophobicity, and high reactivity of sertraline relative to most drugs, the type and amount of such excipients must be chosen carefully.

The sertraline-containing composition must include an entraining agent in the form of a water-swellable polymer. Such water-swellable polymers are often referred to in the pharmaceutical arts as an "osmopolymer" or a "hydrogel." The entraining agent suspends or entrains the drug so as to aid in the delivery of the drug through the delivery port(s) 20 to the environment of use. While not wishing to be bound by any particular theory, it is believed that upon the imbibition of water into the dosage form, the entraining agent has enough viscosity to allow it to suspend or entrain the drug, while at the same time remaining sufficiently fluid to allow the entraining agent to pass through the delivery port(s) 20 along with the drug. The amount of the entraining agent present in the sertraline-containing composition may range from about 20 wt % to about 80 wt % of the sertraline-containing composition. The entraining agent may be a single material or a mixture of materials. Non-crosslinked PEO may be used as the entraining agent. Other suitable entraining agents include hydroxypropyl cellulose (HPC), hydroxypropylmethyl cellulose (HPMC), methylcellulose (MC), hydroxyethyl cellulose (HEC) and polyvinyl pyrrolidone (PVP), as well as mixtures of these polymers with PEO.

The choice of the molecular weight for the PEO depends in part on whether the PEO makes up the bulk of the non-sertraline portion of the sertraline-containing composition, or whether significant amounts of other low-molecular weight water-soluble excipients are included; that is, the PEO molecular weight choice depends on the fraction of the sertraline-containing composition that is PEO. This is critical in order for the sertraline-containing composition, upon delivery to the use environment; to rapidly imbibe water and become sufficiently fluid that it may be delivered to the use environment. Should the sertraline-containing composition not become fluid rapidly, the dosage form can swell and rupture the coating that surrounds the core, potentially causing failure of the dosage form. This is particularly a problem with sertraline because high-permeability coatings are desired which are often thin and weak relative to low-permeability coatings. Because sertraline is poorly aqueous-soluble and hydrophobic, it tends to remain in the crystalline form while water is imbibed into the dosage form. Accordingly, the remaining materials in the sertraline-containing composition must become sufficiently fluid to allow the sertraline-containing composition to exit the port 20 before the coating 18 bursts. Where the excipients of the sertraline-containing composition are primarily PEO (e.g., PEO makes up about 60 wt % or more of the non-sertraline components of the sertraline-containing composition), it is generally preferred that the PEO have an average molecular weight of from about 100,000 to 300,000 daltons. (As used herein and in the claims, reference to molecular weights of polymers should be taken to mean average molecular weights.) In general, when the particle size of the granules that make up the sertraline-containing layer are small, typically less than about 300 μm, a PEO molecular weight of about 200,000 daltons yields excellent results. However, when a significant fraction of the granules exceeds a diameter of about 425 μm, it has been found that use of a higher molecular weight is preferred, preferably 300,000; this molecular weight PEO is fluid enough to allow the sertraline-containing composition to exit the port 20 and release it to the environment of use, but has a high enough viscosity to entrain the sertraline.

Alternatively, another embodiment of the present invention uses a higher molecular weight of PEO from about 500,000 to 800,000 daltons at a lower fraction of the non-sertraline excipients, a portion of the PEO being replaced with a fluidizing agent. Ordinarily, when PEO makes up about 60 wt % or more of the non-sertraline components of the sertraline-containing composition, PEO having a molecular weight of 500,000 daltons or more makes the sertraline-containing layer too viscous, and can result in a rupture of the coating or at least in a delay of the release of sertraline. However, it has been found that such higher molecular weight PEO is preferred when the non-sertraline components of the sertraline-containing composition comprise less than about 60 wt % PEO and also contain a fluidizing agent. When using a higher molecular weight PEO, the amount of fluidizing agent present in the sertraline-containing composition may range from about 5 to about 50 wt %, preferably 10 to 30 wt % of the sertraline-containing composition. Preferred fluidizing agents are low molecular weight, water-soluble solutes such as non-reducing sugars and organic acids with aqueous solubilities of 30 mg/mL or greater. Where the fluidizing agent is a sugar, the sugar must be non-reducing due to the high reactivity of sertraline, which has been found to degrade by reacting with reducing sugars such as fructose or glucose. Thus, in order to prevent such degradation, non-reducing sugars should be chosen. Suitable non-reducing sugars include xylitol, mannitol, sorbitol, and maltitol. Exemplary salts useful as a fluidizing agent include sodium chloride, sodium lactate and sodium acetate; however, non-chloride salts are preferred. Exemplary organic acids useful as a fluidizing agent include adipic acid, citric acid, malic acid, succinic acid and tartaric acid.

The presence of the fluidizing agent, along with a relatively low level of higher molecular weight PEO (e.g., about 500,000 to about 800,000 daltons) allows the sertraline-containing composition to rapidly reach a low viscosity upon imbibition of water in the use environment. Surprisingly, this combination of higher molecular weight PEO and a fluidizing agent has numerous advantages: (1) delivery of sertraline begins quickly, i.e., the time lag is short, (2) the build-up of pressure in the tablet is reduced, allowing thinner, more permeable coatings to be reliably used, and (3) inclusion of a non-reducing sugar and PEO yields a sertraline-containing layer with improved tableting and flow properties. In particular such compositions tend to diminish "crowning," a problem discussed below. In addition, it has been found that such an embodiment is capable of delivering relatively high amounts of sertraline to a use environment. For example, it has been shown that for such dosage forms, sertraline salts may make up about 28 wt % of the tablet core and still deliver more than about 88 wt % of the sertraline within 12 hours.

The PEO may be screened in order to provide a more uniform range of particle sizes. Generally, a narrower particle size distribution will lead to better flow characteristics for the material. This is important when manufacturing mass quantities of tablets, since better flow characteristics will allow for higher rates of production and higher manufacturing yield.

The sertraline-containing composition may also contain other water-swellable polymers. For example, the sertraline-containing composition may contain relatively small amounts of water-swellable polymers that greatly expand in the presence of water. Such water-swellable polymers include sodium starch glycolate, sold under the trade name EXPLOTAB, and croscarmelose sodium, sold under the trade name AC-DI-SOL. Such polymers may be present in amounts ranging from 0 wt % to 10 wt % of the sertraline-containing composition.

The sertraline-containing composition may optionally include osmotically effective solutes, often referred to as "osmogens" or "osmagents." The amount of osmagent present in the drug-containing composition may range from about 0 wt % to about 50 wt %, preferably 10 wt % to 30 wt % of the sertraline-containing composition. Typical classes of suitable osmagents are water-soluble salts, sugars, organic acids, and other low-molecule-weight organic compounds that are capable of imbibing water to thereby create an osmotic pressure gradient across the barrier of the surrounding coating. Typical useful salts include magnesium sulfate, magnesium chloride, calcium chloride, sodium chloride, lithium chloride, potassium sulfate, sodium carbonate, sodium sulfite, lithium sulfate, potassium chloride, and sodium sulfate. Conventionally, chloride salts such as sodium chloride are utilized as osmagents. However, it is preferred to avoid the use of chloride salts, because chloride depresses the solubility of sertraline. As discussed above, the choice of suitable sugars is restricted due to the reactivity of sertraline.

The sertraline-containing composition 14 may further include solubility-enhancing agents or solubilizers that promote the aqueous solubility of the drug, present in an amount ranging from about 0 to about 30 wt % of the sertraline-containing composition. Solubilizers useful with sertraline include organic acids and organic acid salts, partial glycerides, i.e., less than fully esterified derivatives of glycerin, including glycerides, monoglycerides, diglycerides, glyceride derivatives, polyethylene glycol esters, polypropylene glycol esters, polyhydric alcohol esters, polyoxyethylene ethers, sorbitan esters, polyoxyethylene sorbitan esters, and carbonate salts. Such solubilizers are disclosed more fully in commonly assigned pending U.S. patent application Ser. No. 09/380,897, the disclosure of which is incorporated herein by reference.

A preferred class of solubilizers is organic acids. Since sertraline is a base which is solubilized by protonation, and since its solubility in an aqueous environment of pH 5 or higher is reduced, and reaches an extremely low value by pH 7.5 (as in the colon), it is believed that addition of an organic acid to the dosage form for delivery to the use environment with sertraline assists in solubilization and hence absorption of sertraline. Even a slight decrease in the pH of the aqueous solution at high pH results in dramatic increases in the solubility of sertraline. In addition to simply lowering the pH, the presence of organic acids and their conjugate bases also raises the solubility at a given pH if the conjugate base salt of sertraline has a higher solubility than sertraline chloride. Organic acids can also promote stability during storage prior to introduction to a use environment due to their tendency to maintain sertraline in a protonated state.

There are a variety of factors to consider when choosing an appropriate organic acid for use as a solubilizer with sertraline in a bi-layer dosage form. The acid should not interact adversely with sertraline, should have high water solubility, should provide good manufacturing properties to aid tableting, and should form a sertraline salt that has a high solubility relative to sertraline chloride. In addition, in order to lower the pH of the use environment, it is desired that the acid have a high number of equivalents of acid per gram. This is especially important in the dosage forms of the present invention where the mass of each excipient must be kept at a minimum.

Accordingly, it has been found that a preferred subset of organic acids meeting such criteria consists of citric, succinic, fumaric, adipic, malic and tartaric acids. The table below gives properties of these organic acids. Of these, fumaric and succinic are especially preferred when a high ratio of equivalents of acid per gram is desired. In addition, citric, malic, and tartaric acid have the advantage of extremely high water solubility and high osmotic pressure. Succinic acid offers a combination of both moderate solubility and a high acid equivalent per gram value.

Thus, the use of a highly soluble organic acid as solubilizer serves multiple purposes: it improves the solubility of sertraline, particularly when the use environment is at a pH above about 5 to 6; it provides an osmotic pressure differential; it makes the sertraline-containing composition more hydrophilic so that it readily wets; and it acts as a fluidizing agent, lowering the viscosity of the sertraline-containing composition rapidly. Since multiple functions are achievable with this single component, additional space is available for sertraline within the sertraline-containing composition.

Properties of Organic Acid Solubilizing Agents

| Organic Acid | Acid Equivalents (mEq/g) | Water Solubility (mg/mL) |
|---|---|---|
| Fumaric | 17.2 | 11 |
| Succinic | 16.9 | 110 |
| Citric | 15.6 | >2000 |
| Malic | 14.9 | 1750 |
| Adipic | 13.7 | 45 |
| Tartaric | 13.3 | 1560 |

In a preferred embodiment, when sertraline is present as a highly soluble salt form or when a solubilizer is included in the sertraline-containing composition, the sertraline-containing composition also includes a concentration-enhancing polymer. The inventors have found that the initially enhanced concentration of sertraline in solution provided by the highly soluble salt form or by the use of a solubilizer can be maintained by retarding precipitation or conversion of sertraline to a lower solubility form through the use of a concentration-enhancing polymer. This effect may be obtained by simply mixing the concentration-enhanced polymer with the drug. The concentration-enhancing polymer may be present in the sertraline-containing composition in an amount such that the maximum concentration of sertraline in a use environment is at least 1.25-fold the equilibrium concentration of sertraline in the use environment provided by a control dosage form that is free from the concentration-enhancing polymer and comprises an equivalent quantity of sertraline. Thus, for example, where the control provides an equilibrium concentration of 1 mg/mL, the dosage form which includes a concentration-enhancing polymer provides a maximum concentration of at least 1.25 mg/mL. In addition, the concentration-enhancing polymer maintains the concentration of sertraline in the use environment above the equilibrium concentration for a longer period of time than a control dosage form comprising an equivalent quantity of sertraline but that is free from concentration enhancing polymer. In most cases, it is preferred that the weight ratio of sertraline to concentration-enhancing polymer be greater than 0.05 and less than 2.5. To maximize delivery and dissolution of sertraline in this embodiment, it is desirable for both the highly-soluble sertraline salt form and the concentration-enhancing polymer to have small particle sizes, preferably, less than 20 $\mu$m and more preferably less than 5 $\mu$m in size.

The concentration-enhancing polymer should be inert in the sense that it does not chemically react with sertraline in an adverse manner, and should have at least some solubility in aqueous solution at the physiologically relevant pHs of 1 to 8. Almost any neutral or ionizable polymer that has an aqueous solubility of at least 0.1 mg/mL over at least a portion of the pH range 1–8 is suitable. Suitable concentration-enhancing polymers include ionizable and non-ionizable cellulosic polymers, such as cellulose esters, cellulose ethers, and cellulose esters/ethers; and vinyl polymers and copolymers having substituents selected from the group consisting of hydroxyl, alkylacyloxy, and cyclicamido, such as polyvinyl pyrrolidone, polyvinyl alcohol, copolymers of polyvinyl pyrrolidone and polyvinyl acetate. Particularly preferred polymers include HPMCAS, HPMC, HPMCP, CAP, CAT, and PVP. Concentration-enhancing polymers are discussed in commonly assigned pending U.S. provisional patent application No. 60,171,84, titled "Pharmaceutical Compositions Providing Enhanced Drug Concentrations" filed Dec. 23, 1999, the relevant portions of which are herein incorporated by reference.

The sertraline-containing composition may also include an antioxidant in an amount ranging from 0 to 1 wt % of the sertraline-containing composition. Surprisingly, it has been found that sertraline in the presence of PEO reacts and decomposes over time. The mechanism has been determined to involve the oxidation of PEO. As PEO is oxidized, peroxides are formed that react with sertraline. Indeed, many PEO products, such as those manufactured by Union Carbide Corporation, contain antioxidants to improve stability. However, the antioxidants included in these products are often volatile and are removed or deactivated while manufacturing the dosage form so that peroxides still build up to an unacceptable level. Accordingly, an antioxidant in addition to any that may be present in the PEO is preferably included within the sertraline-containing composition to prevent the oxidation of PEO, which in turn prevents the chemical breakdown of sertraline by minimizing peroxide reactions therewith. Suitable antioxidants include butylated hydroxy toluene (BHT), butylated hydroxyanisole (BHA), vitamin E and ascorbyl palmitate. Note that in some formulations, antioxidants such as BHT can lead to discoloration of the dosage form. In these cases, the amount of antioxidant used should be minimized so as to prevent discoloration.

Finally, the sertraline-containing composition may also include other conventional excipients known to be useful in the pharmaceutical arts, such as those that promote stability, tableting or processing of the dosage form. Such excipients may include fillers, binders, tableting aids and lubricants. Exemplary binders include HPC, HPMC, MC, HEC and PVP. Exemplary tableting aids include microcrystalline cellulose. Exemplary lubricants include metallic salts of acids such as aluminum stearate, calcium stearate, magnesium stearate, sodium stearate, and zinc stearate.

The amounts of the various excipients are chosen as required to allow satisfactory release of sertraline from the dosage form. Sertraline may comprise from about 20 to about 80 wt % of the sertraline-containing composition, but preferably comprises between about 30 and about 70 wt %, and most preferably comprises from about 40 to about 60 wt %. Because a small dosage form is desired, particularly when the sertraline dose is high, higher amounts of sertraline are preferred. However, above about 55 wt % sertraline the drug release profile of the dosage form may in some cases not be optimum. The water-swellable polymer(s) may take up nearly the remainder of the sertraline-containing composition, and may comprise from about 25 to about 99 wt % of the non-sertraline material in the sertraline-containing layer. However, when other water-soluble components such as fluidizing agents, solubilizers, and/or concentration-enhancing polymers are present the water-swellable polymer(s) may comprise only about 25 to about 60 wt % of the non-sertraline components of the sertraline-containing layer. Amounts of the various excipients are as discussed above.

The sertraline, water-swellable polymer(s), and other excipients are mixed together to form a homogeneous mixture. It has been found that direct blending of ingredients, that is, without prior granulation, yields a mixture with poor flow and poor uniformity. Such properties make mass production of tablets difficult. Thus, granulation of at least a portion of the drug layer materials is preferred. In addition, it has been determined that dry granulation via roller compaction followed by milling yields a product that has poor flow and compression properties. Accordingly, wet-granulation is preferably used to prepare at least a portion of the sertraline-containing composition prior to compression. Such granulating processes preferably incorporate a binder such as HPC, HPMC, MC, HEC or PVP.

The solvent used in connection with wet granulation must be chosen with care. Because neutral, (e.g., the free-base form of sertraline) or amorphous sertraline is very reactive, it is desired to maintain sertraline in the crystalline salt form. Accordingly, a solvent must be chosen which minimizes dissolution of sertraline to prevent it from dissolving and then precipitating as reactive forms of sertraline. Another reason for maintaining the crystalline form of sertraline during granulation is to prevent the formation of multiple polymorphs. Nevertheless, the solvent must be capable of dissolving, or at least swelling, at least a portion of the other excipients, particularly the binder, such as HPC or HPMC. It has been found that the preferred solvent choice for wet granulation is water or a mixture of alcohols and water. The lower alcohol may be any $C_1$ to $C_4$ alcohol, such as methanol, ethanol, propanol, isopropanol, or butanol in its various isomers. Preferably, the solvent is a mixture of isopropanol and water. Particularly good results have been obtained by using a mixture of 85 wt % isopropanol and 15 wt % water.

Wet-granulation is preferably followed by wet-milling to eliminate lumps or aggregated granules. The granulated particles are then preferably oven-dried (e.g., in a tray drier) and dry-milled. Alternatively, the granulation particles are dried using fluidized bed or microwave dryers. Granulated materials are generally milled so that greater than 98% of the material passes a 850-μm size screen. As discussed above, the size of the granules obtained dictates the preferred molecular weight of PEO used in the sertraline-containing composition. In general, smaller granules are more easily entrained so that 200,000 molecular weight PEO performs well. These granule size requirements are necessitated by the low water solubility and hydrophobicity of sertraline, as well as the poor flow and compressibility of sertraline. The smaller granules also lead to improved content uniformity and a composition that does not separate. In some cases, particularly when PEO is added to the sertraline following granulation and where following milling a significant fraction of sertraline-containing granules exceeds 425 μm, it has been found that it is desirable to use PEO with a molecular weight of about 300,000 daltons or greater.

In order to provide satisfactory tableting, the sertraline-containing composition should be milled to achieve good compression and flow. Generally, flow improves with increasing size of the granules and tablet hardness generally improves with decreasing granule size. It has been found that for sertraline combined with the excipients described above that a granule size between about 150 and about 450 μm yield the best compromise in these properties.

WATER-SWELLABLE COMPOSITION

Referring again to FIG. 1, the dosage form further comprises a water-swellable composition 16. The water-swellable composition 16 comprises a water-swellable polymer that expands in response to the imbibition of water into the core 12 so as to cause extrusion of the sertraline-containing composition out of the port(s) 20. A suitable water-swellable polymer is PEO having a molecular weight of from 3,000,000 to 8,000,000 daltons. Other water-swellable polymers may be used, such as sodium starch glycolate and sodium croscarmellose and mixtures of each of these with PEO.

Because of the desire to maximize the amount of sertraline relative to other excipients within the dosage form, the amount of water-swellable composition should be decreased relative to the amount of sertraline-containing composition. To do so, the water-swellable polymer in the water-swellable composition must be capable of providing sufficient expansion even when present in only small amounts. Accordingly, a preferred subset of water-swellable polymers includes sodium starch glycolate sold under the trade name EXPLOTAB, and sodium croscarmellose sold under the trade name AC-DI-SOL. These water-swellable polymers may be used alone or as mixtures with PEO. One advantage is that they have a high degree of swelling even in the absence of an osmagent and they allow reduction in the mass of the water-swellable composition.

When the water-swellable polymer is only PEO, the water-swellable composition may also comprise an osmagent. The osmagent may be present in an amount from 0 to 40 wt % of the water-swellable composition. Typical classes of suitable osmagents are water-soluble salts, sugars, organic acids, and other low-molecular-weight organic compounds that are capable of imbibing water to thereby effect an osmotic pressure gradient across the barrier of the surrounding coating. Typical useful salts include magnesium sulfate, magnesium chloride, calcium chloride, sodium chloride, lithium chloride, potassium sulfate, sodium carbonate, sodium sulfite, lithium sulfate, potassium chloride, and sodium sulfate. Conventionally, chloride salts such as sodium chloride are utilized as osmagents. However, it is preferred to avoid the use of such chloride salts, because chloride depresses the solubility of sertraline. As discussed above in connection with the sertraline-containing composition, the choice of suitable sugars is restricted due to the reactivity of sertraline.

In one preferred embodiment, the water-swellable composition is substantially free from an osmotically effective agent, meaning that there is either an insufficient amount of osmagent present or that any osmagent present has insufficient solubility so that the osmotic pressure of the water-swellable layer does not exceed that of the use environment, a condition necessary for the osmotically driven delivery mechanism. By osmotic pressure is meant the pressure calculated from thermodynamic principles using the van't Hoff equation. In order for the dosage form to provide satisfactory release of sertraline in the absence of an osmagent in the water-swellable composition, and when the water-swellable polymer is only PEO, the dosage form should have a high water permeability coating, described below. Particularly when the water-swellable composition is substantially free of an osmotically effective agent the water swellable composition should preferably contain a substantial quantity, typically at least 10 wt % and preferably at least 50 wt %, of a highly swelling polymer such as sodium starch glycolate or sodium croscarmellose.

The ability to release sertraline relatively quickly using a bi-layer dosage form without the inclusion of an osmagent in the water-swellable composition is a surprising result, since conventional wisdom in the art has held that osmagents should be included in the swelling layer to achieve good performance. This provides several advantages. One advantage is that the space and weight otherwise occupied by osmagent may be devoted to sertraline, thus increasing the amount of sertraline within the dosage form. Alternatively, the overall size of the dosage form may be decreased. In addition, eliminating the osmagent further allows for a more simply manufactured dosage form, since the water-swellable composition may omit the step of including an osmagent.

The water-swellable composition may also optionally include solubilizers such as those discussed above in connection with the sertraline-containing layer. Solubilizers may be present in an amount of 0 to 40 wt % of the water-swellable composition. In a preferred embodiment, the solubilizer is an organic acid with a high solubility in water. Examples include citric, malic, succinic, and tartaric acids. In a more preferred embodiment, the dosage form delivers at least a portion of the organic acid 5 hours after ingestion of the dosage form, roughly equating to arrival in the lower portion of the GI tract. Preferably, the dosage form delivers at least 5 wt % of the solubilizer, and preferably at least 20 wt %, and more preferably at least 30 wt %, to the use environment from 8 to 24 hours after introduction of the dosage form to the use environment. Inclusion of the organic acid in the water-swellable composition rather than in the sertraline-containing composition delays the delivery of the organic acid to the use environment. The organic acid may be included in both layers as well. Such delayed delivery of the organic acid tends to enhance the concentration of organic acid in the GI fluid in the vicinity of the tablet, which in turn can lead to enhanced sertraline concentrations. This is particularly important when a substantial amount of sertraline is to be delivered to the colon.

Another restriction on the type and amount of acid used in the dosage form is the need to prevent acid induced damage or irritation to the GI tract. An in vitro test for whether the dosage form will likely cause GI irritation involves measuring the pH of the plume of entrained drug and acid extruded from the delivery port when the dosage form is placed in an unbuffered saline solution. The pH can be measured using pH paper or a pH meter. The pH is measured at several times during the course of the drug delivery. The pH that does not induce irritation depends on the rate at which acid is delivered and the solubility of the acid. To assure that this dosage form will not result in GI irritation, the pH of the plume must always be above about 3.0, and it is particularly preferred (especially for high doses) to be above a pH of about 3.5–4.0.

The water-swellable composition may also optionally contain a colorant. The purpose of the colorant is to allow identification of the drug-containing side of the core face for purposes of providing the delivery port 20, such as by drilling through the coating. However, because sertraline is a base, the colorant should be selected so as not to promote its oxidation. Accordingly, colorants containing iron (III), such as ferric oxide, should be avoided. Acceptable colorants include, but are not limited to, Red Lake No. 40, FD & C Blue 2 and FD & C Yellow 6. Preferred colorants are FD & C Blue 2 and Yellow 6.

For those embodiments containing PEO as the water-swellable polymer in the water-swellable composition, the water-swellable composition may also contain an antioxidant like that discussed above in connection with the discussion of the sertraline-containing composition, such as BHT, vitamin E, BHA, or ascorbyl palmitate. The antioxidant may be present in an amount ranging from 0 to 1 wt % of the water-swellable composition.

Water-swellable composition 16 may also include other conventional pharmaceutically useful excipients such as a binder, including HPC, HPMC, HEC, MC, and PVP, a tableting aid, such as microcrystalline cellulose, and a lubricant such as magnesium stearate. However, it is preferred that such other excipients comprise a minor portion of the water-swellable composition, and most preferred that the water-swellable composition contain as few excipients as possible in the least amount possible.

The water-swellable composition is prepared by mixing the water-swellable polymer and the other excipients to form a uniform blend. To obtain a uniform blend, it is desirable to either wet granulate or dry blend ingredients that have similar particle sizes using the same types of processes listed above for the sertraline-containing composition. For example, blending of powdered sodium chloride with PEO yields a more homogeneous blend than use of granular sodium chloride. When the water-swellable polymer is PEO, it is desirable to use a wet granulation process, wherein the solvent is an alcohol with 1 to 4 carbon atoms, preferably ethanol. When other water-swellable polymers are used, dry granulation may be employed or wet granulation where water has been found to be a suitable solvent. After granulation, the material is typically dried using processes known in the art, examples of which are tray dryers, fluid-bed dryers, and microwave dryers. Following drying, the granules are typically milled to a size of about 150 to about 425 µm.

TABLETING

The core 12 is prepared by first placing a mixture of the sertraline-containing composition 14 into a tablet press and then leveling the mixture by gentle compression. The water-swellable composition 16 is then placed on top of the sertraline-containing composition 14 and compressed in order to complete formation of the core 12. Alternatively, the water-swellable composition can be placed into the tablet press first, followed by the sertraline-containing composition.

The respective amounts of sertraline-containing composition 14 and water-swellable composition 16 are chosen to provide satisfactory sertraline release. When it is desired to provide a large sertraline dose in a relatively small dosage size, i.e., less than 1 g, and preferably less than 800 mg and more preferably even smaller, it is desired to maximize the amount of sertraline-containing composition and minimize the amount of water-swellable composition, while still obtaining good release performance. Surprisingly, the dosage forms of the present invention allow extremely large amounts of the sertraline-containing composition relative to the water-swellable composition. Conventionally, with low-solubility, hydrophobic drugs such as sertraline it is thought that large amounts of water-swellable polymer and high levels of osmagent in the water-swellable composition are required to achieve acceptable release rates and low residual. In the dosage forms of the present invention, when the water-swellable polymer in the water-swellable composition is only PEO, the sertraline-containing composition may comprise from about 50 to about 85 wt % of the core, and preferably from about 60 to about 70 wt %. These values correspond to a weight ratio of the sertraline-containing composition to water-swellable composition of from 1 to about 5.7, and preferably from about 1.5 to about 2.3. When all or part of the water-swellable polymer in the water-swellable composition comprises sodium starch glycolate or croscarmellose sodium, the sertraline-containing composition may comprise from 50 to 90 wt % of the core, and preferably from about 75 to about 85 wt %. Those values correspond to the weight ratio of the sertraline-containing composition to water-swellable composition of from 1 to 9, and preferably from 3 to 5.7.

Figure 2:
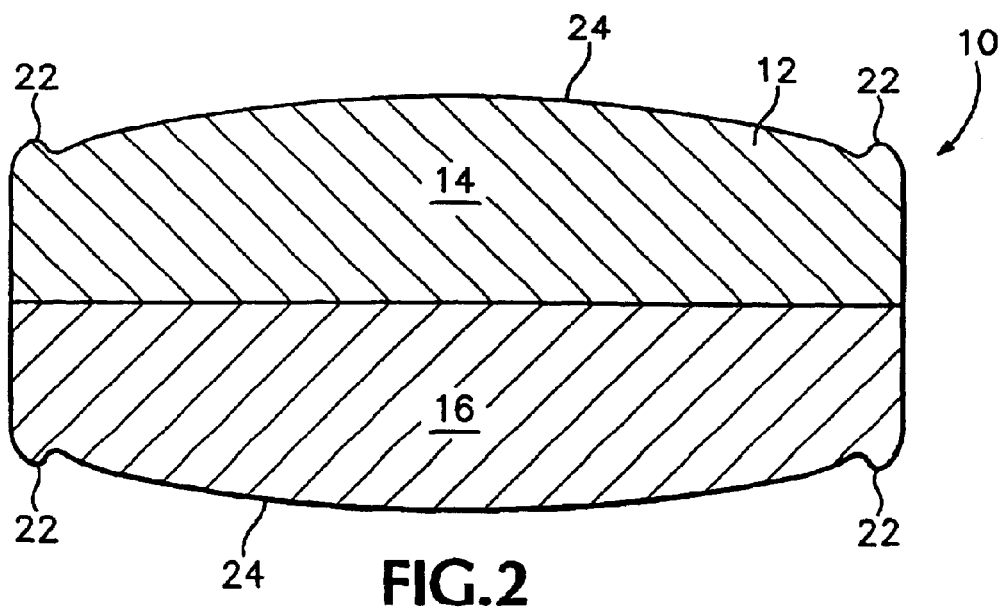
FIG. 2 is a schematic cross section of an exemplary dosage form illustrating the phenomenon designated as "crowning."

Preferably, the particle size of the materials used in the water-swellable composition are relatively small in order to facilitate core compression. It has been found that the core 12 must be compressed under a relatively narrow range of pressures and compression times in order to avoid "crowning." Crowning occurs during compression of the sertraline-containing composition and water-swellable composition when material from the water-swellable composition flows between the spaces in various die surfaces. The result, as illustrated in FIG. 2, is a core that has circumferential ridges 22 around the faces 24. Ridges 22 tend to create stresses in coating 18 (not shown in FIG. 2), and may even cause the coating to fail as pressure increases inside the core as the core imbibes water through the coating.

The amount of pressure that can be used to adequately compress the core while avoiding crowning will depend on the diameter and weight of the core, as well as the type of press used to form the core. It has been found that for 7/32-inch tooling and a core weight of about 100 to about 150 mg, compression that results in a tablet hardness of 1 to 7 Kiloponds (Kp), more preferably 3 to 5 Kp should be used to avoid crowning. Likewise, for 11/32-inch tooling and a core weight of about 350 to about 450 mg, compression that results in a tablet hardness of 3 to 10, more preferably 5 to 7 Kp, should be used, while for 7/16-inch tooling and a core weight of about 650 mg to 750 mg, compression that results in a tablet hardness of 6 to 12, more preferably 8 to 10 Kp, should be used. Thus, in general, the pressure used to adequately compress the core while avoiding crowning should be selected so that the hardness (H measured in Kp) of the core falls in the range described by the following expression:

$$35D^2-1 \leq H \leq 35D^2+6,$$

where D is the diameter in inches of the tooling used for making the core. It should be noted that when the faces of the tablet are not circular the maximum cross-sectional surface area of the tablet face in square inches multiplied by $(4/\pi)$ can be substituted for D in this expression.

Because this hardness is relatively low, small particle sizes are preferred for the various ingredients of the water-swellable composition to facilitate proper compression. Otherwise, given the relatively low hardness values, the core 12 may disintegrate prior to or during coating. Thus, where NaCl is included as an osmagent, the NaCl may be micronized, such as in a jet mill or by spray-drying, to reduce particle size. Preferably, when NaCl is used as an osmagent it has a size distribution such that less than 10 wt % of the NaCl has a particle size greater than about 425 $\mu$m. Similarly, the PEO in the water-swellable composition may be screened so that the particle size distribution is such that less than 10 wt % has a particle size greater than about 425 $\mu$m.

The absolute value of the diameter and height of the tablets of the present invention can vary over a wide range. However, the aspect ratio, defined as the tablet diameter divided by the tablet height, must be closely controlled. Specifically the aspect ratio should not exceed a value of about 1.5, and preferably not in excess of 1.4. Larger aspect ratios lead to incomplete release of sertraline from the tablet during the time the tablet is in the use environment.

THE COATING

Following formation of the core 12, coating 18 is applied. The coating should have high water permeability and a high strength, while at the same time be easily fabricated and applied. High water permeability is required to permit water to enter the core in sufficient volume. In the case of sertraline, when it is desirable to deliver a high dose, sertraline's low solubility makes it necessary to use a high permeability coating to achieve the desired sertraline release profile while keeping the tablet acceptably small. High strength is required to ensure the coating does not burst when the core swells as it imbibes water, leading to an uncontrolled delivery of the core contents to the use environment. Finally, the coating must have high reproducibility and yield.

It is essential that the coating 18 have at least one delivery port 20 in communication with the interior and exterior of the coating for delivery of the sertraline-containing composition. Furthermore, the coating must be non-dissolving and non-eroding during release of the sertraline-containing composition, generally meaning that it be water-insoluble, such that sertraline is substantially entirely delivered through the delivery port(s) 20, in contrast to delivery via permeation through the coating.

As mentioned, the coating 18 is highly water permeable to allow rapid imbibition of water into core 12 to cause a rapid release of the sertraline-containing composition 14. By "rapid release" is meant both the time prior to the onset of release and the time required for release of a majority of the sertraline is relatively short. A measure of the water permeability of the coating can be made by conducting the following experiment. Finished tablets are placed in an open container which is in turn placed in an environmental chamber held at a constant temperature of 40° C. and a constant relative humidity of 75%. The initial rate of weight gain of the dry tablets, determined by plotting the weight of the tablets versus time, divided by the surface area of the tablets yield a value termed "water flux (40/75)." The "water flux (40/75)" value for a tablet has been found to be a useful relative measure of the water permeabilities of tablet coatings. The inventors have found that for the sertraline tablets of the present invention the coating 18 should preferably have a "water flux (40/75)" value of at least $1.0 \times 10^{-3}$ $\mu$m/hr·cm$^2$, and preferably at least $1.1 \times 10^{-3}$ $\mu$m/hr·cm$^2$, more preferably at least $1.3 \times 10^{-3}$ $\mu$m/hr·cm$^2$.

The inventors have further found that coatings with these characteristics can be obtained using hydrophilic polymers such as plasticized and unplasticized cellulose esters, ethers, and ester-ethers. Particularly suitable polymers include cellulose acetate (CA), cellulose acetate butyrate (CAB), and ethyl cellulose (EC). A preferred set of polymers are cellulose acetates having acetyl contents of 25 to 42%. A particularly preferred polymer is CA having an acetyl content of 39.8%, and specifically, CA 398–10 (Eastman Fine Chemicals, Kingsport, Tenn.). CA 398-10 is reported to have an average molecular weight of about 40,000 daltons. Another preferred CA having an acetyl content of 39.8% is high molecular weight CA having an average molecular weight greater than about 45,000, and specifically, CA 398-30 (Eastman Fine Chemical) which is reported to have an average molecular weight of 50,000 daltons. The high molecular weight CA provides superior coating strength, which allows thinner coatings and thus higher permeability.

Coating is conducted in conventional fashion by first forming a coating solution and then coating by dipping, fluidized bed coating, or preferably by pan coating. To accomplish this, a coating solution is formed comprising the polymer and a solvent. Typical solvents useful with the cellulosic polymers above include acetone, methyl acetate, ethyl acetate, isopropyl acetate, n-butyl acetate, methyl isobutyl ketone, methyl propyl ketone, ethylene glycol monoethyl ether, ethylene glycol monoethyl acetate, methylene dichloride, ethylene dichloride, propylene dichloride, nitroethane, nitropropane, tetrachloroethane, 1,4-dioxane, tetrahydrofuran, diglyme, and mixtures thereof. A particularly preferred solvent is acetone. The coating solution typically contains 3 to 15 wt % of the polymer, preferably 5 to 10 wt %, most preferably 7 to 10 wt %.

The coating solution may also include pore-formers or non-solvents in any amount as long as the polymer remains soluble at the conditions used to form the coating and as long as the coating remains water permeable and has sufficient strength. Pore-formers and their use in fabricating coatings are described in U.S. Pat. Nos. 5,698,220 and 5,612,059, the pertinent disclosures of which are incorporated herein by reference. The term "pore former," as used herein, refers to a material added to the coating solution that has low or no volatility relative to the solvent such that it remains as part of the coating following the coating process but that is sufficiently water swellable or water soluble such that, in the aqueous use environment it provides a water-filled or water-swollen channel or "pore" to allow the passage of water, thereby enhancing the water permeability of the coating. Suitable pore formers include polyethylene glycol ("PEG"), PVP, and PEO. Particularly preferred pore formers are PEG having a molecular weight from 1000 to 8000 daltons and water. A particularly preferred PEG is PEG having a molecular weight of 3350 daltons. The inventors have found that to obtain a combination of high water permeability and high strength when PEG is used as a pore former, the weight ratio of CA:PEG should range from about 6.5:3.5 to about 9:1.

The addition of a non-solvent such as water to the coating solution results in exceptional performance. By "non-solvent" is meant any material added to the coating solution that substantially dissolves in the coating solution and reduces the solubility of the coating polymer or polymers in the solvent. In general, the function of the non-solvent is to impart porosity to the resulting coating. As described below, porous coatings have higher water permeability than an equivalent weight of a coating of the same composition that is not porous and this porosity, when the pores are gas filled, as is typical when the non-solvent is volatile, is indicated by a reduction in the density of the coating (mass/volume). Although not wishing to be bound by any particular mechanism of pore formation, it is generally believed that addition of a non-solvent imparts porosity to the coating during evaporation of solvent by causing the coating solution to undergo liquid—liquid phase separation prior to solidification. The suitability and amount of a particular candidate material can be evaluated for use as a non-solvent by progressively adding the candidate non-solvent to the coating solution until it becomes cloudy. If this does not occur at any addition level up to about 50 wt % of the coating solution, it generally is not appropriate for use as a non-solvent. When clouding is observed, termed the "cloud point," an appropriate level of non-solvent for maximum porosity is the amount just below the cloud point. For acetone solutions comprising 7 wt % CA and 3 wt % PEG, the cloud point is at about 23 wt % water. When lower porosities are desired, the amount of non-solvent can be reduced as low as desired.

Suitable non-solvents are any materials that have appreciable solubility in the solvent and that lower the coating polymer solubility in the solvent. The preferred non-solvent depends on the solvent and the coating polymer chosen. In the case of using a volatile polar coating solvent such as acetone, suitable non-solvents include water, glycerol, and $C_1$ to $C_4$ alcohols such as methanol or ethanol.

When using CA 398-10, exemplary coating solution weight ratios of CA:PEG 3350: water are 7:3:5, 8:2:5, and 9:1:5, with the remainder of the solution comprising a solvent such as acetone. Thus, for example, in a solution having a weight ratio of CA:PEG 3350: water of 7:3:5, CA comprises 7 wt % of the solution, PEG 3350 comprises 3 wt % of the solution, water comprises 5 wt % of the solution, and acetone comprises the remaining 85 wt %.

Coatings formed from these preferred coating solutions are generally porous. By "porous" is meant that the coating in the dry state has a density less than the density of the same material in a nonporous form. By "nonporous form" is meant a coating material formed by using a coating solution containing no non-solvent, or the minimal amount of non-solvent required to produce a homogeneous coating solution. Preferably, the coating has a dry-state density that is less than 0.9 times, and more preferably less than 0.75 times, the density of the same material in a nonporous form. The dry-state density of the coating can be calculated by dividing the coating weight (determined from the weight gain of the tablets before and after coating) by the coating volume (calculated by multiplying the coating thickness, as determined by optical or scanning electron microscopy, by the tablet surface area). The porosity of the coating is one of the factors that leads to the combination of high water permeability and high strength of the coating.

The weight of the coating around the core depends on the composition and porosity of the coating, but generally should be present in an amount ranging from 3 to 30 wt %, preferably 8 to 25 wt %, based on the weight of the uncoated core. However, a coating weight of at least about 8 wt %, and preferably at least 12 wt %, is preferred for sufficient strength for reliable performance.

While porous coatings based on CA, PEG, and water described above result in excellent results, other pharmaceutically acceptable materials could be used in the coating so long as the coating has the requisite combination of high water permeability, high strength, and ease of fabrication and application. Further, such coatings may be dense, porous, or "asymmetric," having one or more dense layers and one or more porous layers such as those disclosed in U.S. Pat. Nos. 5,612,059 and 5,698,220, the pertinent disclosures of which are incorporated herein by reference.

The coating 18 must also contain at least one delivery port 20 in communication with the interior and exterior of the coating to allow for release of the drug-containing composition to the exterior of the dosage form. The delivery port can range in size from about the size of the drug particles, and thus could be as small as 1 to 100 microns in diameter and may be termed pores, up to about 5000 microns in diameter. The shape of the port may be substantially circular, in the form of a slit, or other convenient shape to ease manufacturing and processing. The port(s) may be formed by post-coating mechanical or thermal means or with a beam of light (e.g., a laser), a beam of particles, or other high-energy source, or may be formed in situ by rupture of a small portion of the coating. Such rupture may be controlled by intentionally incorporating a relatively small weak portion into the coating. Delivery ports may also be formed in situ by erosion of a plug of water-soluble material or by rupture of a thinner portion of the coating over an indentation in the core. Delivery ports may be formed by coating the core such that one or more small regions remains uncoated. In addition, the delivery port can be a large number of holes or pores that may be formed during coating, as in the case of asymmetric membrane coatings of the type disclosed in U.S. Pat. Nos. 5,612,059 and 5,698,220, the disclosures of which are incorporated by reference. When the delivery pathways are pores there can be a multitude of such pores that range in size from 1 $\mu$m to greater than 100 $\mu$m. During operation, one or more of such pores may enlarge under the influence of the hydrostatic pressure generated during operation. The number of delivery ports 20 may vary from 1 to 10 or more. At least one delivery port should be formed on the side of coating that is adjacent to the drug-containing composition, so that the drug-containing composition will be extruded out of the delivery port by the swelling action of the water-swellable composition. It is recognized that some processes for forming delivery ports may also form holes or pores in the coating adjacent to the water-swellable composition. In aggregate, the total surface area of core exposed by delivery ports is less than 5%, and more typically less than 1%.

The coating may optionally include a port 30 in communication with the water-swellable composition 16. Such a delivery port does not alter the sertraline release characteristics of the dosage form, but may provide manufacturing advantages. It is believed that the water-swellable compositions, such as those containing PEO with a molecular weight between 3,000,000 and 8,000,000 daltons, are too viscous to appreciably exit the port 30. In dosage forms wherein the delivery ports are drilled either mechanically or by laser, the tablet must be oriented so that at least one delivery port is formed in the coating adjacent to the sertraline-containing composition 14. A colorant within the water-swellable composition is used to orient the core dosage form during the drilling step in manufacture. By providing a delivery port 20 on both faces of the dosage form, as illustrated in FIG. 1, the need to orient the dosage form may be eliminated and the colorant may be removed from the water-swellable composition 16. This reduces the overall size of the dosage form, and eliminates a potential catalyst (the colorant) of the degradation of sertraline.

In an alternative embodiment, the dosage form 10 may contain sertraline within or around the coating 18. One way to form a sertraline-containing coating is to form a slurry or solution of sertraline and polymer and spray-coat the tablets with this slurry. Such a dosage form would provide an immediate release of sertraline into the use environment. Such an immediate release may be desired where the sertraline-containing core does not deliver sertraline sufficiently rapidly. To reduce side effects from the immediate release, following introduction into the environment of use, such sertraline-containing coating dosage forms should deliver no more than 25 wt % of the total amount of sertraline within the first 2 hours. Thus, the sertraline in or around the coating 18 is present in low amounts so the release profiles of the dosage forms of the present invention are obtained.

It has been found that once the dosage form has been coated, it should be kept in a dry atmosphere. Exposure to high humidity levels leads to intermingling of the sertraline-containing composition and the water-swellable composition, which can alter the release rate and release profile of the dosage form.

Other features and embodiments of the invention will become apparent from the following examples which are given for illustration of the invention rather than for limiting its intended scope.

Because of the importance of the release of sertraline in the hours 2 through 12 following ingestion, unless otherwise specified, all references in the examples to release rates of drug are to wt % of sertraline averaged over the period beginning at the end of the second hour and ending at the end of the twelfth hour. Thus, for example, if 20 wt % sertraline is released by the end of hour 2 and 90 wt % is released by the end of hour 12, then the "release rate" is (90−20)÷10 or 7.0 wt %/hour.

EXAMPLE 1

Exemplary dosage forms of the present invention were made with a bi-layer core geometry of the type depicted in FIG. 1, consisting of a layer of a sertraline-containing composition and a layer of a water-swellable composition.

The sertraline-containing composition comprised the following materials: 22.8 wt % sertraline HCl, 71.7 wt % PEO with an average molecular weight of 200,000 daltons (Polyox WSR N80), 5.0 wt % HPMC (METHOCEL K3 LV Prem, a tablet binder), and 0.5 wt % of the lubricant, magnesium stearate. To form the sertraline-containing composition, the ingredients (without the magnesium stearate) were blended for 20 minutes in a Turbula mixer. This blend was screened through a 0.065-inch size screen, then blended again for 20 minutes. Next, magnesium stearate was added and the materials were blended again for 4 minutes.

The water-swellable composition comprised the following materials: 65.0 wt % PEO with an average molecular weight of 5,000,000 daltons (Polyox WSR Coagulant), 29.3 wt % sodium chloride, 5.1 wt % HPMC (METHOCEL K3 LV Prem.), and 0.6 wt % magnesium stearate. To form the water-swellable composition, the ingredients (without the magnesium stearate) were blended 20 minutes in a Turbula mixer, then blended again for 4 minutes with the magnesium stearate.

The sertraline-containing composition and the water-swellable composition were formed into a bi-layer core using direct compression. A portion of the sertraline-containing composition (490 mg) was placed in an f-press with a standard round concave $15/32$-inch die, then gently leveled with the upper punch. A portion of the water-swellable composition (245 mg) was placed on top of the layer of sertraline-containing composition and compressed. The compression distance between the upper and lower punches on the f-press was adjusted until the hardness of the resulting core measured 15 Kp. The resulting bi-layer core weighed 735 mg and contained a total of 15.2 wt % sertraline HCl, 47.8 wt % PEO 200,000, 5.0 wt % HPMC, 0.5 wt % magnesium stearate, 21.7 wt % PEO 5,000,000, and 9.8 wt % sodium chloride. Assays of these tablets confirmed 112 mg of sertraline HCl, or 100 mgA of active sertraline.

The cores were then coated with a high water permeability coating in a Vector LDCS-20 pan coater. The coating solution contained CA 398-10, PEG 3350, water, and acetone in a weight ratio of 7/3/5/85. Heated drying air at 40 cfm was adjusted to maintain the pan coater outlet temperature at 25° C. Nitrogen at 20 psi was used to atomize the coating solution from the spray nozzle, with a nozzle-to-bed distance of 2 inches. The pan tumbled at 30 rpm. The final dry coating weight amounted to 12.9 wt % of the weight of the core. One 900-$\mu$m delivery port was hand-drilled on the drug-containing face of the tablet. The total weight of the coated tablet was 830 mg.

An in vitro residual test was performed. Tablets were placed in a stirred USP type 2 dissoette flask containing 900 ml of a solution of simulated gastric buffer (10 mM HCl, 100 mM NaCl, pH 2.0, 261 mOsm/kg) for 2 hours, and then transferred to a stirred USP type 2 dissoette flask containing 900 ml of a solution of simulated intestinal buffer (6 mM $KH_2PO_4$, 64 mM KCl, 35 mM NaCl, pH 7.2, 210 mOsm/kg). In both flasks, the dosage form was placed in a wire support to keep the tablet off the bottom of the flask so that all surfaces were exposed to the solution, and the solutions were stirred using paddles rotating at 50 rpm. At certain time intervals, a single tablet was removed and placed in a recovery solution (50/50 wt/wt % ethanol/water, pH 3) in a stirred flask at ambient temperature to dissolve the sertraline remaining in the tablet. Residual sertraline was analyzed by HPLC using a Phenomenex Ultracarb 5 ODS 20 column. The mobile phase consisted of 35 vol. % TEA-acetate buffer (3.48 mL triethanolamine and 2.86 mL glacial acetic acid in 1 L HPLC-grade $H_2O$) in acetonitrile. Sertraline concentration was calculated by comparing UV absorbance at 230 nm to the absorbance of known sertraline standards. The amount remaining in the tablets was subtracted from the initial amount of sertraline in the tablets (100 mgA) to obtain the amount released at each time interval. Results are shown in Table 1 and are summarized in Table D.

TABLE 1

| Time (hours) | Drug Release (wt %) |
|---|---|
| 0 | 0 |
| 1 | 2 |
| 2 | 19 |
| 4 | 51 |
| 8 | 98 |
| 12 | 99 |
| 18 | 99 |
| 24 | 99 |

The data show that 19 wt % of the sertraline was released within 2 hours and 98 wt % within 8 hours. This indicates that the tablets of the present invention resulted in rapid release of sertraline to a use environment, yet kept the amount delivered during the first two hours to a reasonably low value. Furthermore, after 24 hours, virtually all sertraline had been released. Observations of the tablets during the release test indicated that the coating was able to withstand the swelling of the PEO-based core and remained intact for the duration of the test.

EXAMPLES 2A –2D

These examples demonstrate the inventive delivery of sertraline from a tablet of the present invention, while varying the percentage of sertraline in the sertraline-containing composition from 20 wt % to 50 wt %. Tablets were made as in Example 1, with the exceptions noted in Tables A, B, and C, and discussed as follows: tablets for Example 2A were coated with a weight ratio of CA/PEG in the coating solution of 8/2 (instead of 7/3), and the water-swellable composition was wet granulated; tablets for Example 2B had a delivery port of 900 μm (the same size used for Example 1), while Examples 2A, 2C, and 2D had delivery ports of 700 μm. The sertraline-containing composition and water-swellable composition for each of these examples were combined in a ratio of 2:1 sertraline-containing composition:water-swellable composition, as in Example 1.

Tablets for Examples 2A and 2D were evaluated using a direct test. Tablets were placed into a stirred USP type 2 dissoette flask containing 900 ml of a receptor solution. The receptor solution was USP sodium acetate buffer (27 mM acetic acid and 36 mM sodium acetate, pH 4.5). Samples were taken at certain time intervals using a VanKel VK8000 autosampling dissoette with automatic receptor solution replacement. Tablets were placed in a wire support as above, paddle height was adjusted, and the dissoette flasks stirred at 50 rpm at 37° C. Periodically, the autosampler removed a sample of the receptor solution, and the concentration of sertraline in the receptor was analyzed directly by HPLC.

Tablets for Example 2C were also evaluated using the direct test using a receptor solution of 88 mM NaCl. Tablets for Example 2B were evaluated using the residual test described in Example 1. Results are shown in Table 2 and summarized in Table D.

TABLE 2

| Example | Time (hours) | Drug Released (wt %) |
|---|---|---|
| 2A | 0 | 0 |
| | 1 | 0 |
| | 2 | 4 |
| | 4 | 30 |
| | 6 | 58 |
| | 8 | 85 |
| | 10 | 97 |
| | 12 | 97 |
| | 16 | 99 |
| | 20 | 98 |
| | 24 | 99 |
| 2B | 0 | 0 |
| | 1 | 7 |
| | 2 | 25 |
| | 4 | 65 |
| | 8 | 97 |
| | 12 | 98 |
| | 18 | 98 |
| | 24 | 98 |
| 2C | 0 | 0 |
| | 1 | 0 |
| | 2 | 5 |
| | 4 | 20 |
| | 6 | 41 |
| | 8 | 65 |
| | 10 | 82 |
| | 12 | 88 |
| | 14 | 90 |
| | 16 | 93 |
| | 18 | 94 |
| | 20 | 95 |
| | 22 | 95 |
| | 24 | 95 |
| 2D | 0 | 0 |
| | 1 | 0 |
| | 2 | 8 |
| | 4 | 40 |
| | 6 | 60 |
| | 8 | 72 |
| | 10 | 73 |
| | 12 | 75 |
| | 14 | 75 |
| | 16 | 74 |
| | 18 | 76 |
| | 20 | 77 |
| | 22 | 75 |
| | 24 | 77 |

The data show that as the percentage of sertraline in the sertraline-containing composition was increased, the rate of sertraline release remained high. Furthermore, Examples 2A, 2C, and 2D showed time lags of less than 2 hours, while Example 2B showed a time lag of less than 1 hour. The amount of drug remaining in the tablets after 24 hours was outstanding for Examples 2A, 2B, and 2C at 5 wt % or less, and 23 wt % for Example 2D, a level that may be acceptable in some cases. These examples show that successful delivery of sertraline from dosage forms of this invention was obtained, even for delivery of high percentages of the total drug-containing composition.

EXAMPLES 3A–3C

For this set of examples, tablets were made containing PEO of varying molecular weights. The tablets were made as in Example 1 with the exceptions given in Tables A, B, and C. Key differences were as follows. The Example 3A tablet sertraline-containing composition contained PEO of two molecular weights: 30 wt % PEO 200,000 and 30 wt % PEO 300,000. The Example 3B tablets contained 29 wt % PEO 600,000, as well as 30 wt % of the fluidizing agent xylitol (XYLITAB 200) and 5 wt % sodium starch glycolate (EXPLOTAB) in the sertraline-containing composition. The Example 3C tablets contained 54 wt % PEO 300,000. For tablets used in Example 3C, the sertraline-containing composition was formed by combining drug and binder, wet-granulating with water, then adding PEO 300,000. Tablets for a comparative Control 3D, were made the same way as those for Example 3C, substituting PEO 200,000 for the PEO 300,000.

The tablets for Examples 3A and 3B were evaluated using the residual test described in Example 1; and tablets of Examples 3C and Control 3D were tested in USP sodium acetate buffer using the direct test described in Example 2. Results are shown in Table 3 and summarized in Table D.

TABLE 3

| Dosage Form Example | Time (hours) | Drug Release (wt %) |
| --- | --- | --- |
| 3A | 0 | 0 |
|  | 1 | 0 |
|  | 2 | 16 |
|  | 4 | 49 |
|  | 8 | 97 |
|  | 12 | 99 |
|  | 18 | 98 |
|  | 24 | 99 |
| 3B | 0 | 0 |
|  | 1 | 1 |
|  | 2 | 15 |
|  | 4 | 47 |
|  | 8 | 80 |
|  | 12 | 90 |
|  | 18 | 95 |
|  | 24 | 87 |
| 3C | 0 | 0 |
|  | 1 | 0 |
|  | 2 | 0 |
|  | 4 | 7 |
|  | 6 | 23 |
|  | 8 | 37 |
|  | 10 | 55 |
|  | 12 | 78 |
|  | 16 | 96 |
|  | 20 | 98 |
| Control 3D | 0 | 0 |
|  | 1 | 0 |
|  | 2 | 2 |
|  | 4 | 12 |
|  | 6 | 25 |
|  | 8 | 42 |
|  | 10 | 57 |
|  | 12 | 58 |
|  | 16 | 61 |
|  | 20 | 62 |
|  | 24 | 63 |

The data show that satisfactory sertraline delivery was obtained with each of the dosage forms of Examples 3A, 3B, and 3C, containing widely differing PEO molecular weights. Note in particular in Example 3B, that a mixture of high molecular weight PEO (600,000) and a non-reducing sugar, xylitol, can be substituted for low molecular weight PEO (200,000 or 300,000) with no loss in drug delivery performance. It was noted that the tablet of Example 3B had superior processing properties upon milling and compression relative to the examples that had high PEO levels and no xylitol. Comparing Example 3C and Control 3D shows that in some cases, PEO molecular weight can be very significant. For those tablets (Control 3D) made using wet granulation of the sertraline-containing composition before addition of PEO, the lower molecular weight PEO (200,000) did not maintain a sufficiently high viscosity to entrain the larger granulated sertraline particles for delivery through the port. In Example 3C, using a higher molecular weight PEO (300,000) resulted in a much higher percentage of sertraline delivered relative to Control 3D. These results will be discussed further as part of the granulation discussion in Examples 4A–4D.

EXAMPLES 4A–4D

These examples demonstrate the effects of sertraline-containing composition processing variables on tablet performance. Control 3D and Examples 4A and 4B show the effect of sertraline-containing composition granulation with varying amounts of PEO included in the granulation. Example 4C shows the effect of sertraline granulation particle size. Examples 4B and 4D compare low-shear aqueous granulation of the sertraline-containing composition to a high-shear granulation using an 85/15 weight ratio of isopropyl alcohol (IPA)/water. Tables A, B, and C summarize the formulations used in these Examples.

As discussed above, in Control 3D, the tablets were made by wet granulation (with water at low-shear) of the sertraline-containing composition without PEO 200,000 present during the granulation step. After granulation of the drug, the PEO was added to the sertraline-containing composition, and bi-layer tablets were made as in Example 1.

In Example 4A, the wet granulation (with water at low-shear) was performed wherein 10 wt % of the total amount of PEO 200,000 used in the sertraline-containing composition (54 wt % total, see Table A) was included during the granulation step. The remaining 90 wt % of the PEO 200,000 was added to the sertraline-containing composition after the granulation step.

In Example 4B, all of the PEO 200,000 used in the sertraline-containing composition (54 wt %, see Table A) was included during the granulation step.

The tablets of Example 4C were processed in the same way as the tablets of Control 3D (wet granulation without PEO 200,000), except that the granulation was milled to reduce particle size before blending the milled granulation with the PEO 200,000 and magnesium stearate to form the sertraline-containing composition.

In Example 4D, the drug, PEO 200,000, and binder were wet-granulated using a high-shear granulator using an 85/15 (wt/wt) IPA/water mixture.

As indicated in Tables A, B, and C, each tablet from all four of these examples (4A–4D) and Control 3D contained 40 wt % drug in the sertraline-containing composition, and had one 700 μm delivery port drilled in the drug-containing face. During the fabrication of these tablets, it was noted that granulation with 85/15 (wt/wt) IPA/water (Example 4D) was preferred in that the sertraline showed no signs of dissolution during granulation and the granules produced were more easily milled (i.e., they were not as hard) relative to the granulation with water only (Example 4B).

The tablets were dissolution-tested in USP sodium acetate buffer, using the direct test method. The results for Examples 4A–D are shown in Table 4.

TABLE 4

| Example | Time (hours) | Drug Release (wt %) |
| --- | --- | --- |
| 4A | 0 | 0 |
|  | 1 | 0 |
|  | 2 | 7 |
|  | 4 | 27 |

TABLE 4-continued

| Example | Time (hours) | Drug Release (wt %) |
|---|---|---|
| | 6 | 50 |
| | 8 | 74 |
| | 10 | 94 |
| | 12 | 96 |
| | 16 | 97 |
| | 20 | 98 |
| 4B | 0 | 0 |
| | 1 | 1 |
| | 2 | 14 |
| | 4 | 41 |
| | 6 | 68 |
| | 8 | 94 |
| | 10 | 100 |
| | 12 | 99 |
| | 14 | 101 |
| | 16 | 102 |
| | 18 | 102 |
| | 20 | 101 |
| | 22 | 101 |
| | 24 | 100 |
| 4C | 0 | 0 |
| | 1 | 0 |
| | 2 | 4 |
| | 4 | 24 |
| | 6 | 46 |
| | 8 | 70 |
| | 10 | 91 |
| | 12 | 94 |
| | 16 | 96 |
| | 20 | 97 |
| 4D | 0 | 0 |
| | 2.1 | 5 |
| | 4.1 | 24 |
| | 6.1 | 46 |
| | 8.1 | 68 |
| | 10.1 | 89 |
| | 18.1 | 92 |
| | 24.1 | 89 |

These results show that having no PEO 200,000 in the drug granulation (control 3D) limits drug entrainment and delivery, resulting in a low release rate (5.6 wt %/hr) and only 42 wt % release of the drug within 8 hours. However, including 10 wt % of the PEO 200,000 (Example 4A) or 100 wt % of the PEO 200,000 (Example 4B) in the granulation resulted in high release rates (8.9 and 8.5 wt %/hr, respectively), and acceptable release of drug within 8 hours (74 wt % and 94 wt %, respectively). It is postulated that wet-granulating a portion of the PEO 200,000 with the drug resulted in better disintegration of granules and entrainment of the drug particles during delivery, resulting in faster and more complete release.

Example 4C shows that acceptable performance was obtained by milling a granulation made without the PEO 200,000 so that the granulation had an average size less than about 400 μm. This dosage form resulted in a high release rate (9.0 wt %/hr) and an acceptable release of drug within 8 hours (70 wt %).

Example 4D demonstrates that excellent sertraline release was obtained using a high-shear wet granulation process using IPA/water, where all sertraline-containing composition ingredients except magnesium stearate were granulated together. In addition, it was noted that this granulation method produced a material that was more easily milled and compressed (tableted).

EXAMPLES 5A–5C

These examples demonstrate release of a solubilizing acid with sertraline. In Examples 5A, 5B, and 5C, dosage forms of the present invention were made wherein the sertraline-containing composition or the water-swellable composition included a solubilizing acid selected from citric acid and fumaric acid. These tablets were made as in Example 1, with the exceptions noted in Tables A, B, and C. In Example 5A, the sertraline-containing composition contained 15 wt % citric acid. In Example 5B, the sertraline-containing composition contained 7 wt % fumaric acid. In Example 5C, both the sertraline-containing composition and the water-swellable composition contained 15 wt % citric acid.

The tablets were dissolution-tested in USP sodium acetate buffer, using the direct test. The results for Examples 5A–C are shown in Tables 5.1 and 5.2 and are summarized in Table D.

TABLE 5.1

| Example | Time (hours) | Drug Release (wt %) |
|---|---|---|
| 5A | 0 | 0 |
| | 1 | 0 |
| | 2 | 3 |
| | 4 | 23 |
| | 6 | 47 |
| | 8 | 69 |
| | 10 | 88 |
| | 12 | 91 |
| | 16 | 82 |
| | 20 | 92 |
| | 24 | 92 |
| 5B | 0 | 0 |
| | 1 | 0 |
| | 2 | 9 |
| | 4 | 31 |
| | 6 | 57 |
| | 8 | 79 |
| | 10 | 92 |
| | 12 | 96 |
| | 16 | 96 |
| | 20 | 96 |

TABLE 5.2

| | Time | (wt % released) | |
|---|---|---|---|
| Example | (hours) | Drug | Citric Acid |
| 5C | 0 | 0 | 0 |
| | 1 | 0 | 0 |
| | 2 | 6 | 9 |
| | 4 | 24 | 28 |
| | 6 | 46 | 47 |
| | 8 | 65 | 62 |
| | 10 | 81 | 76 |
| | 12 | 94 | 84 |
| | 16 | 96 | 89 |
| | 20 | 96 | 93 |

The results of Examples 5A–5C show that high rates of sertraline release (8.8, 8.7, and 8.8 wt %/hr, respectively) were obtained when the dosage form included a solubilizing acid. Comparison with dosage forms that do not contain the solubilizing acid (e.g., Example 2C) shows that the presence of solubilizing acids did not substantially change the release profile for the drug.

The results of Example 5C show that the citric acid was released at about the same rate as the sertraline (7.5 wt %/hr for citric acid, 8.8 wt %/hr for sertraline). In addition, citric acid was released at all times while sertraline was released. During the release test of Examples 5A–C, the receptor solution in close proximity to the tablets had a pH of about 3, indicating that including organic acids in the dosage form leads to a locally lower pH. Since lower pH generally leads to greater sertraline solubility, it is anticipated that the inclusion of a solubilizing acid will lead to a higher concentration of dissolved sertraline and, as a result, increased bioavailability.

EXAMPLE 6A

Example 6A demonstrates the effect of particle size on delivery of sertraline. Tablets for this example were prepared as in Example 2C, except that sertraline HCl was jet-milled to reduce particle size, and the sertraline-containing composition was granulated with water (see Tables A, B, and C for exact tablet formulations). Control 6B was made using jet-milled sertraline HCl, but the sertraline-containing composition was not granulated with water. Before jet-milling, the sertraline HCl had an average particle size of about 20 μm. After jet-milling, the average particle size was about 5 μm.

Tablets for Example 6A and Control 6B were dissolution-tested using the direct test in sodium acetate buffer and 88 mM NaCl solution, respectively. All samples were taken directly from the receptor solutions and analyzed by HPLC. The results for Example 6A and Control 6B are shown in Table 6 and summarized in Table D.

TABLE 6

| Example | Time (hours) | Drug Release (wt %) |
|---|---|---|
| 6A | 0 | 0 |
|  | 1 | 0 |
|  | 2 | 9 |
|  | 4 | 33 |
|  | 6 | 56 |
|  | 8 | 81 |
|  | 10 | 98 |
|  | 12 | 99 |
|  | 16 | 99 |
|  | 20 | 100 |
| Control 6B | 0 | 0 |
|  | 1 | 0 |
|  | 2 | 1 |
|  | 4 | 11 |
|  | 6 | 27 |
|  | 8 | 43 |
|  | 10 | 52 |
|  | 12 | 60 |
|  | 14 | 60 |
|  | 16 | 61 |
|  | 18 | 61 |
|  | 20 | 61 |
|  | 22 | 60 |
|  | 24 | 61 |

The data show that the rate of sertraline release for the dosage form made with the jet-milled sertraline (Example 6A) was excellent at 9.0 wt %/hr with 99 wt % release within 12 hours. This performance was similar to the same dosage form made using the non jet-milled sertraline with wet granulation (Example 4B) and the same dosage form made using non-jet-milled sertraline with a dry-blended sertraline-containing composition (Example 2C). The data also show that when the jet-milled sertraline was dry-blended to form the sertraline-containing composition (Control 6B), the rate of release was low (5.9 wt %/hr), and the amount released at 12 hours was low (60 wt %).

The jet-milled sertraline HCl was observed to agglomerate more than that which was not jet-milled. In the case of Example 6A, these agglomerated sertraline particles were reduced in size via wet-granulation, while the sertraline particles in Control 6B remained relatively large. Apparently, these larger sertraline particles were not sufficiently entrained in the sertraline-containing composition by the PEO 200,000, and sertraline delivery was incomplete.

EXAMPLES 7A–7B

These examples demonstrates the delivery of different pharmaceutically acceptable salt forms of sertraline from dosage forms of the present invention. Different sertraline salt forms (such as acetate, lactate or aspartate) may be more bioavailable than sertraline HCl due to their higher aqueous solubility and faster dissolution rate. Tablets for Example 7A were made as in Example 2B, except that sertraline lactate was used instead of sertraline HCl (see Tables A, B, and C for details of the tablet formulation). These tablets were dissolution-tested using the residual test described in Example 1.

Tablets of Example 7B were made as in Example 2D with the exceptions noted in Tables A, B, and C. The sertraline-containing layer contained 49.2 wt % sertraline lactate. These tablets were dissolution-tested using a sodium acetate buffer solution in the direct test. The results for both 7A and 7B are presented in Table 7 and summarized in Table D.

TABLE 7

| Example | Time (hours) | Drug Release (wt %) |
|---|---|---|
| 7A | 0 | 0 |
|  | 1 | 0 |
|  | 2 | 13 |
|  | 4 | 36 |
|  | 6 | 68 |
|  | 8 | 82 |
|  | 12 | 87 |
|  | 18 | 82 |
|  | 24 | 86 |
| 7B | 0 | 0 |
|  | 1 | 0 |
|  | 2 | 3 |
|  | 4 | 18 |
|  | 6 | 48 |
|  | 8 | 73 |
|  | 10 | 83 |
|  | 12 | 87 |
|  | 16 | 88 |
|  | 20 | 90 |

These data show that satisfactory sertraline release was obtained with sertraline lactate. This demonstrates that the dosage forms of the present invention can deliver sertraline as various pharmaceutically acceptable salt forms.

EXAMPLE 8

This example discloses the use of salt as a fluidizing agent. Example 3B showed that including the non-reducing sugar xylitol (which also acts as an osmagent) in the sertraline-containing composition resulted in acceptable performance. Examples 5A, 5B, and 5C also showed that including the solubilizing acid citric acid (which also acts as an osmagent) in the formulation resulted in acceptable performance.

To further demonstrate the use of osmagents in the dosage form, tablets for Example 8 were made as in Example 2C, except that 7.5 wt % of sodium chloride was included in the sertraline-containing composition (see Tables A, B, and C for details of the tablet formulation). These tablets were tested in USP sodium acetate buffer in the direct test described in Example 2. The results are presented in Table 8 below and summarized in Table D.

TABLE 8

| Time (hours) | Drug Release (wt %) |
|---|---|
| 0 | 0 |
| 1 | 0 |
| 2 | 10 |
| 4 | 32 |
| 6 | 55 |
| 8 | 76 |
| 10 | 82 |
| 12 | 83 |
| 16 | 83 |
| 20 | 84 |

The data show that inclusion of the osmagent NaCl in the sertraline-containing composition resulted in a high rate of sertraline release (7.3 wt %/hr) and 83 wt % sertraline released within 12 hours. This was similar to the release profile obtained without an osmagent included in the sertraline-containing composition (Example 2C).

EXAMPLE 9

This example discloses the use of small excipient particle sizes. Excipient particle size can affect tablet content uniformity, sertraline release rate, and residual sertraline. Tablets for Example 9 were made as in Example 2C, except that powdered sodium chloride was used in the water-swellable composition instead of granular sodium chloride (see Tables A, B, and C for the specific tablet formulation). (For powdered sodium chloride, 25% of the mass had a particle size greater than 300 μm, while for granular sodium chloride 89.1% of the mass had a particle size greater than 300 μm.) These tablets were dissolution-tested in USP sodium acetate buffer using the direct test (with samples taken directly from the receptor solution), and analyzed by HPLC as described in Example 2. The results are presented in Table 9 below and summarized in Table D.

TABLE 9

| Time (hours) | Drug Release (wt %) |
|---|---|
| 0 | 0 |
| 1 | 0 |
| 2 | 6 |
| 4 | 40 |
| 6 | 72 |
| 8 | 91 |
| 10 | 99 |
| 12 | 101 |
| 16 | 102 |
| 20 | 102 |
| 24 | 102 |

These results show that the rate of sertraline release was high (9.5 wt %/hr), with virtually all of the sertraline being released within 12 hours (actual assay was 101 wt % release). These results show that using powdered NaCl resulted in faster and more complete sertraline release relative to that obtained when using granulated NaCl (Example 2C), which had a release rate of 8.3 wt %/hr and 88 wt % drug release within 12 hours. This may be due to more rapid wetting of the water-swellable composition due to the high surface area and uniform distribution of the sodium chloride. In addition, use of powdered NaCl improved the manufacturing process by allowing the PEO, binder (METHOCEL), and NaCl of the water-swellable composition to be mixed more uniformly, and retain its uniformity, that is, it does not separate.

EXAMPLES 10A–10C

These examples demonstrate the effect of varying the amount of sodium chloride in the water-swellable composition. Example 10A tablets were prepared as in Example 2B, except that no sodium chloride was added to the water-swellable composition (see Tables A, B, and C for tablet formulations). Example 10B tablets were prepared as in Example 10A (without sodium chloride), except that EXPLOTAB and the tableting aid microcrystalline cellulose (PROSOLV 90) were used in the water-swellable composition instead of PEO 5,000,000. Example 10C tablets were prepared as in Example 2C, except that only 20 wt % sodium chloride was added to the water-swellable composition instead of 30 wt %.

Tablets for Examples 10A and 10B were tested as in Example 1 using the residual test, and tablets for Example 10C were tested in USP sodium acetate using the direct test. Samples were analyzed using HPLC, and the results are shown in Table 10 and summarized in Table D.

TABLE 10

| Example | Time (hours) | Drug Release (wt %) |
|---|---|---|
| 10A | 0 | 0 |
|  | 1 | 10 |
|  | 2 | 18 |
|  | 4 | 48 |
|  | 8 | 67 |
|  | 12 | 78 |
|  | 20 | 94 |
|  | 24 | 92 |
| 10B | 0 | 0 |
|  | 1 | 3 |
|  | 2 | 17 |
|  | 4 | 49 |
|  | 8 | 70 |
|  | 12 | 84 |
|  | 20 | 88 |
|  | 24 | 92 |
| 10C | 0 | 0 |
|  | 1 | 0 |
|  | 2 | 7 |
|  | 4 | 28 |
|  | 6 | 52 |
|  | 8 | 79 |
|  | 10 | 100 |
|  | 12 | 101 |
|  | 16 | 102 |
|  | 20 | 103 |
|  | 24 | 103 |

These results show that removing the NaCl from the water-swellable composition (Example 10A) resulted in only a slightly slower rate of drug release (6.0 wt %/hr) as compared to a similar formulation containing 30 wt % NaCl in the water-swellable composition (Example 2B) which had a release rate of 7.3 wt %/hr. In addition, only 78 wt % of the drug was released within 12 hours, as compared with Example 2B, in which 98 wt % of the drug was released within 12 hours. This small reduction in sertraline release rate was probably primarily due to the slightly thicker coating on the tablets of Example 10A (15.2 wt %) relative to Example 2B (13.0 wt %), showing that contrary to conventional practice, acceptable sertraline release can be obtained without inclusion of an osmagent as long as a high permeability coating is used.

Replacing the PEO in the water-swellable composition with EXPLOTAB and PROSOLV (Example 10B) resulted in excellent performance, despite the absence of an osmagent in the water-swellable layer, showing a release rate of 6.7 wt %/hr and 84 wt % of drug released within 12 hours.

The release rate observed for Example 10C (9.4 wt %/hr) was slightly faster than in Example 2C (8.3 wt %/hr) showing that the amount of sodium chloride in the water-swellable composition can be decreased from 30 wt % to 20 wt % with no adverse effect on sertraline release rate.

EXAMPLES 11A–11B

These examples demonstrate the effect of the ratio of the mass of the sertraline-containing composition to the mass of the water-swellable composition on the performance of dosage forms of the present invention. It is desirable that this ratio be as high as possible to minimize tablet size and/or to maximize the amount of sertraline that can be delivered in a single tablet.

Tablets for Example 11A were made as in Example 2C (see Tables A, B, and C for tablet formulations), except that the ratio of sertraline-containing composition to water-swellable composition was 4.6 instead of the 2 ratio used in Example 2C. In Example 11B, the sertraline-containing composition to water-swellable composition ratio was 4. In addition, in Example 11B, the water-swellable composition included EXPLOTAB and PROSOLV instead of PEO and NaCl, and five 900 μm delivery ports were drilled in the drug-containing face. Other differences between the tablets are given in Tables A, B, and C.

Tablets for Example 11A were dissolution-tested in USP sodium acetate using the direct test and tablets for Examples 11B were dissolution-tested using the residual test as described in Example 1. Samples were analyzed using HPLC, and the results are shown in Table 11 and summarized in Table D.

TABLE 11

| Example | Time (hours) | Drug Release (wt %) |
|---|---|---|
| 11A | 0 | 0 |
|  | 1 | 0 |
|  | 2 | 8 |
|  | 4 | 29 |
|  | 6 | 48 |
|  | 8 | 64 |
|  | 10 | 75 |
|  | 12 | 82 |
|  | 16 | 90 |
|  | 20 | 94 |
| 11B | 0 | 0 |
|  | 2 | 22 |
|  | 4 | 45 |
|  | 8 | 79 |
|  | 14 | 92 |
|  | 20 | 94 |

The data in Table 11 show that dosage forms having a fairly high ratio of sertraline-containing composition to water-swellable composition still achieve good release profiles. The tablets of Example 11A with a sertraline-containing composition to water-swellable composition ratio of 4.6 showed an acceptable release rate of 7.4 wt %/hr. This can be compared to tablets made with a sertraline-containing composition to water-swellable composition ratio of 2 (Example 2C), which had a release rate of 8.3 wt %/hr.

The tablets of 11B showed particularly good performance, having essentially no time lag (22 wt % sertraline released during the first 2 hours) and very high drug loading, the sertraline-containing composition comprising 80 wt % of the tablet core and sertraline itself comprising about 32 wt % of the total drug core.

EXAMPLES 12A–12B

These examples demonstrate the effects of the granulation particle size of the sertraline-containing composition excipients and the effect of compression force used to form the core on core hardness. A sertraline-containing composition having a formulation similar to that in Example 2C (see Table A) was formed into tablets (without a water-swellable composition).

For Example 12A, the ingredients were first combined without the magnesium stearate and the PEO 200,000 in a Twinshell v-blender and blended for 5 minutes. Next, the sertraline-containing composition was granulated in a planetary mixer using water as the granulating solvent. The sertraline-containing composition was tray-dried in a 40° C. convection oven. The sertraline-containing composition was then milled in a Fitzpatrick L1A mill at 2500 rpm with knives forward and a 0.033-inch size screen installed. Next, the PEO 200,000 was added and blended for 10 minutes. Next, the magnesium stearate was added and the sertraline-containing composition was blended for 4 minutes.

For Example 12B, the sertraline-containing composition ingredients were granulated with isopropyl alcohol as the solvent in a high shear granulator.

The compositions of Examples 12A and 12B were sieved for particle-size analysis. Results are shown in Table 12.1.

Tablets were made from the compositions of Examples 12A and 12B on an instrumented Kilian T100 with 7/16-inch standard round concave tooling. Tablets were made with various compression forces and tablet hardness tested. Results are shown in Table 12.2.

TABLE 12.1

| Example | Sieve Size (μm) | Weight Fraction (wt %) |
|---|---|---|
| 12A | >850 | 0.8 |
|  | 425–849 | 17.6 |
|  | 250–424 | 23.2 |
|  | 180–249 | 16.6 |
|  | 150–179 | 7.2 |
|  | 106–149 | 12.0 |
|  | <106 | 23.2 |
| 12B | >850 | 0.8 |
|  | 425–849 | 49.4 |
|  | 250–424 | 31.2 |
|  | 180–249 | 9.5 |
|  | 150–179 | 2.2 |
|  | 106–149 | 3.3 |
|  | <106 | 3.6 |

TABLE 12.2

| Example | Compression Force (kN) | Tablet Hardness (Kp) |
|---|---|---|
| 12A | 2.2 | 3.7 |
|  | 6.5 | 10.1 |
|  | 12.9 | 14.3 |
|  | 21.0 | 16.2 |
|  | 29.8 | 17.5 |
|  | 36.6 | 18.1 |
| 12B | 2.5 | 0.7 |
|  | 6.2 | 3.8 |
|  | 11.6 | 5.1 |
|  | 18.7 | 5.6 |
|  | 31.0 | 5.9 |
|  | 37.3 | 6.0 |

From these examples it can be seen that as the weight fraction of large particle sizes was reduced and the weight fraction of the smaller particle sizes was increased (Example 12A), a higher tablet hardness was achieved for a given compression force when compared with the formulation with the larger particle size (Example 12B).

EXAMPLES 13A–13B

The tablets of these examples show delivery of sertraline from dosage forms of the present invention with different tablet aspect ratios. The aspect ratio is defined as the tablet diameter divided by the tablet height.

Tablets for Example 13A were made as in Example 2C, with the exceptions noted in Tables A, B, and C. In Example 13A, the total core weight was 110 mg and 7/32-inch tooling was used to form the tablet. For Control 13B, tablets were made as in Example 13A, except the tablet press tooling was changed from 7/32 inch (Example 13A) to VS inch (Control 13B) to obtain tablets with different aspect ratios. The drug layer for Control 13B tablets was dry blended. Tablets from Example 13A and Control 13B contained 25 mgA of sertraline. The aspect ratios are shown below.

TABLE 13.1

| Example | Tablet Aspect Ratio (d/h) |
| --- | --- |
| 13A | 1.21 |
| Control 13B | 1.55 |

Example 13A and comparative Control 13B tablets were tested using USP sodium acetate receptor solution, using the direct test method. The samples were taken directly from the receptor solution, and analyzed by HPLC as described in Example 1. The results are shown in Table 13.2 below.

TABLE 13.2

| Dosage Form Example | Time (hours) | Drug Release (wt %) |
| --- | --- | --- |
| 13A | 0 | 0 |
|  | 2 | 25 |
|  | 4 | 61 |
|  | 6 | 92 |
|  | 8 | 94 |
|  | 10 | 94 |
|  | 18 | 95 |
|  | 24 | 96 |
| Control 13B | 0 | 0 |
|  | 1 | 0 |
|  | 2 | 16 |
|  | 4 | 59 |
|  | 6 | 63 |
|  | 8 | 65 |
|  | 10 | 65 |
|  | 12 | 67 |
|  | 16 | 65 |
|  | 20 | 66 |
|  | 24 | 67 |

The tablet with a high aspect ratio (Control 13B) had a low rate of drug release (5.1 wt %/hr), while tablets of the present invention (Example 13A) had an acceptable release rate of 7.0 wt %/hr. In addition, after 24 hours, the tablets with the higher 1.55 aspect ratio (Control 13B) had only released 67 wt % of the drug, is while tablets of the present invention with the lower 1.21 aspect 1.21 ratio (Example 13A) released 96 wt % of the drug. Thus, too high a tablet aspect ratio can lead to poor sertraline release.

EXAMPLES 14A–14B

These examples demonstrate the effects of coating variables on sertraline release from dosage forms of this invention.

Tablets for Examples 14A and 14B were made as in Example 2C (see Tables A, B, and C for tablet compositions), except that the ratio of CA/PEG in the coating solution and the coating thickness were varied. These tablets were tested in sodium acetate buffer using the direct test, and the results are shown in Table 14. For Examples 14A and 14B the time required to deliver 80 wt % of the drug was measured for each coating weight.

TABLE 14.1

| Example | Coating Weight (wt % of tablet) | Time to 80 wtA % Drug Release (hrs) |
| --- | --- | --- |
| 14A | 8.1 | 5.5 |
| Coating | 11.0 | 5.7 |
| CA/PEG = 7/3 | 14.2 | 6.5 |
|  | 15.2 | 7.1 |
|  | 18.2 | 7.9 |
|  | 18.8 | 8.5 |
|  | 20.8 | 9.2 |
| 14B | 12.1 | 11.8 |
| Coating | 14.3 | 13.1 |
| CA/PEG = 8/2 | 16.3 | 14.5 |
|  | 17.7 | 15.2 |
|  | 19.9 | 16.9 |
|  | 23.3 | 19.4 |

These data show that increasing the coating weight increased the time required to release 80 wt % of the drug from the tablet. It is postulated that this is because as the amount of coating increased, the coating was made thicker and the water permeability of the coating was reduced. As a result, water entered the tablet more slowly, leading to a reduced rate of swelling of the swellable component of the tablet, and to a correspondingly reduced rate of sertraline release.

The data also show that increasing the ratio of PEG to CA in the coating decreased the time required to release 80 wt % of the sertraline from the tablet for a given coating weight. It is postulated that this is because the water permeability of the coating material was higher as the ratio of PEG in the coating increased.

These data demonstrate that the desired sertraline release profile can be obtained by adjusting the coating thickness and composition.

EXAMPLES 15A–15E

These examples show the effect of varying the size and number of delivery ports on sertraline release from dosage forms of this invention.

Example 15A was made as in Example 2C (see Tables A, B, and C for details of the tablet formulations), with one 700 μm delivery port drilled on the sertraline-containing composition tablet face. Example 15B was made as in Example 2C, with one 700 μm port drilled on both tablet faces. Examples 15C, 15D, and 15E were made as in Example 2C, with one delivery port each, of 700 μm, 900 μm, and 2000 μm, drilled on the sertraline-containing composition tablet face. These tablets were dissolution tested in USP sodium acetate using the direct test and analyzed by HPLC as described in Example 2. The results are shown in Table 15.1 and 15.2, and summarized in Table D.

TABLE 15.1

| Example | Time (hours) | Drug Release (wt %) |
|---|---|---|
| 15A | 0 | 0 |
|  | 1 | 0 |
|  | 2 | 8 |
|  | 4 | 38 |
|  | 6 | 65 |
|  | 8 | 90 |
|  | 10 | 100 |
|  | 12 | 101 |
|  | 16 | 101 |
|  | 20 | 101 |
|  | 24 | 102 |
| 15B | 0 | 0 |
|  | 1 | 0 |
|  | 2 | 6 |
|  | 4 | 33 |
|  | 6 | 62 |
|  | 8 | 83 |
|  | 10 | 96 |
|  | 12 | 100 |
|  | 16 | 102 |
|  | 20 | 101 |
|  | 24 |  |
| 15C | 0 | 0 |
|  | 0.5 | 0 |
|  | 1.0 | 0 |
|  | 1.5 | 0 |
|  | 2.0 | 0.3 |
|  | 2.5 | 3.7 |
|  | 3.0 | 8.3 |
|  | 3.5 | 12.4 |
|  | 4.0 | 16.4 |
| 15D | 0 | 0 |
|  | 0.5 | 0 |
|  | 1.0 | 0 |
|  | 1.5 | 0 |
|  | 2.0 | 2.2 |
|  | 2.5 | 8.2 |
|  | 3.5 | 18.3 |
|  | 4.0 | 23.5 |
| 15E | 0 | 0 |
|  | 0.5 | 0 |
|  | 1.0 | 0 |
|  | 1.5 | 0.1 |
|  | 2.0 | 3.0 |
|  | 2.5 | 8.7 |
|  | 3.0 | 13.3 |
|  | 3.5 | 19.1 |
|  | 4.0 | 25.5 |

TABLE 15.2

| Example | Tablet Hole Size (μm) | Initial Release Rate* |
|---|---|---|
| 15C | 700 | 8.1 |
| 15D | 900 | 10.7 |
| 15E | 2000 | 11.3 |

*wt % over hours 2–4.

Comparison of Examples 15A and 15B show that adding a second delivery port on the second face of the tablet had little effect on tablet performance. Placing delivery ports on both tablet faces can simplify manufacturing and tablet reliability by ensuring that a delivery port is present in the coating face in contact with the sertraline-containing layer without the need to identify which face this is. Comparison of Examples 15C, 15D, and 15E show that the size of the hole had an effect on the initial release rate of the tablet: the larger the delivery port, the faster the initial release of drug. These data show that the number and size of the delivery ports in the tablet can be adjusted to obtain the desired release profile.

EXAMPLE 16

This example demonstrates the delivery of sertraline in the form of a dispersion from a dosage form of the invention. Amorphous solid dispersions of sertraline in polymers were prepared according to procedures described in commonly assigned U.S. patent application Ser. Nos. 09/495,059 and 09/495,061, both filed Jan. 31, 2000, the relevant portions of which are incorporated by reference. These sertraline/polymer dispersions may be incorporated into the sertraline-containing composition of the bi-layer dosage forms of the present invention, using the processing techniques described in the examples above.

For the tablets used in Example 16, the sertraline dispersion was formed by spray-drying a solution containing 0.65 wt % sertraline free base, 0.65 wt % HPMCP 55, 49.35 wt % methanol, and 49.35 wt % acetone. The drug was dissolved in the methanol, and the polymer was dissolved in the acetone, before combining the solutions. The solution was spray-dried using a two-fluid external mix spray nozzle at 1.8 bar at a feed rate of 187 to 211 g/min into the stainless steel chamber of a Niro spray-dryer, maintained at a temperature of 230° C. at the inlet and 72° C. at the outlet.

To form the sertraline-containing composition, the following materials were blended: 41.15 wt % of the above sertraline dispersion (1:1 sertraline free base:HPMCP), 26.75 wt % PEO 600,000, 26.75 wt % XYLITAB 200, 4.33 wt % EXPLOTAB, and 1.02 wt % magnesium stearate. In this process, the sertraline-containing composition ingredients were combined and precompressed, then milled in a co-mill at 1100 rpm with screen size 0.075-inch opening. To form the water-swellable composition, the following materials were blended: 74.66 wt % EXPLOTAB, 24.73 wt % PROSOLV 90, 0.47 wt % magnesium stearate, and 0.14 wt % Red Lake #40. The water-swellable composition ingredients were combined without the magnesium stearate, blended 20 minutes in a Turbula mixer, then blended again for 4 minutes with magnesium stearate. Assays of these tablets confirmed 112 mgA of sertraline. Coating and the drilling of a delivery port were effected as in Example 1.

Release of the sertraline dispersion from the tablets of Example 16 into simulated intestinal buffer was measured, using the residual test and samples were analyzed by HPLC, both as described in Example 1. Results are shown in Table 16.

TABLE 16

| Time (hours) | Drug Release (wt %) |
|---|---|
| 0 | 0 |
| 1 | 7 |
| 2 | 17 |
| 4 | 40 |
| 8 | 68 |
| 12 | 86 |
| 18 | 91 |
| 24 | 86 |

The data demonstrate satisfactory delivery of a dispersion of sertraline from dosage forms of this invention. Delivery of sertraline in the form of a dispersion is expected to enhance the concentration of dissolved sertraline in the GI tract and the bioavailability of sertraline relative to delivery of crystalline sertraline hydrochloride at the same release profile.

EXAMPLES 17A–C

These examples show the effects of the formulation of the coating material on the water permeability of the coating. This example measured the water flux (40/75) value discussed above. Tablet cores were made as in Example 2A, with the exceptions noted in Tables A, B, and C, using 15/32-inch standard round concave tooling, with compression at 13.4 Kp. Thus, each tablet core had an approximate surface area of 4.35 cm$^2$.

Coatings were applied to these cores as in Example 1. Table 17.1 gives the composition of the coating solutions used. Acetone was used as the solvent in all cases.

TABLE 17.1

| Example | Coating Solution Formulation (wt %) | | | Coating Weight per Tablet | |
|---|---|---|---|---|---|
| | CA 398-10 | PEG | Water | mg | wt % |
| 17A | 7 | 3 | 5 | 82 | 11.2 |
| 17B | 8 | 2 | 5 | 84 | 11.4 |
| 17C | 9 | 1 | 5 | 86 | 11.7 |

To determine the water flux (40/75) value, five tablets from each example were placed in a weigh boat and placed into an environmental chamber set at a constant temperature of 40° C. and a constant relative humidity of 75%. Periodically, the tablets were removed and weighed. Table 17.2 recites the data from this experiment.

TABLE 17.2

| Time | Weight of 5 Tablets (gm) | | |
|---|---|---|---|
| (hrs) | Example 17A | Example 17B | Example 17C |
| 0 | 4.0241 | 4.0383 | 4.0703 |
| 0.5 | 4.0491 | 4.0590 | 4.0867 |
| 1 | 4.0611 | 4.0676 | 4.0948 |
| 3 | 4.0882 | 4.0901 | 4.1158 |
| 4 | 4.0943 | 4.0966 | 4.1213 |
| 5 | 4.1025 | 4.1031 | 4.1281 |
| 6 | 4.1082 | 4.1076 | 4.1338 |
| 7 | 4.1119 | 4.1110 | 4.1370 |
| 22 | 4.1338 | 4.1303 | 4.1593 |
| 23 | 4.1374 | 4.1341 | 4.1627 |
| 24 | 4.1406 | 4.1356 | 4.1649 |

The water flux (40/75) values of the coatings were determined by dividing the initial slope obtained by plotting weight versus time by the tablet surface area (for 5 tablets). Table 17.3 shows the results of these calculations using a linear regression fit of the first three data points to determine the initial slope. The data show that the water flux (40/75) values increased as the amount of PEG increased relative to the amount of CA in the coating solution.

TABLE 17.3

| Example | PEG/CA Ratio (by weight) | Water Flux (40/75) (g/hr.cm$^2$) |
|---|---|---|
| 17A | 0.45 | $1.7 \times 10^{-3}$ |
| 17B | 0.25 | $1.4 \times 10^{-3}$ |
| 17C | 0.11 | $1.1 \times 10^{-3}$ |

EXAMPLE 18

This example shows the utility of including a concentration-enhancing polymer and a solubilizer in the sertraline-containing composition. The sertraline-containing composition comprised the following materials: 20 wt % sertraline HCl, 15 wt % tartaric acid (a solubilizer), 20 wt % HPMCAS-LG (a concentration-enhancing polymer), 29 wt % PEO with an average molecular weight of 600,000 daltons (Polyox WSR-205) (a polymeric entraining agent), 15 wt % xylitol (XYLITAB 200) (a fluidizing agent), and 1 wt % of the lubricant, magnesium stearate.

To form the sertraline-containing composition, the ingredients (without the magnesium stearate) were blended for 10 minutes in a Turbula mixer. This blend was wet-granulated using a mortar and pestle with a mixture of isopropyl alcohol and water in a volume ratio of 85:15. The wet-granulated material was dried in a 40° C. oven overnight. The dried granulation was passed through a Fitzpatrick hammer mill, model L1A, at 3000 rpm, and screened through a 0.065-inch screen. This material was blended again in the Turbula mixer for 10 minutes. Next, magnesium stearate was added and the materials were blended for 4 additional minutes.

The water-swellable composition comprised the following materials: 64.4 wt % PEO with an average molecular weight of 5,000,000 (Polyox WSR Coagulant), 30 wt % sodium chloride, 5 wt % HPMC (METHOCEL E5 LV Prem., a tablet binder), 0.1 wt % of a colorant (Red Lake #40), and 0.5 wt % magnesium stearate. To form the water-swellable composition, the ingredients (without the colorant or magnesium stearate) were blended 20 minutes in a Twinshell mixer, then milled using a hammer mill and passed through a 0.098-inch screen. This material was blended again for 20 minutes in a Twinshell mixer. The colorant and magnesium stearate were mixed for 1 minute, and then added to the blend. These ingredients were blended for 4 additional minutes.

The sertraline-containing composition and the water-swellable composition were tableted together using direct compression to form the core. A portion of the sertraline-containing composition (441.5 mg) was placed in an f-press with a standard round concave 7/16-inch die, then gently leveled with the upper punch. A portion of the water-swellable composition (227.5 mg) was placed on top of the layer of sertraline-containing composition and compressed. The compression distance between the upper and lower punches on the f-press was adjusted until the hardness of the resulting core measured 11.4 Kp. The resulting bilayer core weighed 669 mg and contained a total of 13.2 wt % sertraline HCl, 9.9 wt % tartaric acid, 13.2 wt % HPMCAS-LG, 19.1 wt % PEO 600,000, 9.9 wt % xylitol, 0.9 wt % magnesium stearate, 21.9 wt % PEO 5,000,000, 10.2 wt % sodium chloride, 1.7 wt % HPMC, and 0.03 wt % colorant. Assays of these cores showed 82 mg of sertraline HCl, or 73 mgA.

The tablet cores were coated with a high water permeability coating in a Vector LDCS-20 pan-coater. The coating solution contained CA 398-10, polyethylene glycol (PEG 3350), water, and acetone in a weight ratio of 7/3/5/85 (see Table C). Heated drying air at 40 cfm was adjusted to maintain the pan-coater outlet temperature at 25° C. Nitrogen at 20 psi was used to atomize the coating solution from the spray nozzle, with a nozzle-to-bed distance of 2 inches. The pan tumbled at 20 rpm. The final dry coating weight amounted to 20.4 wt % of the weight of the tablet core. One 2 mm hole was laser-drilled on the drug-containing face of the tablet. The total weight of the coated tablet was 805 mg.

An in vitro residual sertraline release test was performed. Tablets were placed in a stirred USP type 2 dissoette flask containing a solution of simulated gastric buffer (10 mM HCl, 100 mM NaCl, pH 2.0, 261 mOsm/kg) for 2 hours, and then transferred to a solution of simulated intestinal buffer (6 mM $KH_2PO_4$, 64 mM KCl, 35 mM NaCl, pH 7.2, 210 mOsm/kg). In both flasks, the dosage form was placed in a wire support to keep the tablet off of the bottom of the flask so that all surfaces were exposed to the solution, and the solutions were stirred using paddles rotating at 50 rpm. At preselected time intervals, a single tablet was removed and placed in recovery solution (50/50 w/w ethanol/water, pH 3) to dissolve the sertraline remaining in the tablet. Residual sertraline was analyzed by HPLC using a Phenomenex Ultracarb 5 ODS 20 column. The mobile phase consisted of 35 vol % TEA-acetate buffer (3.48 mL triethanolamine and 2.86 mL glacial acetic acid in 1 L HPLC-grade $H_2O$) in acetonitrile. Sertraline concentration was calculated by comparing UV absorbance at 230 nm to the absorbance of known sertraline controls. The amount remaining in the tablets was subtracted from the initial amount of sertraline in the tablets (73 mgA) to obtain the amount released at each time interval. Results are shown in Table 18 and are summarized in Table D.

TABLE 18

| Time (hours) | Drug Release (wt %) |
| --- | --- |
| 0 | 0 |
| 1 | 3 |
| 2 | 4 |
| 4 | 32 |
| 8 | 74 |
| 12 | 78 |
| 16 | 86 |
| 20 | 89 |

The data show that 4 wt % of the sertraline was released within 2 hours, and that 74 wt % of the sertraline was released within 8 hours. After 20 hours, 89% of the sertraline contained in the tablet had been released. Observations of the tablets during the release test indicated that the coating remained intact for the duration of the test.

EXAMPLE 19

This example demonstrates a process one could use for forming a dosage form of the present invention. To form the sertraline-containing composition, place 800 g of sertraline HCl, 1080 g of Polyox N80 (Union Carbide, PEO with a molecular weight of 200,000 daltons, NF grade) and 100 g of Klucel EF (Union Carbide, hydroxypropyl cellulose, NF grade) into the 10 L bowl of a Niro SP1 high-shear granulator. Blend for 5 minutes using a 300-rpm impeller speed and 1000 rpm chopper speed. Continue mixing for 6 minutes at the same speed while pumping in 310 g of an 85/15 (wt/wt) isopropyl alcohol/water mixture at a rate of 80 g/min, such that all 310 g of the IPA/water mixture is added within 4 minutes. After 6 minutes, set the impeller speed to 500 rpm, keeping the chopper speed at 1000 rpm) and mix for 30 seconds. Discharge the wet granulation from the bowl. Next, pass the wet granulation through a Fitzpatrick M5A mill equipped with a 0.093-inch plate, knives forward, running at 300 rpm. Place the wet-milled granulation on a polyethylene lined oven tray at a depth of less than 1 inch and dry in a convection oven at 40° C. for approximately 16 hours. Next, pass the dried granulation through a Fitzpatrick M5A mill equipped with a 0.030-inch Conidor rasping plate, knives forward, running at 300 rpm. Based on the actual weight of material from the milling, add 1.0 wt % magnesium stearate (20 g to 1980 g of milled granulation) with the milled granulation and mix in a 16-quart V-blender for 5 minutes.

To form the water-swellable composition, place 2578 g of Polyox WSR coagulant grade (Union Carbide, PEO with a molecular weight of 5,000,000 daltons, NF grade), 1200 g of NaCl and 200 g of METHOCEL E5 premium LV (Union Carbide, hydroxypropyl cellulose, NF grade) in a 16-quart PK-blender. Mix for 10 minutes. Pass this mixture through a Fitzpatrick M5A mill equipped with a 0.079-inch screen running at 300 rpm to remove lumps. Bottle blend 200 g of this mixture with 2.0 g of Red Lake #40 that has been passed through a #40 sieve for 5 minutes. Add this to a V-blender with the remainder of the above mixture and mix for 10 minutes. Based on the actual weight of the material mixed, add 0.5 wt % magnesium stearate to the V-blender and mix for 5 minutes to achieve the final blend.

To form the core, set up a bi-layer tablet press for the tablet size appropriate for the desired size of the dosage form. For example for a 150 mgA dose, $\frac{7}{16}$-inch standard round concave (SRC) tooling should be used; for a 75 mgA dose, $\frac{11}{32}$-inch SRC tooling should be used; for a 25 mgA dose, $\frac{7}{32}$-inch SRC tooling should be used. After measuring the potency of the sertraline-containing composition, determine the amount of sertraline-containing composition to be used for the desired dose. Next, calculate the amount of water-swellable composition required assuming the following total core weights: 617 mg for the 150-mgA dose, 333 mg for the 75-mgA dose, and 111 mg for the 25-mgA dose. Form the cores on the tablet press by first adding the desired amount of sertraline-containing composition, followed by the desired amount of water-swellable composition. Adjust the dwell time and compression force such that the cores have a hardness of 8 to 10 Kp for the 150 mgA dosage, 5 to 7 Kp for the 75 mgA dosage, and 3 to 5 Kp for the 25 mgA dosage.

To form the coating, first prepare about 3000 g of the desired coating solution by dissolving PEG 3350 (75 g for a 150 mgA dosage, 60 g for a 75 mgA dosage, or 30 g for a 25 mgA dosage) in 150 g of purified water in a 4-L Erlenmeyer flask. Add 2550 g of acetone to this solution. Place the flask in a container of warm water and begin vigorously mixing using an overhead stirrer. While mixing, slowly add type 398-10 cellulose acetate (225 g for the 150 mgA dosage, 240 g for the 75 mgA dosage, 270 g for the 25 mgA dosage) and mix for 1 to 2 hours, or until the solution is clear. Other coating-solution compositions could be used if a higher (greater PEG content) or lower water permeability (less PEG content) is required to obtain the desired release profile.

Next, assemble a pan coater, such as the HCT30-EP Hi-Coater. For this coater, use a $\frac{1}{8}$-inch JAC s/s nozzle body with the 2850 fluid cap. Add air cap 104228-45 onto the fluid cap. Warm the coater to about 30° C. by setting the inlet temperature to 42° C. Set the atomizing air to 15 psi and the pump to deliver approximately 20 g of coating solution per minute. Charge the HCT30-EP coating pan with approximately 1 kg of tablet cores of the appropriate size. Process parameters including spray rate, inlet temperature, exhaust temperature, air flow and pump rate should be adjusted in order to optimize product integrity while maintaining an outlet temperature of 28–30° C. during the coating operation. Continue the coating process until the desired coating weight is obtained adjusting for dampness (17 wt % for 150 mgA, 10 hour release; 17 wt % for 75 mgA, 10 hour release; 10 wt % for 75 mgA, 6 hour release; 18 wt % for 25 mgA, 10 hour release). Dry the tablets for 16 hours in a convection oven set to 40° C. Use a laser-drilling machine to drill one 700 μm delivery port on the sertraline-containing composition side of the tablet. The number of laser pulses should be adjusted to assure penetration through the coating with minimal drilling through the core.

EXAMPLE 20

This example describes a method one could use to prepare a sertraline-containing composition using sertraline that has been jet-milled to reduce the size of the sertraline crystals. First, place 800 g of jet-milled sertraline HCl, 1080 g of Polyox N80 (Union Carbide, PEO with a molecular weight of 200,000 daltons, NF grade) and 100 g of Klucel EF (Union Carbide, hydroxypropyl cellulose, NF grade) into the 10 L bowl of a Niro SP1 high-shear granulator. Blend for 5 minutes using a 300 rpm impeller speed and 1000 rpm chopper speed. Continue mixing for 6 minutes at the same speed while pumping in 335 g of an 85/15 (wt/wt) isopropyl alcohol/water mixture at a rate of about 85 g/min, such that all 335 g of the IPA/water mixture is added within 4 minutes. After 6 minutes, set the impeller speed to 500 rpm (keeping the chopper speed at 1000 rpm), and mix for 30 seconds. Discharge the wet granulation from the bowl. Next, pass the wet granulation through a Fitzpatrick M5A mill equipped with a 0.093-inch plate, knives forward, running at 300 rpm. Place the wet-milled granulation on a polyethylene lined oven tray at a depth of less than 1 inch and dry in a convection oven at 40° C. for approximately 16 hours. Next, pass the dried granulation through a Fitzpatrick M5A mill equipped with a 0.030 inch Conidor rasping plate, knives forward, running at 300 rpm. Based on the actual weight of material from the milling, add 1.0 wt % magnesium stearate (20 g to 1980 g of milled granulation) with the milled granulation and mix in a 16 quart V-blender for 5 minutes. The so-formed sertraline-containing composition could then be used to form tablets as described in Example 19.

EXAMPLE 21

This example describes a method one could use to prepare a sertraline-containing composition containing fumaric acid. First, place 758 g of sertraline HCl, 142 g of fumaric acid, 980 g of Polyox N80 (Union Carbide, PEO with a molecular weight of 200,000 daltons, NF grade) and 100 g of Klucel EF (Union Carbide, hydroxypropyl cellulose, NF grade) into the 10 L bowl of a Niro SP1 high-shear granulator. Blend for 5 minutes using a 300 rpm impeller speed and 1000 rpm chopper speed. Continue mixing for 6 minutes at the same speed while pumping in 260 g of an 85/15 (wt/wt) isopropyl alcohol/water mixture at a rate of about 65 g/min, such that all 260 g of the IPA/water mixture is added within 4 minutes. After 6 minutes, set the impeller speed to 500 rpm, keeping the chopper speed at 1000 rpm) and mix for 30 seconds. Discharge the wet granulation from the bowl. Next, pass the wet granulation through a Fitzpatrick M5A mill equipped with a 0.093-inch plate, knives forward, running at 300 rpm. Place the wet-milled granulation on a polyethylene lined oven tray at a depth of less than 1 inch and dry in a convection oven at 40° C. for approximately 16 hours. Next, pass the dried granulation through a Fitzpatrick M5A mill equipped with a 0.030 inch Conidor rasping plate, knives forward, running at 300 rpm. Based on the actual weight of material from the milling, add 1.0 wt % magnesium stearate (20 g to 1980 g of milled granulation) with the milled granulation and mix in a 16-quart V-blender for 5 minutes. The so-formed sertraline-containing composition could then be used to form tablets as described in Example 19. Note that other organic acids, such as tartaric acid can be substituted for the fumaric acid to obtain a similar composition.

EXAMPLE 22

This example describes a method one could use to prepare a sertraline-containing composition using sertraline lactate. First, place 800 g of sertraline lactate, 1080 g of Polyox N80 (Union Carbide, PEO with a molecular weight of 200,000 daltons, NF grade) and 100 g of Klucel EF (Union Carbide, hydroxypropyl cellulose, NF grade) into the 10-L bowl of a Niro SP1 high-shear granulator. Blend for 5 minutes using a 300-rpm impeller speed and 1000 rpm chopper speed. Continue mixing for 6 minutes at the same speed while pumping in 320 g of an 85/15 (w/w) isopropyl alcohol/water mixture at a rate of about 80 g/min, such that all 320 g of the IPA/water mixture is added within 4 minutes. After 6 minutes, set the impeller speed to 500 rpm, keeping the chopper speed at 1000 rpm) and mix for 30 seconds. Discharge the wet granulation from the bowl. Next, pass the wet granulation through a Fitzpatrick M5A mill equipped with a 0.093-inch plate, knives forward, running at 300 rpm. Place the wet-milled granulation on a polyethylene lined oven tray at a depth of less than 1 inch and dry in a convection oven at 40° C. for approximately 16 hours. Next, pass the dried granulation through a Fitzpatrick M5A mill equipped with a 0.030-inch Conidor rasping plate, knives forward, running at 300 rpm. Based on the actual weight of material from the milling, add 1.0 wt % magnesium stearate (20 g to 1980 g of milled granulation) with the milled granulation and mix in a 16-quart V-blender for 5 minutes. The so-formed sertraline-containing composition could then be used to form tablets as described in Example 19.

EXAMPLE 23

This example demonstrates another process one could use for forming a dosage form of the present invention. To form the sertraline-containing composition, place 800 g of sertraline HCl, 1080 g of Polyox N80 (Union Carbide, PEO with a molecular weight of 200,000 daltons, NF grade with low BHT level) and 100 g of Klucel EF (Union Carbide, hydroxypropyl cellulose, NF grade) into the 10 L bowl of a Niro SP1 high-shear granulator. Blend for 5 minutes using a 300-rpm impeller speed and 1000 rpm chopper speed. Continue mixing for 10 minutes at the same speed while pumping in 310 g of a 85/15 (wt/wt) isopropyl alcohol/water mixture at a rate of 80 g/min, such that all 310 g of the IPA/water mixture is added within 4 minutes. Microwave dry the granulation, being careful to avoid any melting of the mixture (alternatively, tray dry the granulation at 40° C. for greater than 6 hours using a convection oven). Once dry, mill the granulation to the appropriate size (e.g., a 0.030-inch screen). Based on the actual weight of material from the milling, add 1.0 wt % magnesium stearate (20 g to 1980 g of milled granulation) with the milled granulation and mix in a 16 quart V-blender for 5 minutes.

To form the water-swellable composition, place 2578 g of Polyox WSR coagulant grade (Union Carbide, PEO with a molecular weight of 5,000,000 daltons, NF grade), 1200 g of NaCl (powdered grade; Morton) and 200 g of Methocel E5 premium LV (Union Carbide, hydroxypropyl cellulose, NF grade) in a high-shear granulator. Mix for 5 minutes. Continue mixing for 10 minutes at the same speed while pumping in sufficient ethanol to reach the granulation end point. Dry the wet granulation using microwave drying (alternatively, tray drying using a convection oven can be used), then mill with a 0.030-inch screen. Combine this milled granulation with 0.5 wt % magnesium stearate in a V-blender and mix for 5 minutes to achieve the final blend.

To form the cores, set up a bi-layer tablet press for the tablet size appropriate for the desired size of the dosage form. For example for a 75 mgA dose, ¹¹⁄₃₂-inch SRC tooling should be used. After measuring the potency of the sertraline-containing composition, determine the amount of sertraline-containing composition to be used. Next, calculate the amount of water-swellable composition required assuming a total core weight of 333 mg for the 75 mgA dose. Form the cores on the tablet press by first adding the desired amount of sertraline-containing composition, followed by the desired amount of water-swellable composition. Adjust the dwell time and compression force such that the cores have a hardness of 5 to 7 Kp.

To form the coating, first prepare about 3000 g of the desired coating solution as described above in example 19.

Apply the coating to the cores using a pan coater using the operating conditions outlined in Example 19. Continue the coating process until the desired coating weight is obtained. Dry the tablets for more than 6 hours in a convection oven set to 40° C. Use a laser drilling machine to drill one 700 μm delivery port on the sertraline-containing composition side of the tablet.

TABLE A

Summary of Composition of the Sertraline-Containing Composition for All Examples

| Example | [Sertraline] wt % | PEO Type | [PEO] wt % | Binder Type | [Binder] wt % | [Mg Stearate] wt % | Other Ingredients | Conc. wt % | Processing Method |
|---|---|---|---|---|---|---|---|---|---|
| 1 | 22.8 | PEO 200K | 71.7 | Methocel K3LV | 5.0 | 0.5 | | | Dry Blended |
| 2A | 19.7 | PEO 200K | 74.2 | Klucel EF | 5.0 | 1.1 | | | Dry Blended |
| 2B | 35.0 | PEO 200K | 59.6 | Methocel K3LV | 5.0 | 0.5 | | | Dry Blended |
| 2C | 40.0 | PEO 200K | 54.0 | Klucel EF | 5.0 | 1.0 | | | Dry Blended |
| 2D | 49.5 | PEO 200K | 44.5 | Klucel EF | 5.0 | 1.0 | | | Dry Blended |
| 3A | 34.95 | PEO 200K PEO 300K | 29.7 29.7 | Methocel K3LV | 4.95 | 0.5 | | | Dry Blended |
| 3B | 35.0 | PEO 600K | 29.0 | None | 0.0 | 1.0 | Xylitab 200 Explotab | 30.0 5.0 | Dry Blended |
| 3C | 40.5 | PEO 300K | 54.0 | Klucel EF | 4.5 | 1.0 | | | Drug & binder wet granulated (water), then dry blended with other ingredients |
| Control 3D | 40.5 | PEO 200K | 54.0 | Klucel EF | 4.5 | 1.0 | | | Drug & binder wet granulated (water), then dry blended with other ingredients |
| 4A | 40.5 | PEO 200K | 54.0 | Klucel EF | 4.5 | 1.0 | | | Drug & binder & 10% of total PEO wet granulated (water), then dry blended with other ingredients |
| 4B | 40.5 | PEO 200K | 54.0 | Klucel EF | 4.5 | 1.0 | | | Drug, binder, PEO wet granulated (water), then dry blended with other ingredients |
| 4C | 40.5 | PEO 200K | 54.0 | Klucel EF | 4.5 | 1.0 | | | Drug & binder wet granulated (water), then milled, then dry blended with other ingredients |
| 4D | 40.0 | PEO 200K | 54.0 | Klucel EF | 5.0 | 1.0 | | | Drug, binder, PEO, high-shear granulated using 85/15 w/w IPA/water, then dry blended with other ingredients |
| 5A | 30.0 | PEO 200K | 49.5 | Klucel EF | 4.5 | 1.5 | Citric acid | 15.0 | Dry Blended |
| 5B | 37.8 | PEO 200K | 48.8 | Klucel EF | 4.9 | 1.0 | Fumaric acid | 7.0 | Dry Blended |
| 5C | 29.9 | PEO 200K | 49.2 | Klucel EF | 4.5 | 1.5 | Citric acid | 14.9 | Dry Blended |
| 6A | 40.3 | PEO 200K | 53.7 | Klucel EF | 4.9 | 1.0 | | | Sertraline jet-milled, then drug, PEO, and binder wet granulated, then dry blended with other ingredients |
| Control 6B | 40.3 | PEO 200K | 53.7 | Klucel EF | 4.9 | 1.0 | | | Sertraline jet-milled, then dry blended with other ingredients |
| 7A | 34.8 (Sertraline lactate) | PEO 200K | 60.2 | Methocel K3LV | 4.5 | 0.5 | | | Dry Blended |
| 7B | 49 Sertraline lactate) | PEO 200K | 45 | Klucel EF | 4.5 | 1.5 | | | Dry Blended |
| 8 | 37.3 | PEO 200K | 49.2 | Klucel EF | 4.5 | 1.5 | NaCl | 7.5 | Dry Blended |
| 9 | 40.3 | PEO 200K | 53.7 | Klucel EF | 4.9 | 1.0 | | | Dry Blended |
| 10A | 22.8 | PEO 200K | 71.7 | Methocel K3LV | 5.0 | 0.5 | | | Dry Blended |
| 10B | 22.8 | PEO 200K | 71.7 | Methocel K3LV | 5.0 | 0.5 | | | Dry Blended |
| 10C | 40.3 | PEO 200K | 53.7 | Klucel EF | 4.9 | 1.0 | | | Dry Blended |
| 11A | 40.3 | PEO 200K | 53.7 | Klucel EF | 4.9 | 1.0 | | | Dry Blended |
| 11B | 35.0 | PEO 600K | 28.75 | None | 0.0 | 1.25 | Xylitab 200 Explotab | 30.0 5.0 | Dry Blended |

TABLE A-continued

Summary of Composition of the Sertraline-Containing Composition for All Examples

| Example | [Sertraline] wt % | PEO Type | [PEO] wt % | Binder Type | [Binder] wt % | [Mg Stearate] wt % | Other Ingredients | Conc. wt % | Processing Method |
|---|---|---|---|---|---|---|---|---|---|
| 12A | 40.0 | PEO 200K | 54.0 | Klucel EF | 5.0 | 1.0 | | | Milled drug and binder wet granulated (water), milled, then blended with other ingredients |
| 12B | 40.0 | PEO 200K | 54.0 | Klucel EF | 5.0 | 1.0 | | | Drug, binder, PEO, high-shear granulated using IPA, then dry blended with other ingredients |
| 13A | 40.0 | PEO 200K | 54.0 | Klucel EF | 5.0 | 1.0 | | | Drug, binder, PEO, high-shear granulated using 85/15 w/w IPA/water, then dry blended with other ingredients |
| Control 13B | 40.0 | PEO 200K | 54.0 | Klucel EF | 5.0 | 1.0 | | | Dry Blended |
| 14A | 40.0 | PEO 200K | 54.0 | Klucel EF | 5.0 | 1.0 | | | Drug, binder, PEO, high-shear granulated using 85/15 w/w IPA/water, then dry blended with other ingredients |
| 14B | 40.0 | PEO 200K | 54.0 | Klucel EF | 5.0 | 1.0 | | | Drug, binder, PEO, high-shear granulated using 85/15 w/w IPA/water, then dry blended with other ingredients |
| 15A | 40.3 | PEO 200K | 53.7 | Klucel EF | 4.9 | 1.0 | | | Drug, PEO, binder wet granulated (water), then blended with other ingredients |
| 15B | 40.3 | PEO 200K | 53.7 | Klucel EF | 4.9 | 1.0 | | | Drug, PEO, binder wet granulated (water), then blended with other ingredients |
| 15C | 40.3 | PEO 200K | 53.7 | Klucel EF | 4.9 | 1.0 | | | Drug, PEO, binder wet granulated (water), then blended with other ingredients |
| 15D | 40.3 | PEO 200K | 53.7 | Klucel EF | 4.9 | 1.0 | | | Drug, PEO, binder wet granulated (water), then blended with other ingredients |
| 15E | 40.3 | PEO 200K | 53.7 | Klucel EF | 4.9 | 1.0 | | | Drug, PEO, binder wet granulated (water), then blended with other ingredients |
| 16 | 20.57 | PEO 600K | 26.75 | none | 0 | 1.0 | HPMCP Xylitab 200 Explotab | 20.57 26.75 4.33 | Drug and HPMCP formed into solid dispersion; ingredients precompressed, Comilled |
| 17A | 19.9 | PEO 200K | 74.6 | Methocel K3LV | 5.0 | 0.5 | | | Dry Blended |
| 17B | 19.9 | PEO 200K | 74.6 | Methocel K3LV | 5.0 | 0.5 | | | Dry Blended |
| 17C | 19.9 | PEO 200K | 74.6 | Methocel K3LV | 5.0 | 0.5 | | | Dry Blended |
| 18 | 20 | PEO 600K | 29 | none | 0 | 1.0 | Tartaric HPMCAS Xylitab 200 | 15 20 15 | Blended, wet granulated w/ IPA/H2O (85/15), dried, milled, blended |
| 19 | 40 | PEO 200K | 54 | Klucel EF | 5.0 | 1.0 | | | Drug, binder, PEO, high-shear granulated using 85/15 w/w IPA/water, then dry blended with mg stearate |
| 20 | 40 | PEO 200K | 54 | Klucel EF | 5.0 | 1.0 | | | Sertraline Jet-milled; Drug, binder, PEO, high-shear granulated using 85/15 w/w IPA/water, then dry blended with mg stearate |
| 21 | 37.9 | PEO 200K | 49 | Klucel EF | 5.0 | 1.0 | Fumaric acid | 7.1 | Drug, binder, PEO, high-shear granulated using 85/15 w/w IPA/water, then dry blended with mg stearate |
| 22 | 40 (Sertraline lactate) | PEO 200K | 54 | Klucel EF | 5.0 | 1.0 | | | Drug, binder, PEO, high-shear granulated using 85/15 w/w IPA/water, then dry blended with mg stearate |

TABLE A-continued

Summary of Composition of the Sertraline-Containing Composition for All Examples

| Example | [Sertraline] wt % | PEO Type | [PEO] wt % | Binder Type | [Binder] wt % | [Mg Stearate] wt % | Other Ingredients | Conc. wt % | Processing Method |
|---|---|---|---|---|---|---|---|---|---|
| 23 | 40 | PEO 200K | 54 | Klucel EF | 5.0 | 1.0 | | | Drug, binder, PEO, high-shear granulated using 85/15 w/w IPA/water, microwave to dry, then dry blended with mg stearate |

TABLE B

Summary of Composition of the Water-Swellable Composition for All Examples

| Example | [PEO 5,000,0000] wt % | [NaCl] wt % | Binder Type | [Binder] wt % | [Mg Stearate] wt % | Other Ingredients | Conc. wt % | Processing Method |
|---|---|---|---|---|---|---|---|---|
| 1 | 65.0 | 29.3 | Methocel K3LV | 5.1 | 0.6 | | | Dry Blended |
| 2A | 64.9 | 29.5 | Methocel K3LV | 5.0 | 0.5 | Red Lake #40 | 0.1 | PEO, NaCl, Binder wet granulated (EtOH), then dry blended with other ingredients |
| 2B | 65.0 | 29.3 | Methocel K3LV | 5.1 | 0.6 | | | Dry Blended |
| 2C | 64.6 | 29.9 | Methocel K3LV | 5.0 | 0.4 | Red Lake #40 | 0.1 | PEO, NaCl, Binder wet granulated (EtOH), then dry blended with other ingredients |
| 2D | 64.7 | 29.8 | Methocel K3LV | 5.0 | 0.5 | | | Dry Blended |
| 3A | 65.0 | 29.4 | Methocel K3LV | 5.0 | 0.6 | | | Dry Blended |
| 3B | 65.0 | 29.4 | Methocel K3LV | 5.0 | 0.6 | | | Dry Blended |
| 3C | 64.3 | 29.2 | Methocel K3LV | 5.8 | 0.6 | Red Lake #40 | 0.1 | Dry Blended |
| Control 3D | 63.8 | 30.4 | Methocel K3LV | 5.2 | 0.5 | Red Lake #40 | 0.1 | Dry Blended |
| 4A | 63.8 | 30.4 | Methocel K3LV | 5.2 | 0.5 | Red Lake #40 | 0.1 | Dry Blended |
| 4B | 64.9 | 29.5 | Methocel K3LV | 5.0 | 0.5 | Red Lake #40 | 0.1 | Dry Blended |
| 4C | 63.3 | 30.1 | Methocel K3LV | 6.0 | 0.5 | Red Lake #40 | 0.1 | Dry Blended |
| 4D | 64.5 | 30.0 | Methocel K3LV | 5.0 | 0.5 | | | Dry Blended |
| 5A | 64.3 | 29.2 | Methocel K3LV | 5.9 | 0.6 | | | Dry Blended |
| 5B | 64.4 | 29.9 | Methocel K3LV | 5.1 | 0.5 | Red Lake #40 | 0.1 | Dry Blended |
| 5C | 64.3 | 14.6 | Methocel K3LV | 5.9 | 0.6 | Citric acid | 14.6 | |
| 6A | 64.9 | 29.5 | Methocel K3LV | 5.0 | 0.5 | Red Lake #40 | 0.1 | Dry Blended |
| Control 6B | 64.9 | 29.5 | Methocel K3LV | 5.0 | 0.5 | Red Lake #40 | 0.1 | PEO, NaCl, Binder wet granulated (EtOH), then dry blended with other ingredients |
| 7A | 64.7 | 28.8 | Methocel K3LV | 5.9 | 0.6 | | | Dry Blended |
| 7B | 63.3 | 30.1 | Methocel E5LV | 6.0 | 0.5 | Red Lake #40 | 0.1 | Dry Blended |
| 8 | 63.3 | 30.1 | Methocel K3LV | 6.0 | 0.5 | Red Lake #40 | 0.1 | Dry Blended |
| 9 | 63.8 | 30.4 (powdered) | Methocel K3LV | 5.2 | 0.5 | Red Lake #40 | 0.1 | Dry Blended |
| 10A | 94.3 | 0.0 | Methocel K3LV | 5.1 | 0.6 | | | Dry Blended |
| 10B | 0.0 | 0.0 | None | 0.0 | 0.5 | Explotab Prosolv 90 | 74.5 25.0 | Dry Blended |
| 10C | 74.6 | 19.7 | Methocel K3LV | 5.1 | 0.5 | Red Lake #40 | 0.1 | Dry Blended |
| 11A | 65.2 | 29.3 | Methocel K3LV | 4.9 | 0.5 | Red Lake #40 | 0.1 | Dry Blended |

TABLE B-continued

Summary of Composition of the Water-Swellable Composition for All Examples

| Example | [PEO 5,000,0000] wt % | [NaCl] wt % | Binder Type | [Binder] wt % | [Mg Stearate] wt % | Other Ingredients | Conc. wt % | Processing Method |
|---|---|---|---|---|---|---|---|---|
| 11B | None | None | None | 0.0 | 0.5 | Explotab<br>Prosolv 90 | 74.5<br>25.0 | Dry Blended |
| 12A–12B | NA | NA | NA | NA | NA | NA | NA | NA |
| 13A | 64.5 | 30.0 | Methocel K3LV | 5.0 | 0.5 | | | Dry Blended |
| Control 13B | 64.3 | 29.9 | Methocel K3LV | 5.1 | 0.6 | Red Lake #40 | 0.1 | Dry Blended |
| 14A | 64.5 | 30.0 | HPMC | 5.0 | 0.5 | | | Dry Blended |
| 14B | 64.5 | 30.0 | HPMC | 5.0 | 0.5 | | | Dry Blended |
| 15A | 63.8 | 30.4 | Methocel K3LV | 5.2 | 0.5 | Red Lake #40 | 0.1 | Dry Blended |
| 15B | 63.8 | 30.4 | Methocel K3LV | 5.2 | 0.5 | Red Lake #40 | 0.1 | Dry Blended |
| 15C | 63.8 | 30.4 | Methocel K3LV | 5.2 | 0.5 | Red Lake #40 | 0.1 | Dry Blended |
| 15D | 63.8 | 30.4 | Methocel K3LV | 5.2 | 0.5 | Red Lake #40 | 0.1 | Dry Blended |
| 15E | 63.8 | 30.4 | Methocel K3LV | 5.2 | 0.5 | Red Lake #40 | 0.1 | Dry Blended |
| 16 | None | none | none | 0 | 0.47 | Red Lake #40<br>Explotab<br>Prosolv 90 | 0.14<br>74.66<br>24.73 | Dry Blended |
| 17A | 65.0 | 29.3 | Methocel K3LV | 5.1 | 0.6 | | | Dry Blended |
| 17B | 65.0 | 29.3 | Methocel K3LV | 5.1 | 0.6 | | | Dry Blended |
| 17C | 65.0 | 29.3 | Methocel K3LV | 5.1 | 0.6 | | | Dry Blended |
| 18 | 64.4 | 30 | Methocel K3LV | 5.0 | 0.5 | Red Lake #40 | 0.1 | Blended, milled, blended |
| 19 | 64.45 | 30 | Methocel E5LV | 5.0 | 0.5 | Red Lake #40 | 0.05 | Blended, milled, blended |
| 20 | 64.45 | 30 | Methocel E5LV | 5.0 | 0.5 | Red Lake #40 | 0.05 | Blended, milled, blended |
| 21 | 64.45 | 30 | Methocel E5LV | 5.0 | 0.5 | Red Lake #40 | 0.05 | Blended, milled, blended |
| 22 | 64.45 | 30 | Methocel E5LV | 5.0 | 0.5 | Red Lake #40 | 0.05 | Blended, milled, blended |
| 23 | 64.5 | 30 | Methocel E5LV | 5.0 | 0.5 | | | PEO, NaCl, Binder high shear wet granulated (EtOH), microwave to dry, blend with mg stearate |

TABLE C

Summary of Details of Tablet Formulations for All Examples

| Example | Total tablet Core Weight (mg) | Sertraline mgA | Drug Layer | Sweller Layer | Ratio of Drug layer to Water-Swellable Layer (w/w) | [CA] wt % | [PEG] wt % | [H₂O] wt % | Coating Amount wt % of uncoated tablet | Number of Ports | Port size (μm) |
|---|---|---|---|---|---|---|---|---|---|---|---|
| 1 | 735 | 100 | 490 | 245 | 2.0 | 7 | 3 | 5 | 12.9% | 1 | 900 |
| 2A | 221 | 26 | 147 | 74 | 2.0 | 8 | 2 | 5 | 20.1% | 1 | 700 |
| 2B | 735 | 153 | 490 | 245 | 2.0 | 7 | 3 | 5 | 13.0% | 1 | 900 |
| 2C | 663 | 147 | 442 | 221 | 2.0 | 7 | 3 | 5 | 15.2% | 1 | 700 |
| 2D | 564 | 167 | 377 | 187 | 2.0 | 7 | 3 | 5 | 13.6% | 1 | 700 |
| 3A | 735 | 153 | 490 | 245 | 2.0 | 7 | 3 | 5 | 10.1% | 1 | 900 |
| 3B | 735 | 150 | 490 | 245 | 2.0 | 7 | 3 | 5 | 13.0% | 1 | 900 |
| 3C | 663 | 158 | 442 | 221 | 2.0 | 7 | 3 | 5 | 21.1% | 1 | 700 |
| Control 3D | 663 | 158 | 442 | 221 | 2.0 | 7 | 3 | 5 | 21.6% | 1 | 700 |
| 4A | 663 | 158 | 442 | 221 | 2.0 | 7 | 3 | 5 | 20.5% | 1 | 700 |
| 4B | 663 | 158 | 442 | 221 | 2.0 | 7 | 3 | 5 | 16.0% | 1 | 700 |
| 4C | 663 | 158 | 442 | 221 | 2.0 | 7 | 3 | 5 | 24.5% | 1 | 700 |
| 4D | 617 | 158 | 442 | 175 | 2.5 | 7 | 3 | 5 | 20.8% | 1 | 700 |
| 5A | 887 | 157 | 591 | 296 | 2.0 | 7 | 3 | 5 | 21.9% | 1 | 700 |
| 5B | 700 | 158 | 469 | 231 | 2.0 | 7 | 3 | 5 | 20.0% | 1 | 700 |
| 5C | 887 | 157 | 591 | 296 | 2.0 | 7 | 3 | 5 | 21.9% | 1 | 700 |

TABLE C-continued

Summary of Details of Tablet Formulations for All Examples

| Example | Total tablet Core Weight (mg) | Sertraline mgA | Drug Layer | Sweller Layer | Ratio of Drug layer to Water-Swellable Layer (w/w) | [CA] wt % | [PEG] wt % | [H₂O] wt % | Coating Amount wt % of uncoated tablet | Number of Ports | Port size (μm) |
|---|---|---|---|---|---|---|---|---|---|---|---|
| 6A | 663 | 158 | 442 | 221 | 2.0 | 7 | 3 | 5 | 18.6% | 1 | 700 |
| Control 6B | 633 | 158 | 442 | 221 | 2.0 | 7 | 3 | 5 | 15.6% | 1 | 700 |
| 7A | 735 | 131 | 490 | 245 | 2.0 | 7 | 3 | 5 | 13.5% | 1 | 900 |
| 7B | 663 | 165 | 442 | 221 | 2.0 | 7 | 3 | 5 | 21.2 | 1 | 700 |
| 8 | 700 | 158 | 469 | 231 | 2.0 | 7 | 3 | 5 | 20.0% | 1 | 700 |
| 9 | 663 | 158 | 442 | 221 | 2.0 | 7 | 3 | S | 15.0% | 1 | 700 |
| 10A | 735 | 100 | 490 | 245 | 2.0 | 7 | 3 | 5 | 15.2% | 1 | 900 |
| 10B | 735 | 100 | 490 | 245 | 2.0 | 7 | 3 | 5 | 12.6% | 1 | 900 |
| 10C | 665 | 158 | 444 | 221 | 2.0 | 7 | 3 | 5 | 18.6% | 1 | 700 |
| 11A | 539 | 158 | 442 | 97 | 4.6 | 7 | 3 | 5 | 23.0% | 1 | 700 |
| 11B | 500 | 125 | 400 | 100 | 4.0 | 7 | 3 | 5 | 9.6% | 5 | 900 |
| 12 | NA | NA | NA | NA | NA | NA | NA | NA | NA | NA | NA |
| 13A | 111 | 26 | 74 | 37 | 2.0 | 8 | 2 | 5 | 15.2% | 1 | 700 |
| Control 13B | 110.4 | 25 | 73.6 | 36.8 | 2.0 | 8 | 2 | 5 | 15.2% | 1 | 700 |
| 14A | 617 | 153 | 442 | 175 | 2.5 | 7 | 3 | 5 | Various | 1 | 700 |
| 14B | 663 | 158 | 442 | 221 | 2.0 | 8 | 2 | 5 | Various | 1 | 700 |
| 15A | 663 | 158 | 442 | 221 | 2.0 | 7 | 3 | 5 | 21.6% | 1 | 700 |
| 15B | 663 | 158 | 442 | 221 | 2.0 | 7 | 3 | 5 | 21.6% | 2 (1 each side) | 700 |
| 15C | 663 | 161 | 442 | 221 | 2.0 | 7 | 3 | 5 | 21.4% | 1 | 700 |
| 15D | 663 | 161 | 442 | 221 | 2.0 | 7 | 3 | 5 | 21.4% | 1 | 900 |
| 15E | 663 | 161 | 442 | 221 | 2.0 | 7 | 3 | 5 | 21.4% | 1 | 2000 |
| 16 | 700 | 113 | 550 | 150 | 3.7 | 7 | 3 | 5 | 9.7% | 5 | 2000 |
| 17A | 735 | 98 | 490 | 245 | 2.0 | 7 | 3 | 5 | 11.2 | 0 | NA |
| 17B | 735 | 98 | 490 | 245 | 2.0 | 8 | 2 | 5 | 11.4 | 0 | NA |
| 17C | 735 | 98 | 490 | 245 | 2.0 | 9 | 1 | 5 | 11.7 | 0 | NA |
| 18 | 669 | 73 | 441.5 | 227.5 | 1.9 | 7 | 3 | 5 | 20.4 | 1 | 2000 |
| 19 | Various | Various | Various | Various | 2.0 | 7.5 | 2.5 | 5.0 | Various | 1 | 700 |
| 20 | Various | Various | Various | Various | 2.0 | 7.5 | 2.5 | 5.0 | Various | 1 | 700 |
| 21 | Various | Various | Various | Various | 2.0 | 7.5 | 2.5 | 5.0 | Various | 1 | 700 |
| 22 | Various | Various | Various | Various | 2.0 | 7.5 | 2.5 | 5.0 | Various | 1 | 700 |
| 23 | Various | Various | Various | Various | 2.0 | 7.5 | 2.5 | 5.0 | Various | 1 | 700 |

TABLE D

Summary of Release Rates in wt % for All Examples

| Example | 2-hr release | 8-hr release | 12-hr release | 20-hr release | 24-hr release | 2–12 hr release rate (%/hr) | Amount Released in 8 to 24 hours |
|---|---|---|---|---|---|---|---|
| 1 | 19 | 98 | 99 | | 99 | 8.0 | 1 |
| 2A | 4 | 85 | 97 | | 99 | 9.3 | 14 |
| 2B | 25 | 97 | 98 | | 98 | 7.3 | 1 |
| 2C | 5 | 65 | 88 | | 95 | 8.3 | 30 |
| 2D | 8 | 72 | 75 | | 77 | 6.7 | 5 |
| 3A | 16 | 97 | 99 | | 99 | 8.3 | 2 |
| 3B | 15 | 80 | 90 | | 87 | 7.5 | 7 |
| 3C | 0 | 37 | 78 | 98 | | 7.8 | 61 |
| Control 3D | 2 | 42 | 58 | | 63 | 5.6 | 21 |
| 4A | 7 | 74 | 96 | 98 | | 8.9 | 24 |
| 4B | 14 | 94 | 99 | | 100 | 8.5 | 6 |
| 4C | 4 | 70 | 94 | 97 | | 9.0 | 27 |
| 4D | 5 | 68 | 89 (10 hr) | | 89 | 8.4 | 21 |
| 5A | 3 | 69 | 91 | | 92 | 8.8 | 23 |
| 5B | 9 | 79 | 96 | 96 | | 8.7 | 17 |
| 5C (drug) | 6 | 65 | 94 | 96 | | 8.8 | 31 |
| (citric acid) | 9 | 62 | 84 | 93 | | 7.5 | 31 |
| 6A | 9 | 81 | 99 | 100 | | 9.0 | 19 |
| Control 6B | 1 | 43 | 60 | | 61 | 5.9 | 18 |
| 7A | 13 | 82 | 87 | | 86 | 7.4 | 4 |
| 7B | 3 | 73 | 87 | 90 | | 8.4 | 17 |
| 8 | 10 | 76 | 83 | 84 | | 7.3 | 8 |
| 9 | 6 | 91 | 101 | | 102 | 9.5 | 11 |
| 10A | 18 | 67 | 78 | | 92 | 6.0 | 25 |
| 10B | 17 | 70 | 84 | | 92 | 6.7 | 22 |
| 10C | 7 | 79 | 101 | | 103 | 9.4 | 24 |

TABLE D-continued

Summary of Release Rates in wt % for All Examples

| Example | 2-hr release | 8-hr release | 12-hr release | 20-hr release | 24-hr release | 2–12 hr release rate (%/hr) | Amount Released in 8 to 24 hours |
|---|---|---|---|---|---|---|---|
| 11A | 8 | 64 | 82 | 94 | | 7.4 | 30 |
| 11B | 22 | 79 | 88 | 94 | NA | 6.6 | 15 |
| 12 | NA | NA | NA | | NA | NA | NA |
| 13A | 25 | 94 | 94 (10 hr) | | 96 | 7.0 | 1.8 |
| Control 13B | 16 | 65 | 67 | 66 | | 5.1 | 1.0 |
| 14A | NA | NA | NA | | NA | NA | NA |
| 14B | NA | NA | NA | | NA | NA | NA |
| 15A | 8 | 90 | 101 | | 102 | 9.3 | 12 |
| 15B | 6 | 83 | 100 | 101 | | 9.4 | 18 |
| 15C | 0.3 | NA | NA | | NA | NA | NA |
| 15D | 2.2 | NA | NA | | NA | NA | NA |
| 15E | 3.0 | NA | NA | | NA | NA | NA |
| 16 | 17 | 68 | 86 | | 86 | 6.9 | 18 |
| 17A | NA | NA | NA | | NA | NA | NA |
| 17B | NA | NA | NA | | NA | NA | NA |
| 17C | NA | NA | NA | | NA | NA | NA |
| 18 | 4 | 74 | 78 | 89 | | 7.4 | 15 |
| 19 | NA | NA | NA | | NA | NA | NA |
| 20 | NA | NA | NA | | NA | NA | NA |
| 21 | NA | NA | NA | | NA | NA | NA |
| 22 | NA | NA | NA | | NA | NA | NA |
| 23 | NA | NA | NA | | NA | NA | NA |

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A dosage form for the controlled release of sertraline, comprising:
    (a) a core comprising a sertraline-containing composition and a water-swellable composition wherein said water-swellable composition is in a separate region within said core;
    (b) said sertraline-containing composition comprising sertraline and polyethylene oxide wherein sertraline makes up at least about 20 wt % of said sertraline-containing composition; and
    (c) a coating around said core that is water-permeable, water-insoluble and has at least one delivery port therethrough;
wherein sertraline is in the form of a pharmaceutically acceptable salt thereof and, following introduction of said dosage form to an environment of use, said dosage form releases sertraline to said environment of use at an average rate of from about 6 to 10 wt % per hour from the second to the twelfth hour and releases less than about 25 wt % for the first two hours and releases at least 70 wt % by the twelfth hour.

2. A dosage form for the controlled release of sertraline, comprising:
    (a) a core comprising a sertraline-containing composition and a water-swellable composition wherein said water-swellable composition is in a separate region within said core;
    (b) said sertraline-containing composition comprising sertraline, polyethylene oxide having a molecular weight of at least 500,000, and a fluidizing agent; and
    (c) a coating around said core that is water-permeable, water-insoluble and has at least one delivery port therethrough;
wherein sertraline is in the form of a pharmaceutically acceptable salt thereof and, following introduction of said dosage form to an environment of use, said dosage form releases sertraline to said environment of use at an average rate of from about 6 to 10 wt % per hour from the second to the twelfth hour and releases less than about 25 wt % for the first two hours and releases at least 70 wt % by the twelfth hour.

3. A dosage form for the controlled release of sertraline, comprising:
    (a) a core comprising a sertraline-containing composition and a water-swellable composition wherein said water-swellable composition is in a separate region within said core;
    (b) said sertraline-containing composition comprising sertraline and a polymeric entraining agent wherein sertraline makes up at least about 20 wt % of said sertraline-containing composition; and
    (c) a coating around said core that is water-permeable, water-insoluble and has at least one delivery port therethrough;
wherein sertraline is in the form of a pharmaceutically acceptable salt thereof and, following introduction of said dosage form to an environment of use, said dosage form releases sertraline to said environment of use at an amount of less than about 25 wt % by the second hour and at least about 40 wt % by the eighth hour and releases at least about 25 wt % from the eighth to the twenty-fourth hour.

4. A dosage form for the controlled release of sertraline, comprising:
    (a) a core comprising a sertraline-containing composition and a water-swellable composition wherein said water-swellable composition is in a separate region within said core and contains substantially no osmotically effective agent;
    (b) said sertraline-containing composition comprising sertraline and a polymeric entraining agent; and
    (c) a coating around said core that is water-permeable, water-insoluble and has at least one delivery port therethrough;

wherein sertraline is in the form of a pharmaceutically acceptable salt thereof and, following introduction of said dosage form to an environment of use, said dosage form releases sertraline to said environment of use at an average rate of from about 6 to 10 wt % per hour from the second to the twelfth hour and releases less than about 25 wt % for the first two hours and releases at least 70 wt % by the twelfth hour.

5. A dosage form for the controlled release of sertraline, comprising:
  (a) a core comprising a sertraline-containing composition and a water-swellable composition wherein said water-swellable composition is in a separate region within said core;
  (b) said sertraline-containing composition comprising sertraline and a polymeric entraining agent; and
  (c) a hydrophilic cellulosic polymeric coating around said core that is porous, water-insoluble, and has at least one delivery port therethrough;
wherein sertraline is in the form of a pharmaceutically acceptable salt thereof and, following introduction of said dosage form to an environment of use, said dosage form releases sertraline to said environment of use at an average rate of from about 6 to 10 wt % per hour from the second to the twelfth hour and releases less than about 25 wt % for the first two hours and releases at least 70 wt % by the twelfth hour.

6. A method for treating a depressive or anorectic disorder, comprising administering to a mammal in need of such treatment a therapeutically effective amount of sertraline in a dosage form as defined in claim 1.

7. A method for treating a depressive or anorectic disorder, comprising administering to a mammal in need of such treatment a therapeutically effective amount of sertraline in a dosage form as defined in claim 2.

8. The dosage form of any one of claims 3, 4, or 5 wherein said polymeric entraining agent is selected from the group consisting of hydroxy propyl cellulose, hydroxy propyl methyl cellulose, hydroxy ethyl cellulose, methyl cellulose, polyvinyl pyrrolidone, and polyethylene oxide.

9. The dosage form of claim 8 wherein said polymeric entraining agent is polyethylene oxide.

10. The dosage form of claim 2 wherein said fluidizing agent is selected from the group consisting of a non-reducing sugar, a salt and an organic acid and wherein said fluidizing agent has an aqueous solubility of at least 30 mg/ml.

11. The dosage form of claim 10 wherein said sugar is selected from the group consisting of xylitol, mannitol, sorbitol, and maltitol.

12. The dosage form of claim 11 wherein said sugar is xylitol.

13. The dosage form of claim 10 wherein said salt is selected from the group consisting of sodium chloride, sodium acetate and sodium lactate.

14. The dosage form of claim 10 wherein said organic acid is selected from the group consisting of adipic acid, citric acid, malic acid, succinic acid, and tartaric acid.

15. The dosage form of claim 1, 3, 4, or 5 wherein said sertraline-containing composition further comprises a fluidizing agent selected from the group consisting of a non-reducing sugar, a salt and an organic acid and wherein said fluidizing agent has an aqueous solubility of at least 30 mg/ml.

16. The dosage form of any one of claims 1–5 wherein sertraline is present in an amount of at least 40 mgA.

17. The dosage form of any one of claims 1–5 wherein sertraline is present in an amount of at least 60 mgA.

18. The dosage form of claim 2, 4, or 5 wherein sertraline comprises at least about 20 wt % of said sertraline-containing position.

19. The dosage form of claim 1 wherein said polyethylene oxide in said sertraline-containing composition has a molecular weight of at least about 100,000 and less than about 400,000.

20. The dosage form of claim 9 wherein said polyethylene oxide in said sertraline-containing composition has a molecular weight of at least about 100,000 and less than about 400,000.

21. The dosage form of claim 1, 2, 3, 4, or 5 wherein said pharmaceutically acceptable sertraline-salt has a weight average particle size of less than about 10 μm.

22. The dosage form of claim 1 wherein at least a portion of said sertraline-containing composition is granulated.

23. The dosage form of claim 22 wherein said sertraline-containing composition has an average granule size immediately following the granulation process of less than about 350 μm and said polyethylene oxide has an average molecular weight of less than 250,000.

24. The dosage form of claim 22 wherein said sertraline-containing composition, immediately following granulation, has a weight average granule size greater than about 400 μm and said polyethylene oxide has a molecular weight of at least about 300,000.

25. The dosage form of claim 22 wherein at least a portion of said sertraline-containing composition is wet-granulated.

26. The dosage form of claim 25 wherein wet granulation takes place with a mixture of a lower alcohol and water.

27. The dosage form of claim 26 wherein said wet granulation is conducted via a high-shear granulation process.

28. The dosage form of claim 26 wherein said lower alcohol is isopropanol.

29. The dosage form of claim 28 wherein the water content of said mixture of isopropanol and water is from 1 wt % to 30 wt %.

30. The dosage form of claim 22 wherein said sertraline-containing composition is further wet-milled, oven-dried and dry-milled.

31. The dosage form of claim 9 wherein at least a portion said sertraline-containing composition is granulated.

32. The dosage form of claim 31 wherein said sertraline-containing composition has an average granule size immediately following the granulation process of less than about 350 μm and said polyethylene oxide has an average molecular weight of less than 250,000.

33. The dosage form of claim 31 wherein said sertraline-containing composition, immediately following granulation, has a weight average granule size greater than about 400 μm and said polyethylene oxide has a molecular weight of at least about 300,000.

34. The dosage form of claim 31 wherein at least a portion of said sertraline-containing composition is wet-granulated.

35. The dosage form of claim 34 wherein wet granulation takes place with a mixture of a lower alcohol and water.

36. The dosage form of claim 35 wherein said wet granulation is conducted via a high-shear granulation process.

37. The dosage form of claim 35 wherein said lower alcohol is isopropanol.

38. The dosage form of claim 37 wherein the water content of said mixture of isopropanol and water is from 1 wt % to 30 wt %.

39. The dosage form of claim 31 wherein said sertraline-containing composition is further wet-milled, oven-dried and dry-milled.

40. The dosage form of any one of claims 1–5 wherein said core comprises an antioxidant.

41. The dosage form of claim 40 wherein said antioxidant is selected from the group consisting of BHA, BHT, vitamin E and ascorbyl palmitate.

42. The dosage form of any one of claims 1–5 wherein said sertraline-containing composition comprises an antioxidant.

43. The dosage form of claim 42 wherein said antioxidant is selected from the group consisting of BHT, BHA, vitamin E, and ascorbyl palmitate.

44. The dosage form of any one of claims 1–5 wherein said water-swellable composition comprises an antioxidant.

45. The dosage form of claim 44 wherein said antioxidant is selected from the group consisting of BHT, BHA, vitamin E, and ascorbyl palmitate.

46. The dosage form of any one of claims 1–5 wherein said pharmaceutically acceptable salt form of sertraline is highly soluble.

47. The dosage form of claim 46 wherein said highly soluble salt form is selected from the group consisting of sertraline lactate, sertraline acetate, sertraline aspartate.

48. The dosage form of any one of claims 1–5 wherein said core includes a solubilizer.

49. The dosage form of claim 48 wherein said solubilizer is an organic acid.

50. The dosage form of claim 49 wherein said organic acid is selected from the group consisting of adipic acid, citric acid, fumaric acid, malic acid, succinic acid, and tartaric acid.

51. The dosage form of claim 50 wherein the organic acid is selected from the group consisting of tartaric acid, succinic acid, and fumaric acid.

52. The dosage form of claim 51 wherein said organic acid is tartaric acid and is present in an amount equal to at least 3 wt % of said core.

53. The dosage form of claim 51 wherein said organic acid is fumaric acid and is present in an amount equal to at least 3 wt % of said core.

54. The dosage form of claim 48 wherein at least 20 wt % of said solubilizer is delivered to said use environment between 8 and 24 hours after introduction of said dosage form to said use environment.

55. The dosage form of any one of claims 1–5 wherein said sertraline-containing composition includes a solubilizer.

56. The dosage form of claim 55 wherein said solubilizer is an organic acid.

57. The dosage form of claim 56 wherein said organic acid is selected from the group consisting of adipic acid, citric acid, fumaric acid, malic acid, succinic acid, and tartaric acid.

58. The dosage form of claim 57 wherein the organic acid is selected from tartaric acid and fumaric acid.

59. The dosage form of claim 58 wherein said organic acid is tartaric acid and is present in an amount equal to at least 3 wt % of said sertraline-containing composition.

60. The dosage form of claim 58 wherein said organic acid is fumaric acid and is present in an amount equal to at least 3 wt % of said core.

61. The dosage form of claim 55 wherein at least 20 wt % of said solubilizer is delivered to said use environment between 8 and 24 hours after introduction of said dosage form to said use environment.

62. The dosage form of any of claims 1–5 wherein said water-swellable composition includes a solubilizer.

63. The dosage form of claim 62 wherein said solubilizer is an organic acid.

64. The dosage form of claim 63 wherein said organic acid is selected from the group consisting of citric acid, malic acid, and tartaric acid.

65. The dosage form of claim 64 wherein said organic acid is citric acid and is present in an amount equal to at least 3 wt % of said water-swellable composition.

66. The dosage form of claim 62 wherein at least 20 wt % of said solubilizer is delivered to said use environment between 8 and 24 hours after introduction of said dosage form to said use environment.

67. The dosage form of any one of claims 1–5 wherein sertraline is present substantially as a single polymorph.

68. The dosage form of any one of claims 1–5 wherein said water-swellable composition comprises a water-swellable polymer selected from the group consisting of polyethylene oxide, sodium starch glycolate, and sodium cross-carmellose.

69. The dosage form of any one of claims 1–5 wherein said water-swellable composition includes a colorant that contains substantially no iron (III).

70. The dosage form of any one of claims 1, 2, 3, or 5 wherein said water-swellable composition includes an osmagent.

71. The dosage form of claim 70 wherein said osmagent is selected from the group consisting of sodium chloride, sodium lactate, sodium acetate, adipic acid, citric acid, lactic acid, fumaric acid, malic acid, succinic acid, tartaric acid, xylitol, mannitol, maltitol, and sorbitol.

72. The dosage form of any one of claims 1–3 or 5 wherein said water-swellable composition contains substantially no osmotically effective agent.

73. The dosage form of claim 68 wherein said polyethylene oxide in said water-swellable composition has a molecular weight of between 3,000,000 and 8,000,000.

74. The dosage form of any one of claims 1–5 wherein the water-swellable polymer in the water-swellable composition is only PEO and the mass of said sertraline-containing composition divided by the mass of said water-swellable composition is at least 1.5.

75. The dosage form of any one of claims 1–5 wherein the water-swellable polymer in the water-swellable composition comprises sodium starch glycolate or sodium cross-carmellose and the mass of said sertraline-containing composition divided by the mass of said water-swellable composition is at least 3.0.

76. The dosage form of any one of claims 1–5 wherein said dosage form is a tablet with a hardness H in Kp given by the expression:

$$(35D^2)-1 \leq H \leq (35D^2)+6$$

where D is the diameter in inches of the tooling used to compress said core.

77. The dosage form of any of claims 1–4 wherein said coating comprises a hydrophilic cellulosic polymer.

78. The dosage form of claim 77 wherein said hydrophilic cellulosic polymer is selected from the group consisting of cellulose acetate, and mixtures of cellulose acetate and a second polymer.

79. The dosage form of claim 5 wherein said hydrophilic cellulosic polymer is selected from the group consisting of cellulose acetate, and mixtures of cellulose acetate and a second polymer.

80. The dosage form of claim 77 wherein said hydrophilic cellulosic polymer is a plasticized or unplasticized version of a cellulose ester, cellulose ether or cellulose ester-ether.

81. The dosage form of claim 5 wherein said hydrophilic cellulosic polymer is a plasticized or unplasticized version of a cellulose ester, cellulose ether or cellulose ester-ether.

82. The dosage form of claim 80 wherein said cellulose ester, cellulose ether or cellulose ester-ether is selected from the group consisting of cellulose acetate, cellulose acetate butyrate and ethyl cellulose.

83. The dosage form of claim 82 wherein said hydrophilic cellulosic polymer has a degree of substitution equivalent to 25 to 42 wt % acetyl groups.

84. The dosage form of claim 83 wherein said hydrophilic cellulosic polymer has a degree of substitution equivalent to 39 to 41 wt % acetyl groups.

85. The dosage form of claim 82 wherein said cellulose acetate has a molecular weight of at least 45,000.

86. The dosage form of any one of claims 1–5 wherein said coating is formed from a solution having a weight ratio of cellulose acetate to polyethylene glycol of from 9:1 to 6.5:3.5.

87. The dosage form of any one of claims 1–5 wherein said coating is formed from a solution having a water concentration of greater than 4 wt %.

88. The dosage form of claim 86 wherein said coating is formed from a solution having a water concentration of greater than 4 wt %.

89. The dosage form of any one of claims 1–5 wherein said coating is formed from a solution having a water concentration of greater than 15 wt %.

90. The dosage form of claim 86 wherein said coating is formed from a solution having a water concentration of greater than 15 wt %.

91. The dosage form of any one of claims 1–5 wherein said coating in the dry state is porous with a density of less than 0.9 times that of the nonporous coating material.

92. The dosage form of claim 91 wherein said coating in the dry state has a density of less than 0.75 times that of the nonporous coating material.

93. The dosage form of claim 91 wherein said coating comprises a polymeric asymmetric membrane comprising a thick, porous region and a dense thin region.

94. The dosage form of any one of claims 1–5 wherein said coating has a water flux (40/75) of at least $1.0 \times 10^{-3}$ gm-hr/cm$^2$.

95. The dosage form of any one of claims 1–5 wherein said coating has a mass of from 3 to 30 wt % of said core.

96. The dosage form of claim 95 wherein said coating has a mass of from 8 to 25 wt % of said core.

97. The dosage form of any one of claims 1–5 wherein said dosage form has at least one delivery port in communication with said sertraline-containing composition and at least one other delivery port in communication with said water-swellable composition, and said water-swellable composition contains substantially no colorant.

98. The dosage form of any one of claims 1–5 wherein at least 5 wt % of sertraline is released into said use environment within 1 hour of said dosage form being introduced into said use environment.

99. The dosage form of claim 4 wherein said dosage form delivers less than 10 wt % of sertraline within 2 hours after introduction of said dosage form to said use environment.

100. The dosage form of any one of claims 1–2 wherein at least 80 wt % of sertraline is released into said use environment within 12 hours after introduction of said dosage form into said use environment.

101. The dosage form of claim 100 wherein at least 90 wt % of sertraline is released into said use environment within 12 hours after introduction of said dosage form into said use environment.

102. The dosage form of any one of claims 1–5 wherein said dosage form delivers at least 95 wt % of sertraline into said use environment within 24 hours after introduction of said dosage form into said use environment.

103. The dosage form of any one of claims 1–5 wherein said coating includes sertraline.

104. The dosage form of any one of claims 1–5 wherein said dosage form has an additional sertraline-containing coating surrounding said coating that is water-soluble or water erodible.

105. The dosage form of any one of claims 1–5 wherein at least a portion of said sertraline is released such that improved absorption of sertraline from the GI tract is observed relative to a dosage form that releases standard size sertraline hydrochloride crystals at the substantially same release profile.

106. The dosage form of any one of claims 1, 2, 4 or 5 wherein said dosage form releases sertraline to said environment of use at an average rate of from about 7 to about 12 wt % per hour from the second to the tenth hour and less than about 25 wt % for the first two hours and at least 70 wt % by the tenth hour.

107. The dosage form of any one of claims 1, 2, 4 or 5 wherein said dosage form releases sertraline to said environment of use at an average rate of from about 10 to about 16 wt % per hour from the second to the eighth hour and at least 70 wt % by the eighth hour.

108. A method for treating a depressive or anorectic disorder, comprising administering to a mammal in need of such treatment a therapeutically effective amount of sertraline in a dosage form as defined in claim 3.

109. A method for treating a depressive or anorectic disorder, comprising administering to a mammal in need of such treatment a therapeutically effective amount of sertraline in a dosage form as defined in claim 4.

110. A method for treating a depressive or anorectic disorder, comprising administering to a mammal in need of such treatment a therapeutically effective amount of sertraline in a dosage form as defined in claim 5.

111. A dosage form for the controlled release of sertraline, comprising:
(a) a core comprising a sertraline-containing composition and a water-swellable composition wherein each is in a separate region within said core;
(b) said sertraline-containing composition comprising sertraline, an entraining agent, and a concentration-enhancing polymer; and
(c) a coating around said core that is water-permeable, water-insoluble and has at least one delivery port therethrough;
wherein said dosage form provides a maximum concentration of sertraline in a use environment that is at least 1.25-fold higher than the equilibrium concentration of sertraline in said use environment provided by a control dosage form, and a concentration of sertraline in said use environment that exceeds said equilibrium concentration for a longer time than a concentration provided by said control dosage form exceeds said equilibrium concentration, wherein said control dosage form is free from said concentration-enhancing polymer and comprises an equivalent quantity of sertraline.

112. A method for treating a depressive or anorectic disorder, comprising administering to a mammal in need of such treatment a therapeutically effective amount of sertraline in a dosage form as defined in claim 111.

113. The dosage form of claim 111 wherein said sertraline-containing composition further comprises a solubilizer.

114. The dosage form of claim 111 wherein said sertraline is present as a highly-soluble salt form.

115. The dosage form of claim 111 wherein said concentration-enhancing polymer is selected from the group consisting of
(a) ionizable cellulosic polymers;
(b) non-ionizable cellulosic polymers; and
(c) vinyl polymers and copolymers having substituents selected from the group consisting of hydroxyl, alkylacyloxy, and cyclicamido.

116. The dosage form of claim 113 or 114 wherein said concentration-enhancing polymer is selected from the group consisting of
(a) ionizable cellulosic polymers;
(b) non-ionizable cellulosic polymers; and
(c) vinyl polymers and copolymers having substituents selected from the group consisting of hydroxyl, alkylacyloxy, and cyclicamido.

117. The dosage form of claim 116 wherein said concentration-enhancing polymer is a cellulosic polymer selected from the group consisting of cellulosic esters, cellulosic ethers, and cellulosic esters/ethers.

118. The dosage form of claim 116 wherein said concentration-enhancing polymer is selected from the group consisting of polyvinyl pyrrolidone, polyvinyl alcohol, copolymers of polyvinyl pyrrolidone and polyvinyl acetate and aqueous-soluble cellulosic polymers.

119. The dosage form of claim 113 wherein said solubilizer is an organic acid.

120. The dosage form of claim 119 wherein said organic acid is selected from the group consisting of adipic acid, citric acid, fumaric acid, malic acid, succinic acid, and tartaric acid.

121. The dosage form of claim 114 wherein said highly soluble salt form is selected from the group consisting of sertraline lactate, sertraline acetate, and sertraline aspartate.

122. The dosage form of claim 111 wherein said core comprises anantioxidant.

123. The dosage form of claim 111 wherein said sertraline-containing composition comprises an antioxidant.

124. The dosage form of claim 111 wherein said water-swellable composition comprises an antioxidant.

125. The dosage form of claim 111 wherein said water-swellable composition comprises a solubilizer.

126. The dosage form of claim 111 wherein said water-swellable composition comprises a water-swellable polymer selected from the group consisting of polyethylene oxide, sodium starch glycolate, and sodium croscarmellose.

127. The dosage form of claim 111 wherein said water-swellable composition comprises a colorant that contains substantially no iron (111).

128. The dosage form of claim 111 wherein the water-swellable polymer in the water-swellable composition is only PEO and the mass of said sertraline-containing composition divided by the mass of said water-swellable composition is at least 1.5.

129. The dosage form of claim 111 wherein the water-swellable polymer in the water-swellable composition comprises sodium starch glycolate or sodium croscarmellose and the mass of said sertraline-containing composition divided by the mass of said water-swellable composition is at least 3.0.

130. The dosage form of claim 112 wherein said dosage form is a tablet with a hardness H in Kp given by the expression:

$$(35D^2)-1 \leq H \leq (35D^2)+6$$

where D is the diameter in inches of the tooling used to compress said core.

131. The dosage form of claim 111 wherein said coating comprises a hydrophilic cellulosic polymer.

132. The dosage form of claim 111 wherein said coating is formed from a solution having a weight ratio of cellulose acetate to polyethylene glycol of from 9:1 to 6.5:3.5.

133. The dosage form of claim 111 wherein said coating is formed from a solution having a water concentration of greater than 4 wt %.

134. The dosage form of claim 111 wherein said coating is formed from a solution having a water concentration of greater than 15 wt %.

135. The dosage form of claim 111 wherein said coating in the dry state is porous with a density of less than 0.9 times that of the nonporous coating material.

136. The dosage form of claim 111 wherein said coating has a water flux (40/75) of at least $1.0 \times 10^{-3}$ gm-hr/cm$^2$.

137. The dosage form of claim 111 wherein said coating has a mass of from 3 to 30 wt % of said core.

138. The dosage form of claim 111 wherein said dosage form has at least one delivery port in communication with said sertraline-containing composition and at least one other delivery port in communication with said water-swellable composition, and said water-swellable composition contains substantially no colorant.

139. The dosage form of claim 111 wherein at least 5 wt % of sertraline is released into said use environment within 1 hour of said dosage form being introduced into said use environment.

140. The dosage form of claim 111 wherein at least 80 wt % of sertraline is released into said use environment within 12 hours after introduction of said dosage form into said use environment.

141. The dosage form of claim 111 wherein said dosage form delivers at least 95 wt % of sertraline into said use environment within 24 hours after introduction of said dosage form into said use environment.

142. The dosage form of claim 111 wherein said dosage form has an additional sertraline-containing coating surrounding said coating that is water-soluble or water erodible.

143. The dosage form of claim 111 wherein at least a portion of said sertraline is released such that improved absorption of sertraline from the GI tract is observed relative to a dosage form that releases standard size sertraline hydrochloride crystals at the substantially same release profile.

144. A method as claimed in claim 6, 7, 108, 109, 110, or 112, wherein said mammal is a human.

* * * * *